United States Patent
Wang et al.

(10) Patent No.: US 11,384,048 B2
(45) Date of Patent: Jul. 12, 2022

(54) AROMATIC VINYL OR AROMATIC ETHYL DERIVATIVE, PREPARATION METHOD THEREFOR, INTERMEDIATE, PHARMACEUTICAL COMPOSITION, AND APPLICATION

(71) Applicant: GUANGZHOU MAXINOVEL PHARMACEUTICALS CO., LTD., Guangzhou (CN)

(72) Inventors: Yuguang Wang, Guangzhou (CN); Nong Zhang, Guangzhou (CN); Tianzhi Wu, Guangzhou (CN); Min He, Guangzhou (CN)

(73) Assignee: GUANGZHOU MAXINOVEL PHARMACEUTICALS CO., LTD., Guangdong (CN)

( * ) Notice: Subject to any disclaimer, the term of this patent is extended or adjusted under 35 U.S.C. 154(b) by 0 days.

(21) Appl. No.: 16/958,588

(22) PCT Filed: Dec. 24, 2018

(86) PCT No.: PCT/CN2018/123066
§ 371 (c)(1),
(2) Date: Jun. 26, 2020

(87) PCT Pub. No.: WO2019/128918
PCT Pub. Date: Jul. 4, 2019

(65) Prior Publication Data
US 2021/0061755 A1  Mar. 4, 2021

(30) Foreign Application Priority Data
Dec. 29, 2017 (CN) .......................... 201711486872.3

(51) Int. Cl.
| | | |
|---|---|---|
| *C07C 229/22* | (2006.01) | |
| *C07D 213/38* | (2006.01) | |
| *C07D 231/56* | (2006.01) | |
| *C07D 235/02* | (2006.01) | |
| *C07D 241/12* | (2006.01) | |
| *C07D 261/20* | (2006.01) | |
| *C07D 263/56* | (2006.01) | |
| *C07D 319/16* | (2006.01) | |
| *C07D 407/10* | (2006.01) | |
| *C07D 471/04* | (2006.01) | |
| *C07D 487/04* | (2006.01) | |

(52) U.S. Cl.
CPC .......... *C07C 229/22* (2013.01); *C07D 213/38* (2013.01); *C07D 231/56* (2013.01); *C07D 235/02* (2013.01); *C07D 241/12* (2013.01); *C07D 261/20* (2013.01); *C07D 263/56* (2013.01); *C07D 319/16* (2013.01); *C07D 407/10* (2013.01); *C07D 471/04* (2013.01); *C07D 487/04* (2013.01)

(58) Field of Classification Search
CPC ........................... C07C 229/22; C07D 213/38
See application file for complete search history.

(56) References Cited

U.S. PATENT DOCUMENTS

| | | | |
|---|---|---|---|
| 11,078,192 B2 * | 8/2021 | Wang ...................... | C07C 47/55 |
| 2010/0292227 A1 | 11/2010 | Yoakim | |
| 2016/0194307 A1 | 7/2016 | Chupak et al. | |
| 2019/0308957 A1 | 10/2019 | Wang et al. | |

FOREIGN PATENT DOCUMENTS

| | | | |
|---|---|---|---|
| CA | 2304274 A1 | 4/1999 | |
| CN | 101712604 A | 5/2010 | |
| CN | 105705489 A | 6/2016 | |
| EP | 2952503 A1 | 12/2015 | |
| JP | 10195063 A | 7/1998 | |
| JP | 2001517646 A | 10/2001 | |
| JP | 2003502413 A | 1/2003 | |
| JP | 2011505341 A | 2/2011 | |
| JP | 2012526728 A | 11/2012 | |
| WO | 9804258 A | 2/1998 | |

(Continued)

OTHER PUBLICATIONS

Feb. 22, 2019, International Search Report issued in International Patent Application No. PCT/CN2018/123066.

(Continued)

*Primary Examiner* — Golam M Shameem
(74) *Attorney, Agent, or Firm* — Dilworth IP, LLC

(57) ABSTRACT

Disclosed in the present invention are an aromatic vinyl or aromatic ethyl derivative, a preparation method therefor, an intermediate, a pharmaceutical composition, and an application. The aromatic vinyl or aromatic ethyl derivative in the present invention is as represented by general formula (I). The aromatic vinyl or aromatic ethyl derivative in the present invention has an obvious inhibitory effect on PD-1/PD-L1, is a very effective small-molecule PD-1/PD-L1 inhibitor, and can effectively alleviate or treat relevant diseases such as cancer.

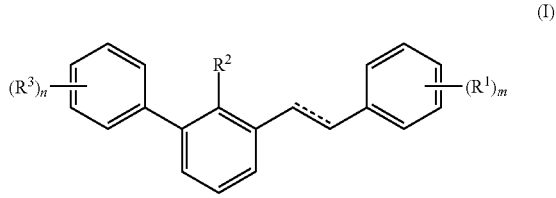

(I)

19 Claims, No Drawings

(56) References Cited

FOREIGN PATENT DOCUMENTS

| WO | 9804528 | A2 | 2/1998 |
|---|---|---|---|
| WO | 0078739 | A1 | 12/2000 |
| WO | 0153268 | A2 | 7/2001 |
| WO | 0162233 | A2 | 8/2001 |
| WO | 2004014865 | A1 | 2/2004 |
| WO | 2009067600 | A | 5/2009 |
| WO | 2011045344 | A1 | 4/2011 |
| WO | 2012168944 | A1 | 12/2012 |
| WO | 2015033299 | A1 | 3/2015 |
| WO | 2015033301 | A1 | 3/2015 |
| WO | 2015034820 | A1 | 3/2015 |
| WO | 2015036927 | A1 | 3/2015 |
| WO | 2015044900 | A1 | 4/2015 |
| WO | 2015160641 | A1 | 10/2015 |
| WO | 2017066227 | A1 | 4/2017 |
| WO | 2018006795 | A1 | 1/2018 |

OTHER PUBLICATIONS

Feb. 22, 2019, Written Opinion of the International Searching Authority issued in International Patent Application No. PCT/CN2018/123066.
L. L. Carter et al., "PD-1:PD-L inhibitory pathway affects both CD4+ and CD8+ T cells and is overcome by IL-2", Eur. J. Immunol., 2002, 32(3), 634-643.
Chinese Patent Application No. 2017114868723 (not published).
First Office Action issued in a corresponding Japanese Application No. 2019-500436, dated Mar. 22, 2021.
PCT International Search Report and Written Opinion dated Sep. 30, 2017 in corresponding Appl. No. PCT/CN2017/091643, 17 pages.
Liu et al., "Design and synthesis of 3'-(prop-2-yn-1-yloxy)-biphenyl substituted cyclic acylguanidine compounds as BACE1 inhibitors", Chinese Chemical Letters, vol. 27, No. 6, 2016, p. 961-963.
Liu et al., "Design and synthesis of cyclic acylguanidines as BACE1 inhibitors", Chinese Chemical Letters, vol. 26, No. 10, 2015, p. 1327-1330.
"RN1899005-22-1" Registry enter STN: Apr. 27, 2016.
"RN1646560-09-9" Registry enter STN: Feb. 11, 2015.
"RN1638536-50-1" Registry enter STN: Dec. 11, 2014.
"RN1225389-46-7" Registry enter STN: May 27, 2010.
"RN1225389-45-6" Registry enter STN: May 27, 2010.
"RN1098107-07-3" Registry enter STN: Jan. 30, 2009.
"RN1098106-07-0" Registry enter STN: Jan. 30, 2009.
"RN1098104-35-8" Registry enter STN: Jan. 30, 2009.
"RN263916-95-6" Registry enter STN: May 8, 2000.
"RN223654-82-8" Registry enter STN: May 28, 1999.
"RN1803418-36-1" Registry enter STN: Sep. 8, 2015.
"RN1581311-49-0" Registry enter STN: Apr. 7, 2014.
"RN1581311-48-9" Registry enter STN: Apr. 7, 2014.
"RN 1269763-65-6" Registry enter STN: Mar. 24, 2011.
"RN1106005-31-5" Registry enter STN: Feb. 15, 2009.
"RN1106005-25-7" Registry enter STN: Feb. 15, 2009.
"RN1051472-23-1" Registry enter STN: Sep. 22, 2008.
"RN934537-51-6" Registry enter STN: May 10, 2007.
"RN638214-15-0" Registry enter STN: Jan. 16, 2004.
"RN1258410-97-7" Registry enter STN: Jan. 5, 2011.
"RN264912-33-6" Registry enter STN: May 16, 2000.
"RN52500-13-7" Registry enter STN: Nov. 16, 1984.
Extended European Search Report dated Apr. 1, 2019, in corresponding European Patent Application No. 17823607.1, 14 pages.
Bly et al., "Heterocyclic studies. XIII. The aldol condensation of 2,3-dihydro-5-methyl-6-phenyl-4H-1,2 diazep in-4-one and reaarangement to a pyridazine", Journal of Organic Chemistry, vol. 29, No. 8, 1964, p. 2128-2135.
Malik et al., "Synthesis and photophysical properties of alkynylated pyrimidines by site—selective sonogashira reactions of 2,4,5,6-tetrachloropyrimidine; First synthesis of tetraalkynyl-pyrimidines", European Journal of Organic Chemisty, vol. 2011, No. 11, 2011, p. 2088-2093.
Nguyen et al. "Insulin-mimetic selaginellins from selaginella tamariscina with protein tyrosine phosphatase 1B (PTP1B) inhibitory activity", Journal of Natural Products, vol. 78, No. 1, 2015, p. 34-42.
Office Action issued in related European Patent Application No. 17823607.1, dated Dec. 17, 2020, 5 pages.
First Office Action in AU Patent Application No. 2017294231 dated Sep. 16, 2020.
First Office Action issued in the counterpart Singapore application No. 11202005962Y, dated Nov. 16, 2021.
Extended European Search Report in European Patent Application No. 18895140.4, dated Sep. 29, 2021.

\* cited by examiner

AROMATIC VINYL OR AROMATIC ETHYL DERIVATIVE, PREPARATION METHOD THEREFOR, INTERMEDIATE, PHARMACEUTICAL COMPOSITION, AND APPLICATION

The application claims priority of Chinese Patent Application CN201711486872.3 filed on Dec. 29, 2017, the contents of which are incorporated herein by reference in their entirety.

TECHNICAL FIELD

The present disclosure relates to an aromatic vinyl or aromatic ethyl derivative, a preparation method, an intermediate, a pharmaceutical composition and a use thereof.

BACKGROUND ART

PD-1 (programmed death 1) is a kind of important immunosuppressive molecule which is a member of the CD28 superfamily and was originally cloned from the apoptotic mouse T-cell hybridoma 2B4.11. Immunomodulation targeting PD-1 has important significance in anti-tumor, anti-infection, anti-autoimmune diseases and organ transplantation survival. Its ligand, PD-L1 can also serve as a target, and the corresponding antibodies can also play the same role.

PD-1/PD-L1 plays a role of a negative immunoregulation effect. When PD-1 and PD-L1 on the cell surface are coupled, it can cause Tyr phosphorylation of the Immunoreceptor Tyrosine-based Swith motifs (ITSM) domain in the T-cell cytoplasmic region, and then phosphorylated Tyr recruits tyrosine-protein phosphatase 2 and tyrosine-protein phosphatase 1 to block not only the activation of extracellular signal-regulated kinases, but also the activation of phosphatidylinositol 3-kinase (PI3K) and serine-threonine protein kinase (Akt), and ultimately inhibits T lymphocyte proliferation and secretion of related cytokines. PD-1/PD-L1 signaling can inhibit T-cell activation and proliferation, and at the same time, the secretion of cytokines interleukin 2 (IL2), interferon γ and IL-10 is also reduced (*Eur. J. Immunol.,* 2002, 32 (3), 634-643). In addition, the function of PD-1/PD-L1 signaling to the B-cell immune is also similar to that of T-cell. After PD-1 binds to B-cell antigen receptor, the PD-1 cytoplasmic domain interacts with the tyrosinase containing protein tyrosinase 2 binding site, and ultimately blocks the activation of B-cell. The role of immune negative regulator PD-1/PD-L1 in tumor immune escape has attracted more and more attention. A large number of studies have confirmed that the PD-L1 on the surface of tumor cells in the tumor microenvironment increases which binds to PD-1 on activated T cells at the same time and transmits negative regulatory signals, resulting in tumor antigen-specific T cell apoptosis or immune incompetence, thereby suppressing immune response, and further promoting escape of tumor cells.

Currently PD-1/PD-L1 antibody inhibitors that have been approved for market include Nivolumab (BMS, 2014), Lambrolizumab (Merck, 2014) and Atezolizumab (Roche, 2016). The PD-1/PD-L1 antibodies under research include Pidilizumab (Cure Tech), AMP-224 (GSK) and MEDI-4736 (AstraZeneca). These above are all biological macromolecules, but small molecule PD-1/PD-L1 inhibitors are still in the early stage of development. PD-L1 small molecule inhibitor AC-170 (Curis, WO2012168944, WO2015033299, WO2015033301, WO2015036927, WO2015044900) has just entered the clinical phase I, and the small molecule PD-1/PD-L1 inhibitors of BMS (WO2015034820, WO2015160641) are still in the preclinical research stage. Compared with biological macromolecules, small molecular compounds can penetrate cell membranes and act on intracellular targets, so they have a wide range of applications. Secondly, small molecules often have good bioavailability and compliance after chemical modification, thereby effectively avoiding the decomposition and inactivation of enzymes in the digestive intestine. Finally, the research on small molecules is quite mature in various aspects such as manufacturing process, dosage form design and routes of administration.

CONTENTS OF THE PRESENT INVENTION

The present disclosure provides an aromatic vinyl or aromatic ethyl derivative which is completely different from prior arts, a preparation method, an intermediate, a pharmaceutical composition and a use thereof. The aromatic vinyl or aromatic ethyl derivative of the present disclosure has a significant inhibitory effect on PD-1/PD-L1, is a kind of small molecular inhibitors with great effect on PD-1/PD-L1 and can alleviate or treat cancers and other related diseases.

The present disclosure provides an aromatic vinyl or aromatic ethyl derivative represented by general formula (I), a pharmaceutically acceptable salt, a metabolite, a metabolic precursor or a prodrug thereof:

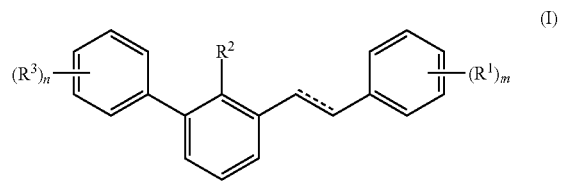

wherein,
 is a single bond or a double bond;
each of $R^1$ is identical or different, and is independently deuterium, halogen, substituted or unsubstituted hydroxyl, substituted or unsubstituted amino, substituted or unsubstituted alkyl, or substituted or unsubstituted alkoxy;
or two adjacent $R^1$ together with the two carbon atoms to which they are attached form a 5- to 7-membered carbocyclic ring or heterocarbocyclic ring; in the heterocarbocyclic ring, the heteroatom(s) is(are) oxygen and/or nitrogen, and the number of the heteroatom(s) is 1 to 4;
$R^2$ is substituted or unsubstituted alkyl or halogen;
each of $R^3$ is identical or different, and is independently deuterium, halogen, substituted or unsubstituted alkylthio, substituted or unsubstituted hydroxyl, substituted or unsubstituted amino, substituted or unsubstituted alkyl, substituted or unsubstituted alkoxy,

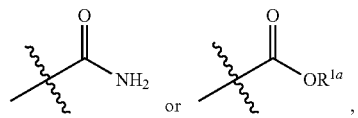

wherein $R^{1a}$ is $C_1$-$C_4$ alkyl, or two adjacent $R^3$ together with the two carbon atoms to which they are attached form a 5- to 7-membered carbocyclic ring or heterocarbocyclic ring;

in the heterocarbocyclic ring, the heteroatom(s) is(are) oxygen and/or nitrogen, and the number of the heteroatom(s) is 1 to 4;

in each of $R^1$ or $R^3$, the substituent(s) in the substituted alkyl, the substituted alkoxy or the substituted alkylthio is(are) one or more selected from halogen, $C_{1-4}$ alkyl, hydroxyl,

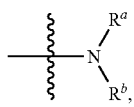

$C_{1-4}$ alkoxy, $C_{1-4}$ carboxyl, $C_{1-4}$ ester group and $C_{1-4}$ amide group; when there are more substituents than one, the substituents are identical or different; $R^a$ and $R^b$ are independently hydrogen, or, substituted or unsubstituted alkyl; in $R^a$ or $R^b$, the substituent(s) in the substituted alkyl is(are) one or more selected from halogen, $C_1$-$C_4$ alkyl, hydroxyl,

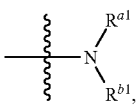

$C_1$-$C_4$ alkoxy, $C_1$-$C_4$ carboxyl, $C_1$-$C_4$ ester group and $C_1$-$C_4$ amide group; $R^{a1}$ and $R^{b1}$ are independently hydrogen or $C_1$-$C_4$ alkyl;

in each of $R^1$ or $R^3$, the substituent(s) in the substituted hydroxyl or the substituted amino is(are) one or more selected from $C_{1-4}$ alkyl, $C_{1-4}$ alkoxy, $C_{1-4}$ carboxyl, $C_{1-4}$ ester group and $C_{1-4}$ amide group;

m is 1, 2 or 3;

n is 0, 1, 2 or 3;

when === is a double bond and m is 2, then two $R^1$ are located on ortho and meta positions of the phenyl, respectively, such as

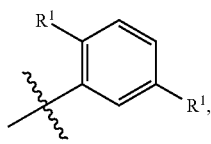

and the two $R^1$ are identical or different;

when === is a double bond and m is 3, then two of $R^1$ are adjacent, and the two adjacent $R^1$ together with the two carbon atoms to which they are attached form a 5- to 7-membered heterocarbocyclic ring;

the aromatic vinyl or aromatic ethyl derivative represented by general formula (I) excludes the compound as followed:

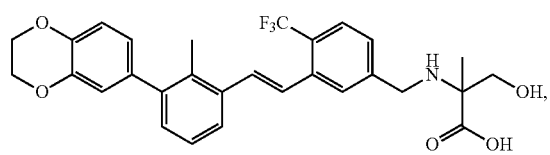

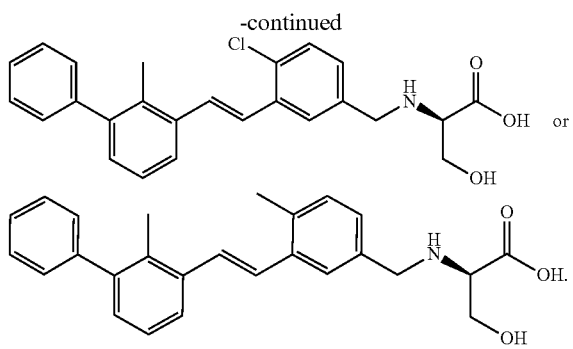

In one preferred embodiment of the present disclosure, each of $R^1$ is independently halogen, or, substituted or unsubstituted alkyl; or two adjacent $R^1$ together with the two carbon atoms to which they are attached form a 5- to 7-membered heterocarbocyclic ring.

In one preferred embodiment of the present disclosure, $R^2$ is alkyl or halogen.

In one preferred embodiment of the present disclosure, each of $R^3$ is independently halogen, alkylthio or alkoxy; or two adjacent $R^3$ together with the two carbon atoms to which they are attached form a 5- to 7-membered heterocarbocyclic ring.

In one preferred embodiment of the present disclosure, in each of $R^1$, the substituent(s) in the substituted alkyl is(are) one or more selected from halogen and

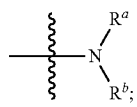

$R^a$ and $R^b$ are independently hydrogen, or, substituted or unsubstituted alkyl; in $R^a$ or $R^b$, the substituent(s) in the substituted alkyl is(are) one or more selected from hydroxyl and $C_1$-$C_4$ carboxyl.

In one preferred embodiment of the present disclosure, when two $R^3$ are adjacent, and the two adjacent $R^3$ together with the two carbon atoms to which they are attached form a 5- to 7-membered carbocyclic ring or heterocarbocyclic ring, then the carbocyclic ring or heterocarbocyclic ring can be further substituted by one or more than one $C_{1-4}$ alkyl (such as

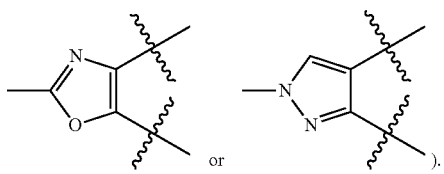

In one preferred embodiment of the present disclosure,

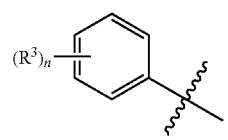

can be replaced by a substituted or unsubstituted heteroaromatic ring, in the heteroaromatic ring, the heteroatom(s) is(are) selected from nitrogen, oxygen and sulfur, and the number of the heteroatom(s) is 1 to 4; the substituent(s) in the substituted heteroaromatic ring is(are) one or more selected from halogen, $C_{1-4}$ alkyl, hydroxyl,

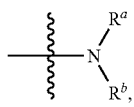

$C_{1-4}$ alkoxy, $C_{1-4}$ carboxyl, $C_{1-4}$ ester group and $C_{1-4}$ amide group; when there are more substituents than one, then the substituents are identical or different; $R^a$ and $R^b$ are independently hydrogen, or, substituted or unsubstituted alkyl; in $R^a$ or $R^b$, the substituent(s) in the substituted alkyl is(are) one or more selected from halogen, $C_1$-$C_4$ alkyl, hydroxyl,

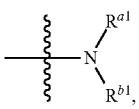

$C_1$-$C_4$ alkoxy, $C_1$-$C_4$ carboxyl, $C_1$-$C_4$ ester group and $C_1$-$C_4$ amide group; $R^{a1}$ and $R^{b1}$ are independently hydrogen or $C_1$-$C_4$ alkyl; the substituent(s) in the substituted heteroaromatic ring is(are) preferably selected from one or more than one $C_{1-4}$ alkyl.

In one preferred embodiment of the present disclosure, when

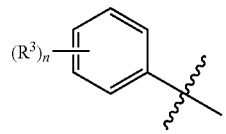

is replaced by a substituted or unsubstituted heteroaromatic ring, then in the heteroaromatic ring, the heteroatom(s) is(are) selected from nitrogen and oxygen, and the number of the heteroatom(s) is 1 to 3. Further preferably, when the heteroaromatic ring is a monocyclic ring, then the heteroatom(s) is(are) nitrogen, and the number of the heteroatom(s) is 1 or 2; when the heteroaromatic ring is a dicyclic heteroaromatic ring and the heteroatom(s) is(are) nitrogen, then the number of the heteroatom(s) is preferably 3; when the heteroaromatic ring is a dicyclic heteroaromatic ring, the heteroatom(s) is(are) selected from nitrogen and oxygen and the number of the heteroatoms is 2, then the heteroatoms are not adjacent.

In one preferred embodiment of the present disclosure, n is 0, 1, 2 or 3. When n is 1, then $R^3$ is preferably halogen, alkylthio or alkoxy; and $R^3$ is located on ortho, meta or para position of the phenyl, such as

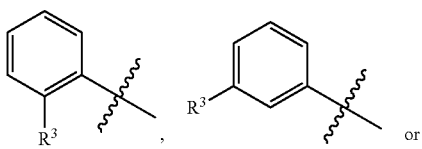

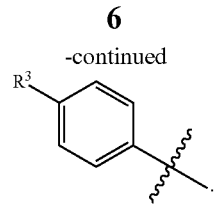

When n is 2, then preferably, two $R^3$ are located on ortho and meta positions of the phenyl, such as

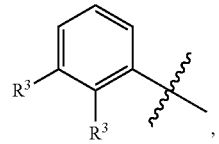

wherein, the two $R^3$ are identical or different; or two $R^3$ are adjacent, and the two adjacent $R^3$ together with the two carbon atoms to which they are attached form a 5- to 7-membered heterocarbocyclic ring, such as

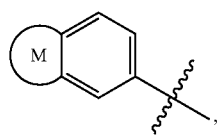

wherein, ring M is a 5- to 7-membered heterocarbocyclic ring. When n is 3, then preferably, two of $R^3$ are adjacent, and the two adjacent $R^3$ and two carbon atoms connected to them form a 5- to 7-membered heterocarbocyclic ring, such as

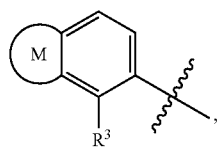

wherein, ring M is a 5- to 7-membered heterocarbocyclic ring (such as 2,3-dihydro-1,4-dioxane

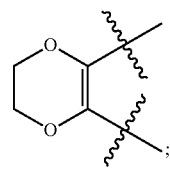 [SMILES: *C1=C(*)OCCO1]

oxazole ring, such as

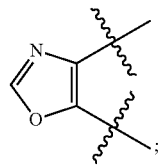 [SMILES: *c1ncoc1*]

isoxazole ring, such as

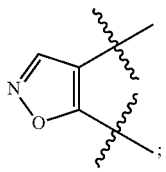

pyrazole ring, such as

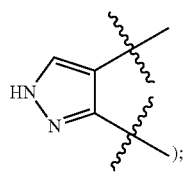

ring M can be further substituted by one or more than one $C_{1-4}$ alkyl (such as

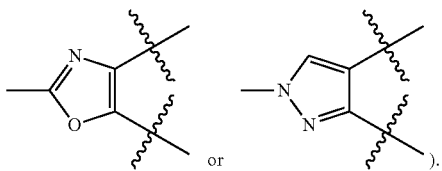

In one preferred embodiment of the present disclosure, m is 2 or 3. When m is 2, then two $R^1$ are preferably located on ortho and para positions of the phenyl, respectively, such as

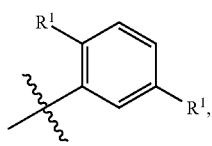

and the two $R^1$ are identical or different. When m is 3, then preferably, two of $R^1$ are adjacent, and the two adjacent $R^1$ together with the two carbon atoms to which they are attached form a 5- to 7-membered heterocarbocyclic ring, such as

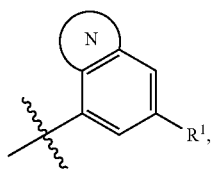

wherein, ring N is a 5- to 7-membered heterocarbocyclic ring, such as 2,3-dihydrofuran ring

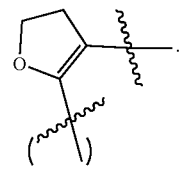

In one preferred embodiment of the present disclosure, when m is 2, then one of $R^1$ (preferably located on ortho position of the phenyl) is preferably alkyl or alkyl substituted by halogen; the other of $R^1$ (preferably located on meta position of the phenyl) is preferably alkyl substituted by

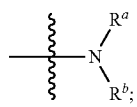

when m is 3, then two of $R^1$ are adjacent, and the two adjacent $R^1$ together with the two carbon atoms to which they are attached form a 5- to 7-membered heterocarbocyclic ring, and the third $R^1$ is alkyl substituted by

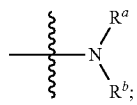

wherein, the alkyl is preferably $C_{1-4}$ alkyl. The alkyl substituted by halogen is preferably $C_1$-$C_4$ alkyl substituted by one or more halogen, such as trifluoromethyl. The alkyl substituted by

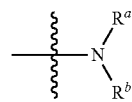

is preferably $C_1$-$C_4$ alkyl substituted by

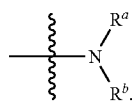

In one preferred embodiment of the present disclosure, the $C_1$-$C_4$ alkyl substituted by

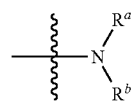

is preferably

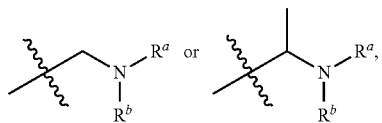

wherein, one of $R^a$ and $R^b$ is H, and the other is alkyl substituted by hydroxyl and/or carboxyl.

In one preferred embodiment of the present disclosure, the $C_1$-$C_4$ alkyl substituted by

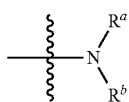

is preferably

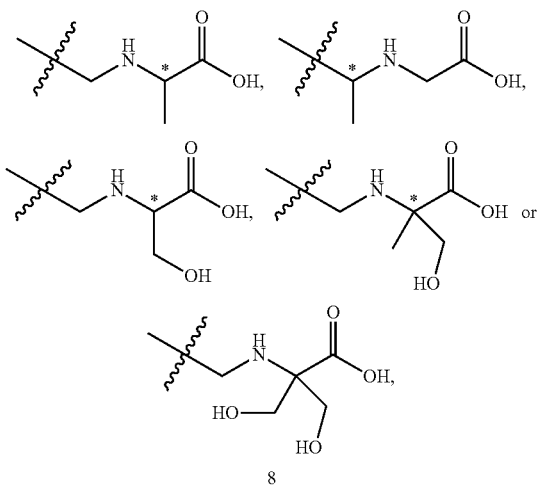

wherein, the carbon labelled by * is an S-configuration chiral carbon, an R-configuration chiral carbon or an achiral carbon. Wherein,

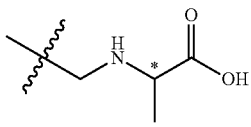 [SMILES: *CNC(C)C(=O)O]

is preferably

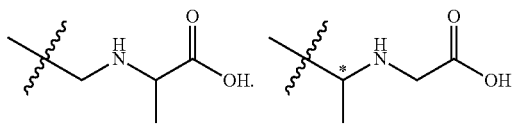

is preferably

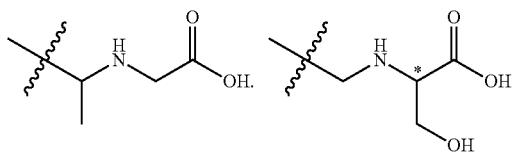

is preferably

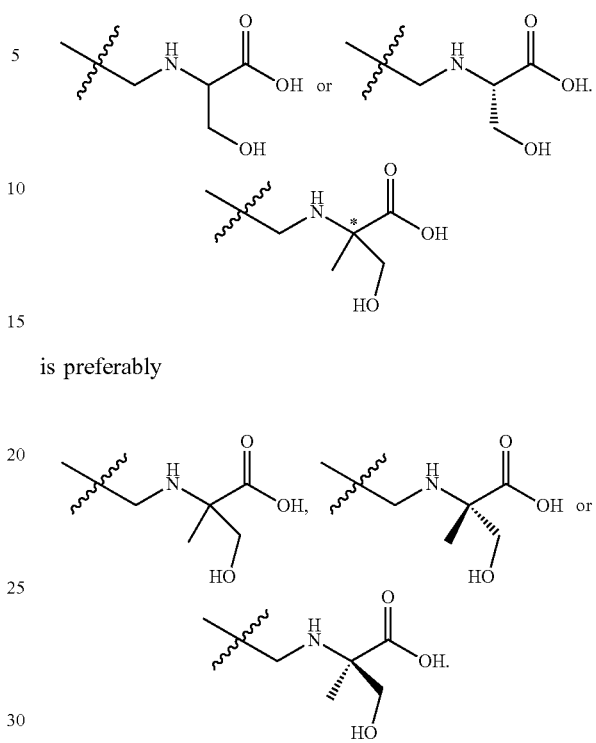

is preferably

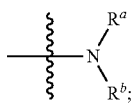

In one preferred embodiment of the present disclosure,
each of $R^1$ is independently halogen, or, substituted or unsubstituted alkyl; or two adjacent $R^1$ together with the two carbon atoms to which they are attached form a 5- to 7-membered heterocarbocyclic ring;
$R^2$ is alkyl or halogen;
each of $R^3$ is independently H, halogen, alkylthio, or alkoxy; or two adjacent $R^3$ together with the two carbon atoms to which they are attached form a 5- to 7-membered heterocarbocyclic ring;
n is 0, 1, 2 or 3;
and m is 2.

In one preferred embodiment of the present disclosure,
each of $R^1$ is independently H, or, substituted or unsubstituted alkyl; or two adjacent $R^1$ together with the two carbon atoms to which they are attached form a 5- to 7-membered heterocarbocyclic ring; the substituent(s) in the substituted alkyl is(are) one or more selected from halogen and

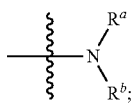

$R^a$ and $R^b$ are independently hydrogen, or, substituted or unsubstituted alkyl; in $R^a$ or $R^b$, the substituent(s) in the substituted alkyl is(are) one or more selected from hydroxyl and $C_1$-$C_4$ carboxyl;
$R^2$ is alkyl or halogen;
each of $R^3$ is independently H, halogen, alkylthio or alkoxy; or two adjacent $R^3$ together with the two carbon atoms to which they are attached form a 5- to 7-membered heterocarbocyclic ring;

n is 0, 1, 2 or 3; when n is 1, then $R^3$ is preferably halogen, alkylthio or alkoxy; and $R^3$ is located on ortho, meta or para position of the phenyl, such as

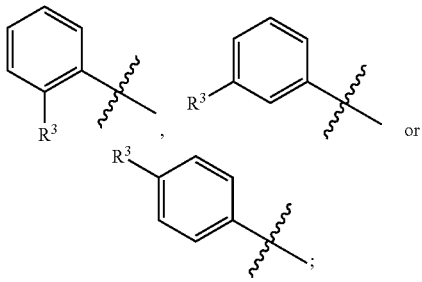

when n is 2, then preferably, two $R^3$ are located on ortho and meta positions of the phenyl, such as

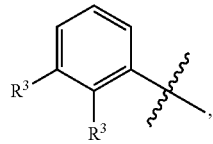

wherein, the two $R^3$ are identical or different; or two $R^3$ are adjacent, and the two adjacent $R^3$ together with the two carbon atoms to which they are attached form a 5- to 7-membered heterocarbocyclic ring, such as

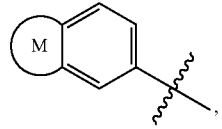

wherein, ring M is a 5- to 7-membered heterocarbocyclic ring; when n is 3, then preferably, one of $R^3$ is halogen, the other two $R^3$ are adjacent, and the two adjacent $R^3$ together with the two carbon atoms to which they are attached form a 5- to 7-membered heterocarbocyclic ring, such as

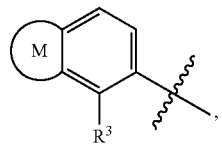

wherein, ring M is a 5- to 7-membered heterocarbocyclic ring;

and m is 2 or 3; when m is 2, then two $R^1$ are preferably located on ortho and para positions of the phenyl, respectively, such as

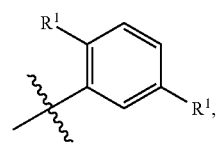

$R^1$ located on ortho position of the phenyl is alkyl or alkyl substituted by halogen; $R^1$ located on meta position of the phenyl is alkyl substituted by

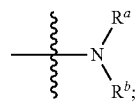

when m is 3, then two of $R^1$ are adjacent, and the two adjacent $R^1$ together with the two carbon atoms to which they are attached form a 5- to 7-membered heterocarbocyclic ring, and the third $R^1$ is alkyl substituted by

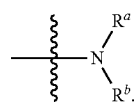

In one preferred embodiment of the present disclosure,

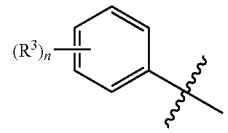

is preferably

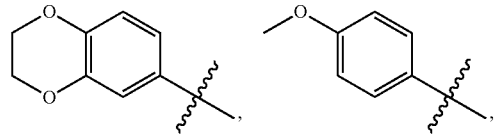

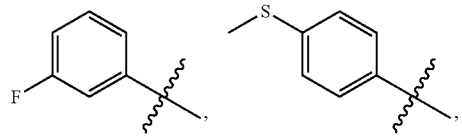

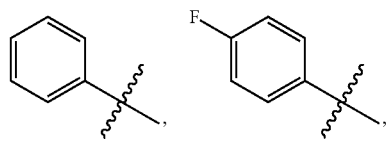

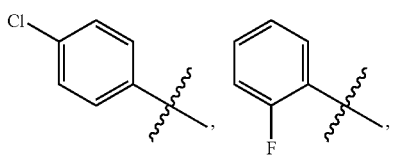

-continued
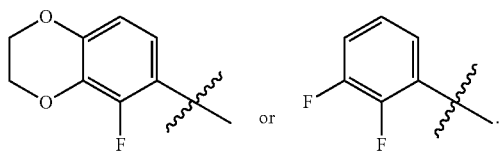
or
In one preferred embodiment of the present disclosure,
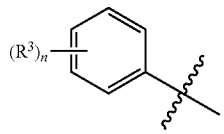
is preferably
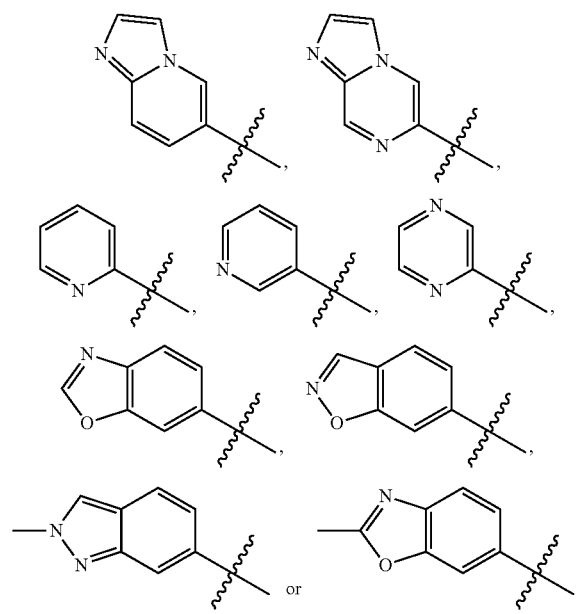
or
In one preferred embodiment of the present disclosure,
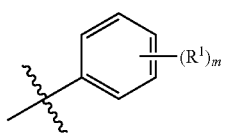
is preferably
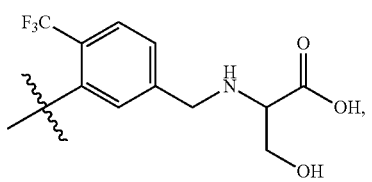
-continued
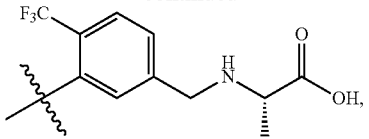
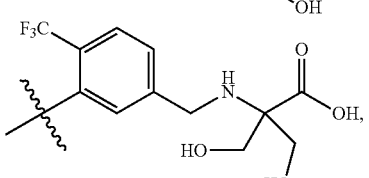
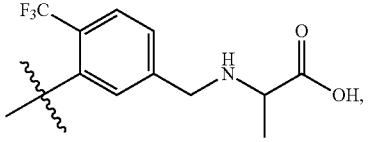
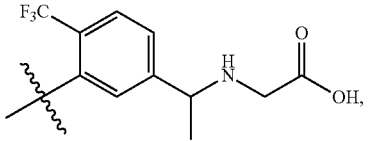
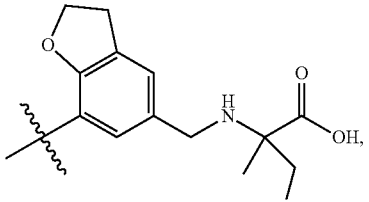
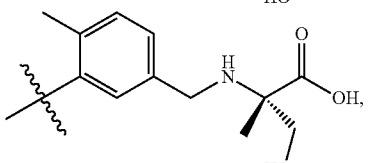
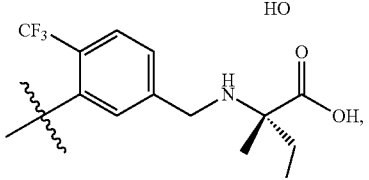
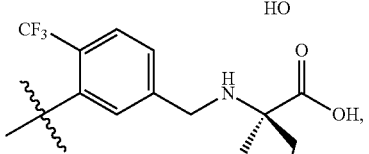
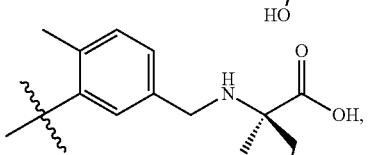
or

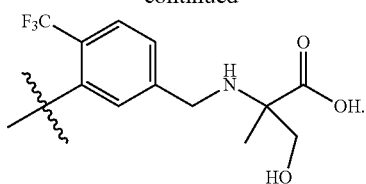

In one preferred embodiment of the present disclosure, when n is 1, $R^3$ is halogen or alkoxy, and $R^3$ is located on para position of the phenyl, then m is 2 or 3; when m is 2, then $R^1$ located on ortho position of the phenyl is alkyl substituted by halogen.

In one preferred embodiment of the present disclosure, when n is 1 and $R^3$ is halogen, then $R^3$ is preferably F or Cl. When $R^3$ is F, then $R^3$ is preferably located on meta position of the phenyl.

In one preferred embodiment of the present disclosure, in the aromatic vinyl or aromatic ethyl derivative represented by general formula (I), the pharmaceutically acceptable salt, the metabolite, the metabolic precursor or the prodrug thereof,

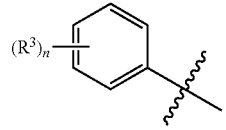

can be replaced by a substituted or unsubstituted heteroaromatic ring, and other variables and substituents are as defined above.

In the present disclosure, the aromatic vinyl or aromatic ethyl derivative represented by general formula (I) is preferably any one of the compounds as followed:

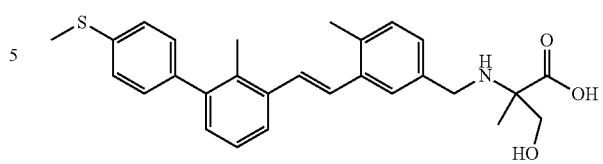
1

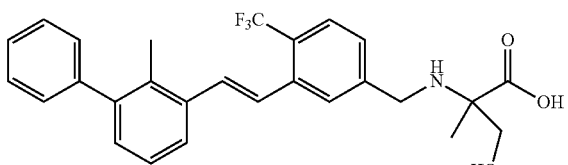
2

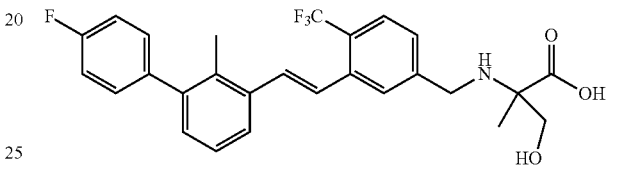
3

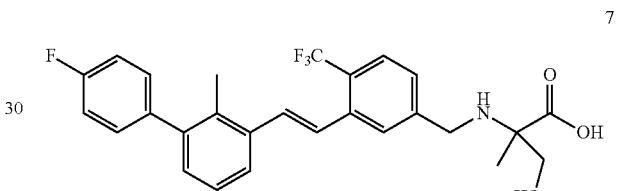
4

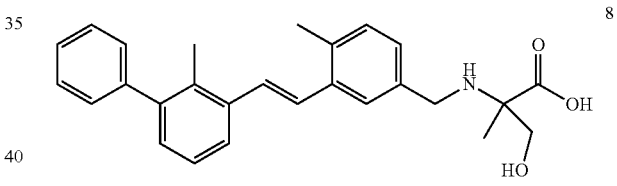
5

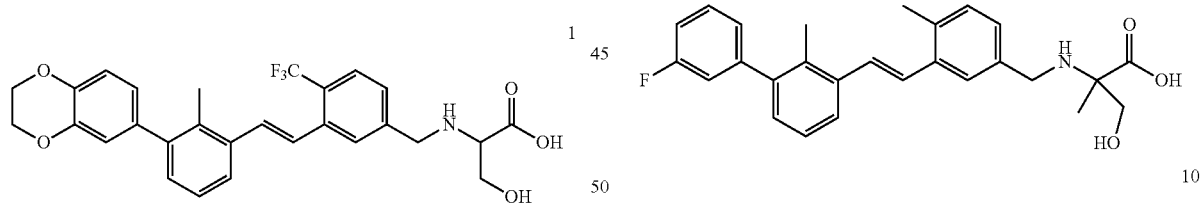
6

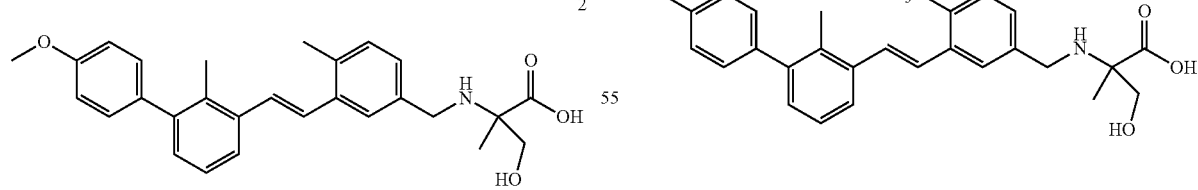
7

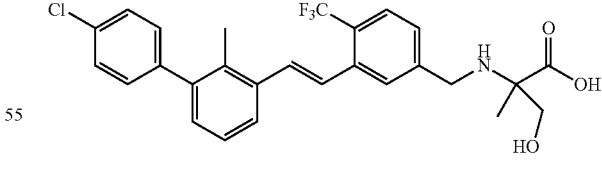
8

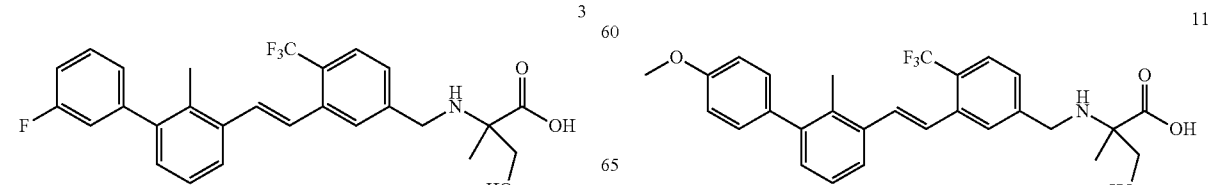
9

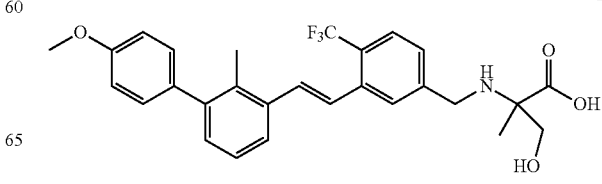
10

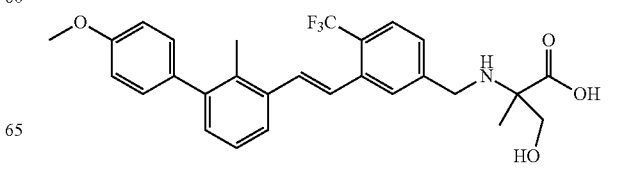
11

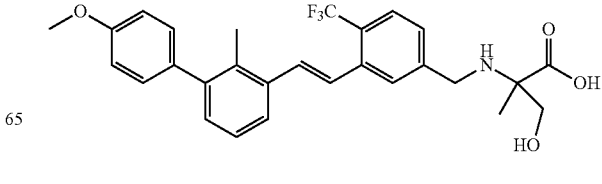

12
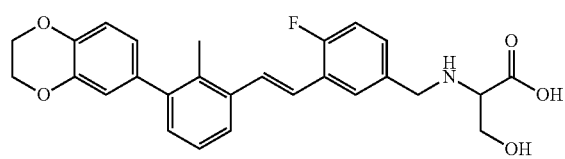
13
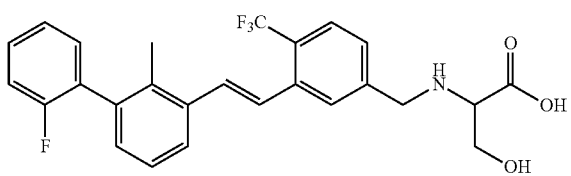
14
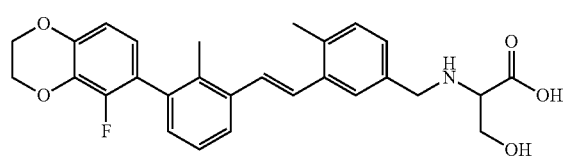
15
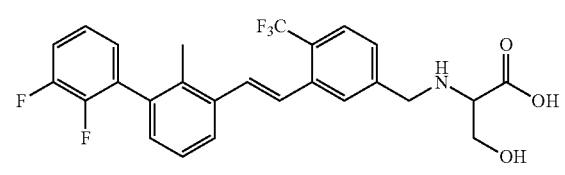
16
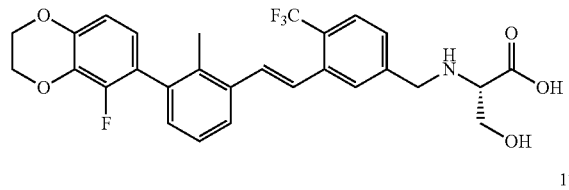
17
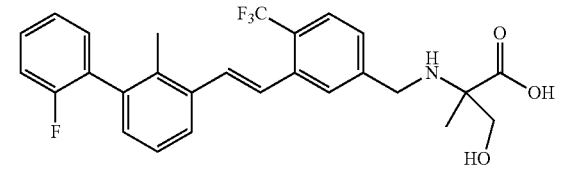
18
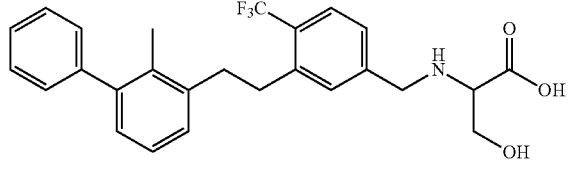
19
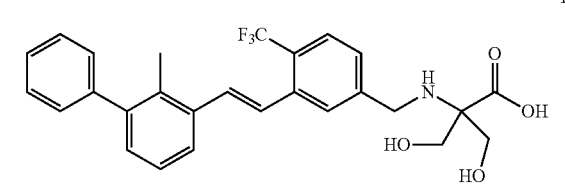
20
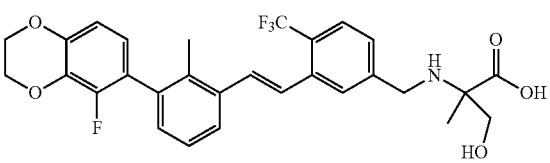
21
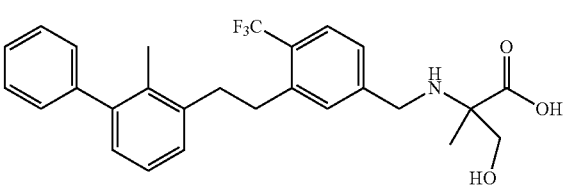
22
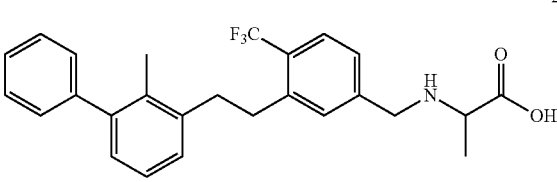
23
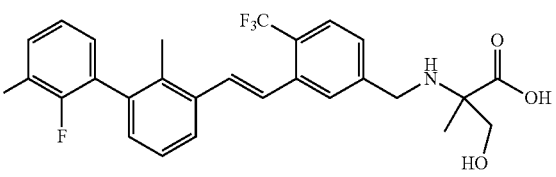
24
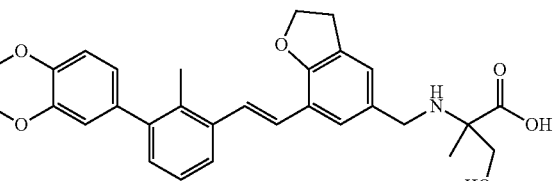
25
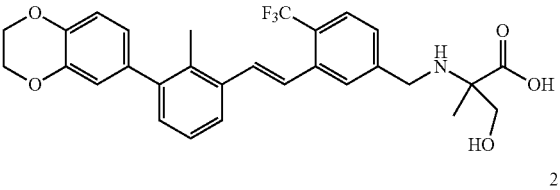
26
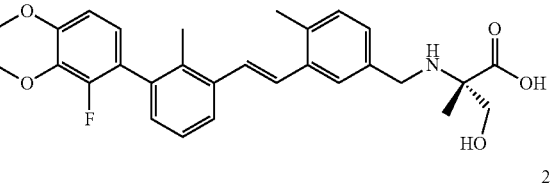
27
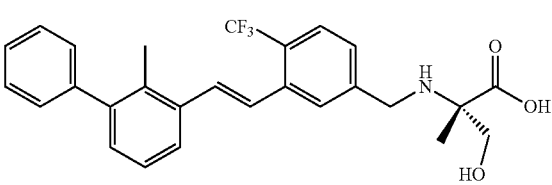

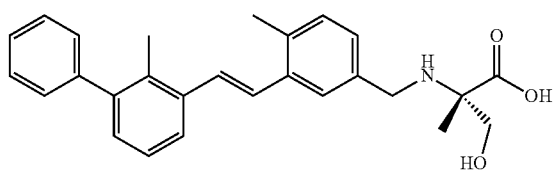
28
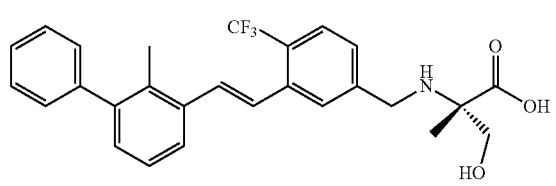
29
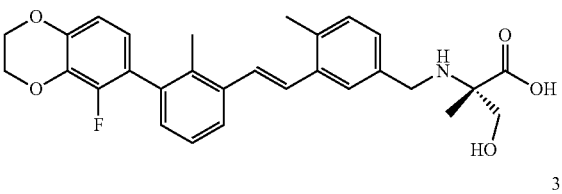
30
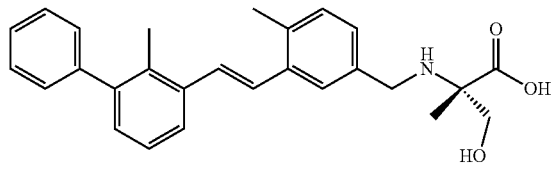
31
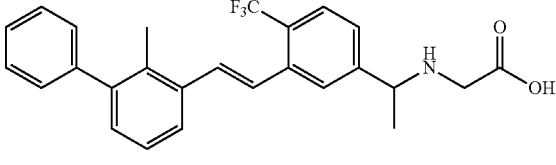
32
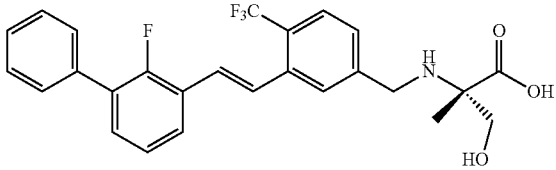
33
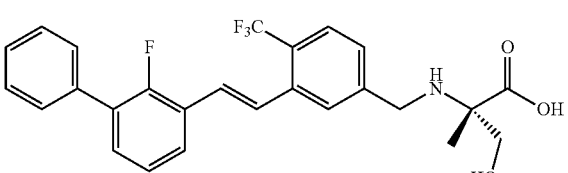
34
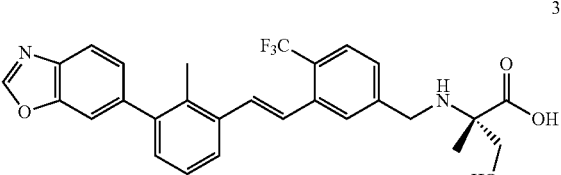
35
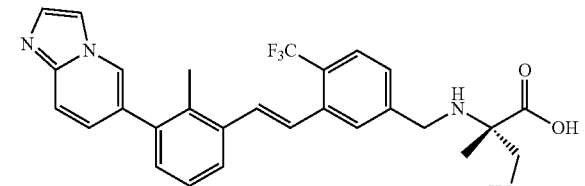
36
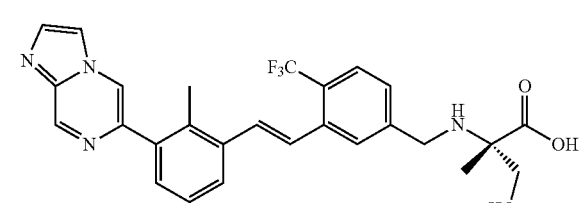
37
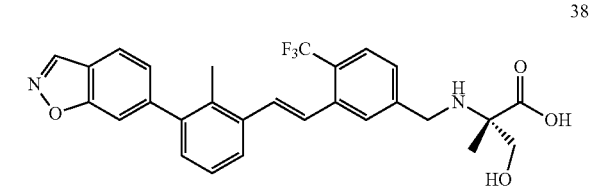
38
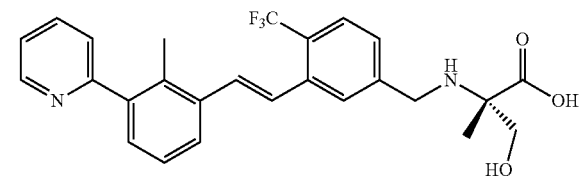
39
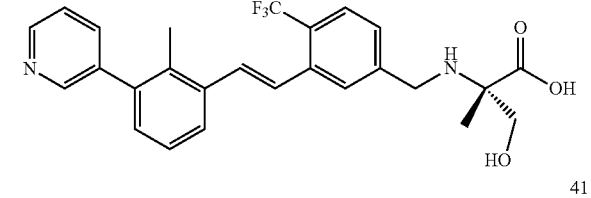
40
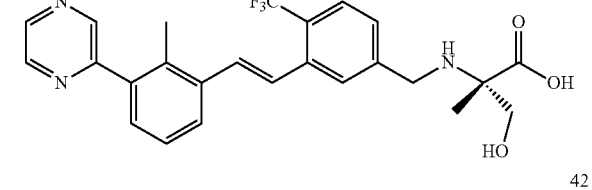
41
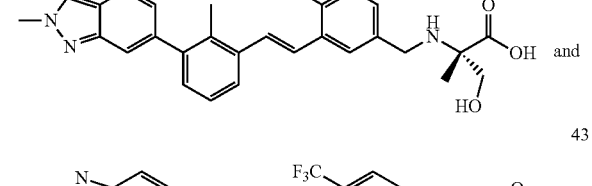
42 and
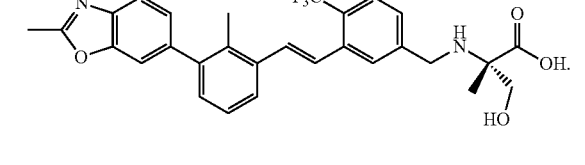
43

In one preferred embodiment of the present disclosure, the aromatic vinyl or aromatic ethyl derivative represented by general formula (I) is preferable an aromatic vinyl or aromatic ethyl derivative represented by general formula (II)

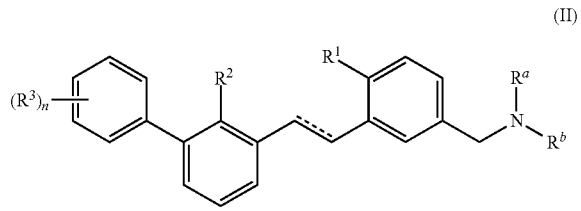

wherein, the definitions of $R^1$, $R^2$, $R^3$, n, $R^a$ and $R^b$ are as defined above.

The present disclosure further provides a method for preparing the aromatic vinyl or aromatic ethyl derivative represented by general formula (II), which comprises the following step: conducting a reductive amination reaction of compound (I-a) with

as followed to obtain the compound represented by general formula (II);

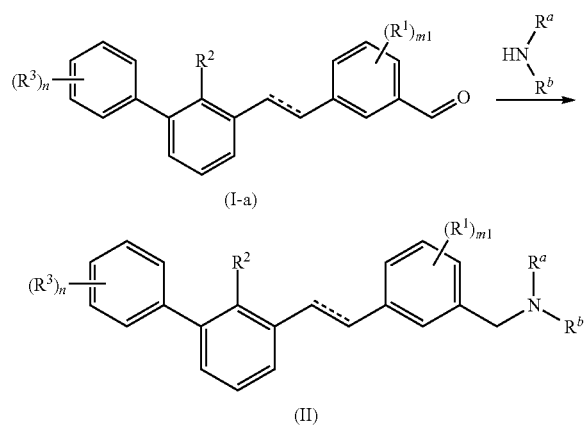

in the general formulae above, the definitions of $R^1$, $R^2$, $R^3$, n, $R^a$ and $R^b$ are as defined above, and m1 is 0, 1 or 2. The methods and conditions of the reductive amination reaction are conventional methods and conditions for such reactions in the art.

An acid can be added in the reductive amination reaction. The acid is preferable an inorganic acid and/or an organic acid. The inorganic acid is preferable hydrochloric acid and/or sulfuric acid. The organic acid is preferable acetic acid. The molar ratio of the acid to the compound (I-a) is preferably 0.2:1 to 5:1 (such as 2:1).

The solvent is preferably an organic solvent and/or water. The organic solvent can be an organic solvent commonly used in such reactions in the art, preferably one or more selected from an alcohol solvent, an chlorinated hydrocarbon solvent, an ether solvent and an amide solvent. The alcohol solvent is preferably methanol and/or ethanol. The chlorinated hydrocarbon solvent is preferably dichloromethane. The ether solvent is preferably 1,4-dioxane. The amide solvent is preferably N,N-dimethylformamide. The solvent is preferably a mixed solvent of an alcohol solvent and a chlorinated hydrocarbon solvent, such as a mixed solvent of methanol and dichloromethane. In the mixed solvent of the alcohol solvent and the chlorinated hydrocarbon solvent, the volume ratio of the alcohol solvent to the chlorinated hydrocarbon solvent is preferably 1:0.1 to 1:5 (such as 1:1). The amount of the solvent can not be specifically limited as long as it does not affect the progress of the reaction, the volume-to-mass ratio of the solvent to the compound represented by compound (I-a) is preferably 10 mL/g to 200 mL/g.

The reductant can be a reductant commonly used in such reactions in the art, preferably one or more selected from sodium cyanoborohydride, sodium acetate borohydride, sodium borohydride and lithium borohydride, and preferably sodium cyanoborohydride. The molar ratio of the reductant to the compound (I-a) is preferably 0.3:1 to 10:1 (such as 5:1).

In the reductive amination reaction, the molar ratio of the compound (I-a) to

is 1:1 to 1:3 (such as 1:2).

The temperature of the reductive amination reaction is preferably 0° C. to 120° C., more preferably 0° C. to 50° C., further more preferably room temperature (10° C. to 30° C.).

The progress of the reductive amination reaction can be monitored by TLC or HPLC, generally the disappearance of the compound (I-a) is seen as completion of the reaction.

After the completion of the reductive amination reaction, the product can be further purified by a post-treatment. The methods of the post-treatment preferably comprises one or more methods selected from recrystallization, silica gel thin layer chromatography preparative plate purification (such as dichloromethane:methanol=15:1), silica gel column chromatography purification and preparative high performance liquid chromatography purification (mobile phase: water (10 mM ammonium bicarbonate) and acetonitrile; the gradient: 25% to 55%).

A method for preparing the compound (I-a) preferably comprises the following step: in a solvent, in the action of a palladium catalyst, conducting a coupling reaction of compound (II-b) with

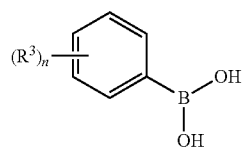

to obtain the compound (I-a);

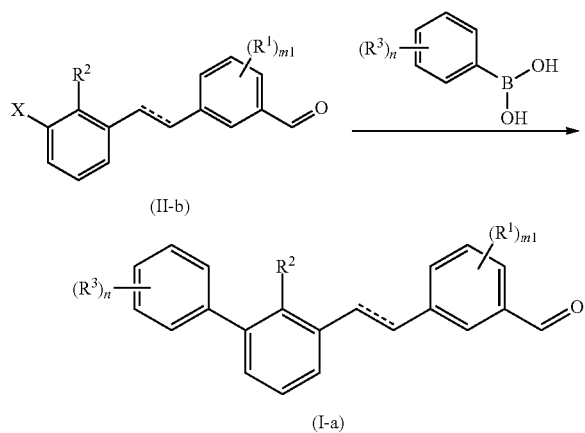

wherein the definitions of $R^1$, $R^2$, $R^3$, n, $R^a$ and $R^b$ are as defined above, X is halogen, m1 is 0, 1 or 2.

The methods and conditions of the coupling reaction are conventional methods and conditions for such reactions in the art.

In the method for preparing the compound (I-a), a base can also be added in the coupling reaction. The base is preferably an alkali metal carbonate, more preferably sodium carbonate, potassium carbonate or cesium carbonate. The molar ratio of the base to the compound (II-b) is preferably 1:1 to 5:1.

In the method for preparing the compound (I-a), the solvent is preferably an organic solvent and/or water. The organic solvent can be an organic solvent commonly used in such reactions in the art, preferably one or more selected from an ether solvent, an aromatic hydrocarbon solvent and an amide solvent. The ether solvent is preferably 1,4-dioxane and dimethoxyethane. The aromatic hydrocarbon solvent is preferably toluene. The amide solvent is preferably N,N-dimethylformamide The solvent is preferably an aromatic hydrocarbon solvent. The volume-to-mass ratio of the solvent and the compound (II-b) is preferably 10 mL/g to 110 mL/g.

In the method for preparing the compound (I-a), the palladium catalyst can be a palladium catalyst commonly used in such coupling reactions, preferably selected from [1,1'-bis(diphenylphosphino)ferrocene] palladium dichloride, tris(dibenzylideneacetone)dipalladium, palladium acetate and tetrakis(triphenylphosphine)palladium. The molar ratio of the palladium catalyst to the compound (II-b) is preferably 0.005:1 to 0.5:1, more preferably 0.01:1 to 0.10:1.

In the method for preparing the compound (I-a), the coupling reaction is preferably carried out in the presence of a ligand, and the ligand is preferably 2-dicyclohexylphosphino-2',4',6'-triisopropylbiphenyl.

In the method for preparing the compound (I-a), the temperature of the coupling reaction is preferably 50° C. to 150° C. (such as 80° C. to 90° C.).

In the method for preparing the compound (I-a), the progress of the coupling reaction can be monitored by TLC or HPLC, generally the disappearance of the compound (II-b) is seen as completion of the reaction.

In the method for preparing the compound (I-a), after the completion of the coupling reaction, the product can be further purified by a post-treatment. The methods of the post-treatment preferably comprises one or more methods selected from recrystallization, silica gel thin layer chromatography preparative plate purification (eluent=petroleum ether:ethyl acetate), silica gel column chromatography purification and preparative high performance liquid chromatography purification.

Those skilled in the art should understand that, after knowing the structure of the compounds of the present disclosure, the compounds of the present disclosure can be obtained by various methods well-known in the art and using well-known raw materials, such as chemical synthesis or extraction from plants, and these methods are included in the present disclosure. Unless otherwise stated or provided a preparation method, the raw materials used to prepare the compounds of the present disclosure or intermediates thereof are known in the art or are commercially available.

The present disclosure further provides a compound (I-a):

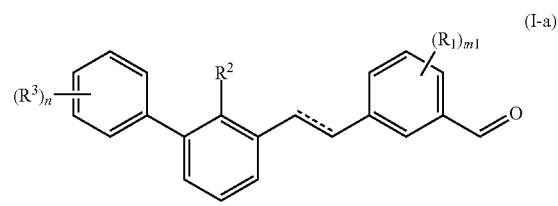

wherein, the definitions of $R^1$, $R^2$, $R^3$ and n are as defined above, and m1 is 0, 1 or 2; and

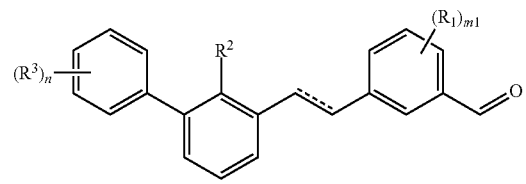

is not

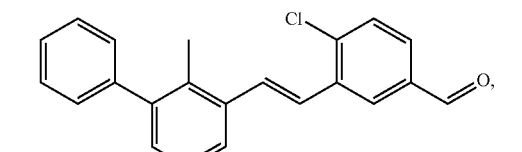

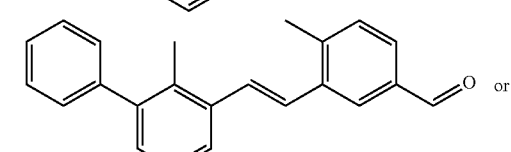

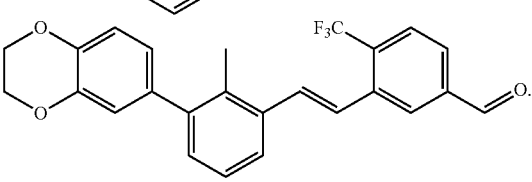

The compound (I-a) is preferably any one of the compounds as followed:

-continued
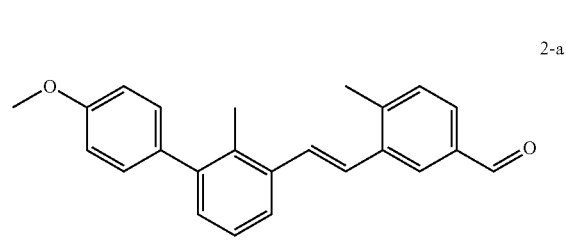
2-a
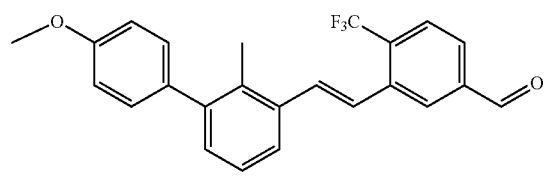
11-a
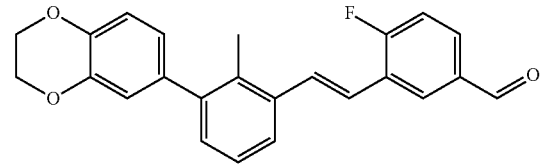
12-a
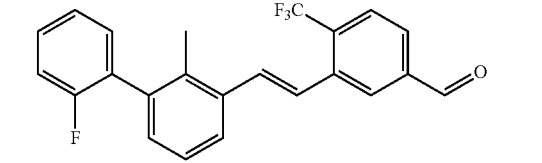
13-a
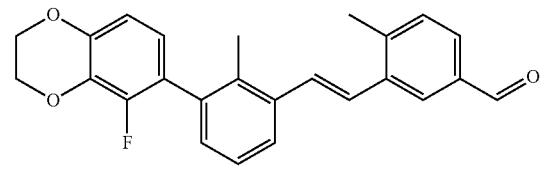
14-a
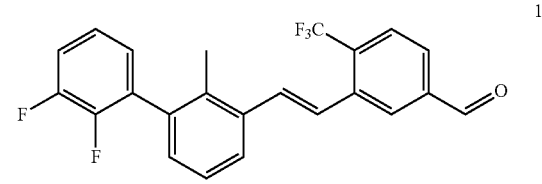
15-a
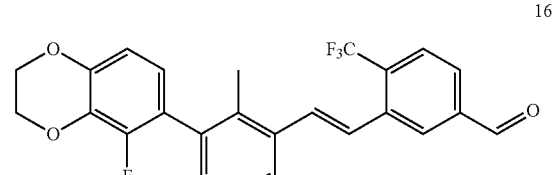
16-a
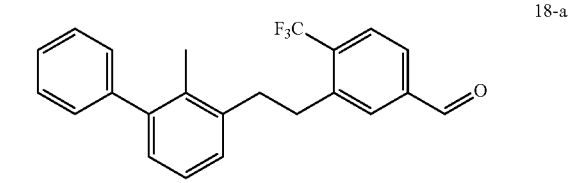
18-a
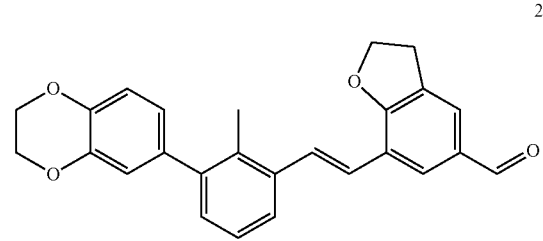
24-a -continued 33-a
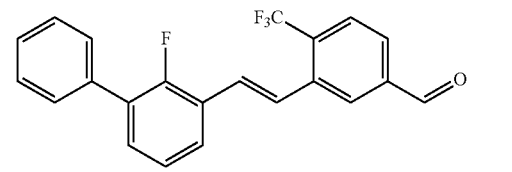

35-a
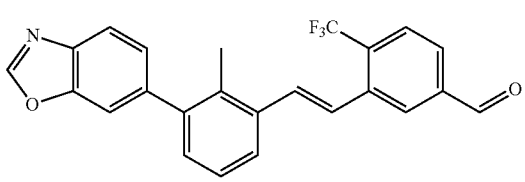

36-a
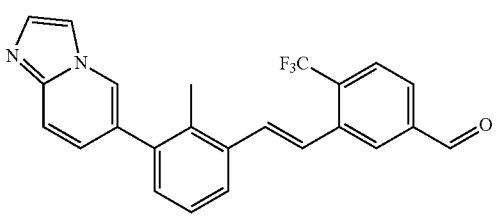

37-a
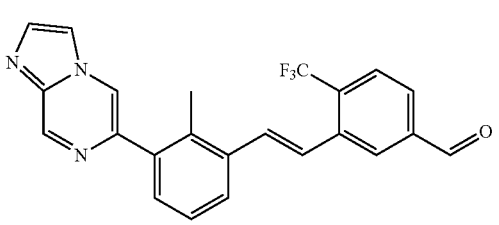

38-a
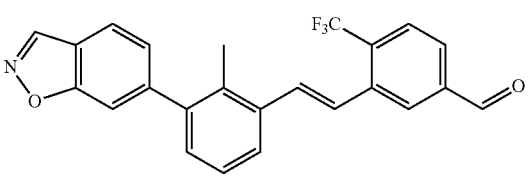

39-a
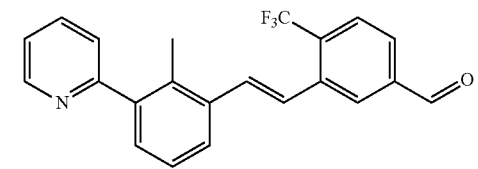

40-a
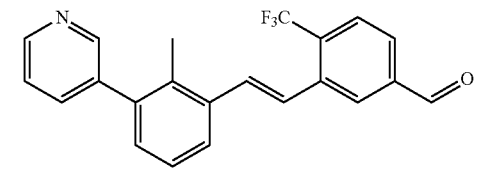

41-a
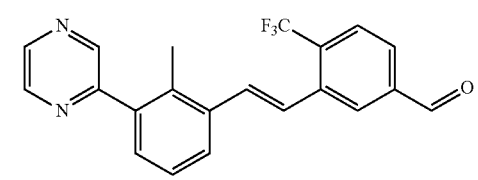

-continued 42-a
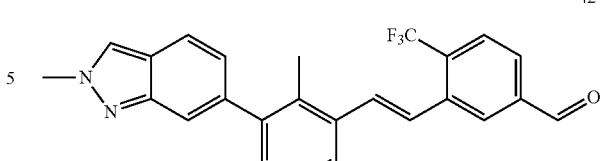

43-c
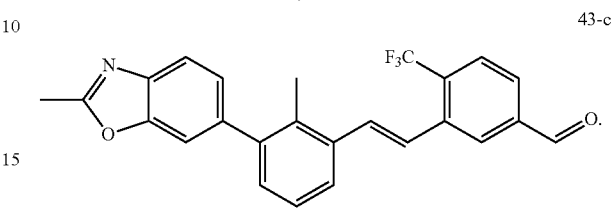

The present disclosure further provides a use of the aromatic vinyl or aromatic ethyl derivative represented by general formula (I), the pharmaceutically acceptable salt, the metabolite, the metabolic precursor or the prodrug thereof in manufacturing PD-1 inhibitors and/or PD-L1 inhibitors.

The present disclosure further provides a use of the aromatic vinyl or aromatic ethyl derivative represented by general formula (I), the pharmaceutically acceptable salt, the metabolite, the metabolic precursor or the prodrug thereof in manufacturing a medicament for preventing, alleviating or treating cancer, infection, autoimmune diseases or the related diseases thereof.

The cancer is preferably one or more selected from lung cancer, esophageal cancer, stomach cancer, colorectal cancer, liver cancer, nasopharyngeal cancer, brain tumor, breast cancer, cervical cancer, blood cancer and bone cancer.

The present disclosure also provides a pharmaceutical composition, which comprises a therapeutically and/or prophylactically effective amount of the aromatic vinyl or aromatic ethyl derivative represented by general formula (I), the pharmaceutically acceptable salt, the metabolite, the metabolic precursor or the prodrug thereof, and a pharmaceutically acceptable carrier and/or a diluent.

In the present disclosure, the pharmaceutical composition can be formulated into various types of dosage forms such as tablets, pills, powders, liquids, suspensions, emulsions, granules, capsules, suppositories and injections (solutions and suspensions) etc., preferably liquids, suspensions, emulsions, suppositories and injections (solutions and suspensions) etc.

In order to form a pharmaceutical composition in the form of a tablet, any known and widely used excipients in the art can be used. For example, carriers such as lactose, white sugar, sodium chloride, glucose, urea, starch, calcium carbonate, kaolin, crystalline cellulose and silicic acid and the like; adhesives such as water, ethanol, propanol, common syrup, dextrose solution, starch solution, gelatin solution, carboxymethylcellulose, shellac, methylcellulose and potassium phosphate, polyvinylpyrrolidone and the like; disintegrats such as dry starch, sodium alginate, agar powder and kelp powder, sodium bicarbonate, calcium carbonate, polyethylene sorbitan fatty acid ester, sodium dodecyl sulfate, stearic acid monoglyceride, starch and lactose and the like; disintegration inhibitors such as white sugar, glyceryl tristearate, coconut oil and hydrogenated oil; adsorption accelerators such as quaternary ammonium base and sodium dodecyl sulfate; wetting agents such as glycerol, starch and the like; adsorbents such as starch, lactose, kaolin, bentonite and colloidal silicic acid and the like; and lubricants such as pure talc, stearate, boric acid powder and polyethylene glycol. It is also possible to use conventional coating materials to prepare sugar-coated tablets, gelatin membrane-coated tablets, enteric-coated tablets, film-coated tablets, bilayer tablets and multilayered tablets.

In order to form the pharmaceutical composition in the form of a pill, any known and widely used excipients in the art can be used, for example, carriers such as lactose, starch, coconut oil, hardened vegetable oil, kaolin and talc and the like, adhesives such as gum arabic, gum tragacanth, gelatin and ethanol and the like; disintegrating agents such as agar and kelp powder and the like.

In order to form the pharmaceutical composition in the form of a suppository, any of the known and widely used excipients in the art can be used, for example, polyethylene glycol, coconut oil, higher alcohols, esters of higher alcohols, gelatin and semi-synthetic glycerides, etc.

In order to prepare a pharmaceutical composition in the form of an injection, the solution or suspension can be sterilized (preferably by adding an appropriate amount of sodium chloride, glucose or glycerol, etc.) to form an injection with the isotonic pressure of the blood. Any suitable carrier in the art can also be used in the preparation of the injection. For example, water, ethanol, propanediol, ethoxylated isostearyl alcohol, polyoxylated isostearyl alcohol and polyethylene sorbitan fatty acid ester. In addition, ordinary solubilizers, buffers and analgesics can be added.

In the pharmaceutical composition, the diluent can be a conventional diluent in the art.

The pharmaceutical composition can be in the form of oral or a sterile injectable aqueous solution. And oral and injectable composition can be prepared according to any method known in the art for preparing a pharmaceutical composition.

The term "therapeutically effective amount" refers to an amount of the compound administered to a subject sufficient to treat the diseases involved in the present disclosure. Though a therapeutically effective amount of a compound will vary depending on the compound, the condition and its severity, and the age of the subject to be treated, it can be determined by a person skilled in the art according to the common method.

As used in the present disclosure, when the specific salt, pharmaceutical composition, composition, excipient are mentioned to be "pharmaceutically acceptable", it means that the salt, pharmaceutical composition, composition, excipient are generally non-toxic, safe and suitable to be administered to the subject; the subject is preferably a mammal, more preferably human.

The term "pharmaceutically acceptable salt" as used herein refers to a pharmaceutically acceptable organic or inorganic salt of the compound of the present disclosure. Typical examples are include but not limited to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisate, fumarate, gluconate, glucuronate, saccharate, formate, benzoate, glutamate, methylsulfonate, ethylsulfonate, benzene sulfonate, tosilate, embonate (i.e. 1-1-methylene-bis(2-hydroxyl-3-naphthoate)).

The term "prodrug" used herein refers to a derivative of a compound containing biological reactive functional groups, which can be cleaved from the compound or react in other ways to provide the compound under biological condition (in vivo or in vitro). Generally, the prodrug does not have activity, or have less activity than the compound itself, this makes the compound exhibit effects until the biological reactive functional group cleaved from the compound. The biological reactive functional group can hydrolyze or oxidize under biological condition to provide the compound. For example, the prodrug can include biologically hydrolysable groups. The biologically hydrolysable groups include but not limited to a biologically hydrolysable phosphate, a biologically hydrolysable ester, a biologically hydrolysable amide, a biologically hydrolysable carbonate, a biologically hydrolysable carbamate and a biologically hydrolysable ureide.

The compound of the present disclosure can contain one or more asymmetric centers ("stereoisomers"). As used herein, the term "stereoisomer" refers to Cis- and Trans-isomer, R- and S-enantiomer and diastereomer. These stereoisomers can be prepared by methods of asymmetric synthesis or chiral separation (e.g. separation, crystallization, thin layer chromatography, column chromatography, gas chromatography, high performance liquid chromatography). These stereoisomers can also be derived from a diastereomer obtained by reacting a mixture of the enantiomers or racemates with a proper chiral compound, followed by crystallizing or any other proper common method.

As used herein, the term "subject" refers to any animal to be administered or has been administered with the compound or the pharmaceutical composition according to the example of the present disclosure, preferably a mammal, most preferably human. As used herein, the term "mammal" includes any mammal Typical mammal includes but not limited to cattle, horse, sheep, pig, cat, dog, mouse, rat, rabbit, Guinea pig, monkey, human and so on, the most preferable human In one embodiment, "treat" or "treating" refers to an improvement, prevention or reversion of a disease or a condition or at least one distinguished symptom thereof. In another example, "treat" or "treating" refers to an improvement, prevention or reversion of at least one of measurable body parameters of a disease or a condition which is being treated, which cannot have been distinguished in a mammal. However, in another example, "treat" or "treating" refers to slowing the development of a disease or a condition, or refers to stabilizing in body, such as a recognizable symptom, or refers to stabilizing in physiology, such as body parameters, or refers to both. In another embodiment, treat" or "treating" refers to slowing the initiation of a disease or a condition.

In certain embodiments, the compound of the present disclosure is administered for prevention. As used herein, "prevent" or "preventing" refers to lowering a risk of having a disease or a condition. In a preferred example, administering an indicated compound to a subject for a preventive purpose, such as the subject having a tendency to catch or having a family history of cancer or autoimmune diseases.

In the present disclosure, the term "halogen" is preferably F, Cl, Br or I.

In the present disclosure, the term "substituted or unsubstituted alkyl" is preferably substituted or unsubstituted $C_1$-$C_4$ alkyl. The substituted or unsubstituted $C_1$-$C_4$ alkyl is preferably substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, or, substituted or unsubstituted tert-butyl.

In the present disclosure, the term "substituted or unsubstituted alkoxy" is preferably substituted or unsubstituted $C_1$-$C_4$ alkoxy. The substituted or unsubstituted $C_1$-$C_4$ alkoxy is preferably substituted or unsubstituted methoxy, substituted or unsubstituted ethoxy, substituted or unsubstituted n-propoxy, substituted or unsubstituted isopropoxy, substituted or unsubstituted n-butoxy, substituted or unsubstituted isobutoxy, or, substituted or unsubstituted tert-butoxy.

In the present disclosure, the term "alkylthio" is preferably —S—$R^s$, wherein, $R^s$ is $C_1$-$C_4$ alkyl.

In the present disclosure, the term "$C_{1-4}$ alkyl" is preferably methyl, ethyl, n-propyl, isopropyl, n-butyl, isobutyl or tert-butyl.

In the present disclosure, the term "$C_{1-4}$ alkoxy" is preferably methoxy, ethoxy, n-propoxy, isopropoxy, n-butoxy, isobutoxy or tert-butoxy.

In the present disclosure, the term "$C_{1-4}$ carboxyl" is preferably

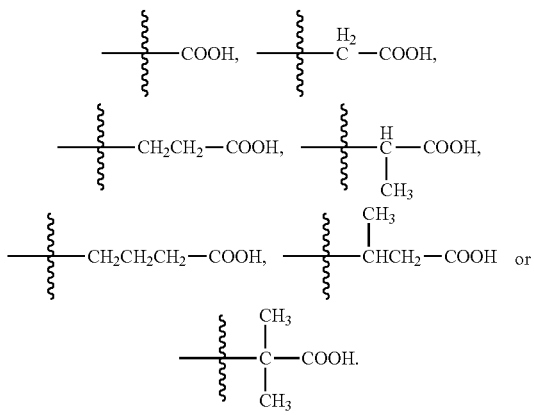

In the present disclosure, the term "$C_{1-4}$ ester group" is preferably

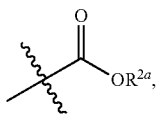

wherein, $R^{2a}$ is $C_1$-$C_4$ alkyl.

In the present disclosure, the term "$C_{1-4}$ amide group" is preferably

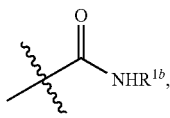

wherein, $R^{1b}$ is hydrogen or $C_1$-$C_4$ alkyl.

In the present disclosure, the term "heteroaromatic ring" is preferably $C_1$-$C_{10}$ heteroaromatic ring, more preferably acridine ring, carbazole ring, cinnoline ring, carboline ring, quinoxaline ring, imidazole ring, pyrazole ring, pyrrole ring, indole ring, indoline ring, benzotriazole ring, benzimidazole ring, furan ring, thiophen ring, isothiazole ring, benzothiophene ring, dihydrobenzothiophene ring, benzofuran ring, isobenzofuran ring, benzoxazole ring, benzofuraxan ring, benzopyrazole ring, quinoline ring, isoindoline ring, isoquinoline ring, oxazole ring, oxadiazole ring, isoxazole ring, indole ring, pyrazine ring, pyridopyridine ring, tetrazolopyridine ring, imidazopyridine ring, imidazopyrazine ring, pyridazine ring, pyridine ring, naphthopyrimidine ring, pyrimidine ring, tetrazole ring, thiadiazole ring, thiazole ring, thiophene ring, triazole ring, quinazoline ring, tetrahydroquinoline ring, dihydrobenzimidazole ring, dihydrobenzofuran ring, dihydrobenzoxazole ring or dihydroquinoline ring.

In the present disclosure, the term "5- to 7-membered heterocarbocyclic ring" refers to 5- to 7-membered heterocarbocyclic ring wherein the heteroatom(s) is(are) selected from the heteroatoms which is oxygen and/or nitrogen and the number of the heteroatom(s) is 1 to 4. The number of ring atoms in the 5- to 7-membered heterocarbocyclic ring is 5, 6 or 7. In the present disclosure, the 5- to 7-membered heterocarbocyclic ring includes but are not limited to: azetidine ring, piperazine ring, piperidine ring, pyrrole ring, morpholine ring, thiomorpholine ring, 1,4-dioxane, pyran ring, dihydroimidazole ring, dihydroisoxazole ring, dihydroisothiazole ring, dihydrooxadiazole ring, dihydrooxazole ring, dihydropyrazine ring, dihydropyrazole ring, dihydropyridine ring, dihydropyrimidine ring, dihydropyrrole ring, dihydroquinoline ring, dihydrotetrazole ring, dihydrothiadiazole ring, dihydrothiazole ring, dihydrotriazole ring, dihydroazetidine ring, imidazole ring, pyrazole ring, pyrrole ring, furan ring, thiophene ring, isothiazole ring, oxazole ring, oxadiazole ring, isoxazole ring, pyrazine ring, pyridazine ring, pyridine ring, pyrimidine ring, tetrazole ring, thiadiazole ring, thiazole ring, thiophene ring and triazole ring; and the 5- to 7-membered heterocarbocyclic ring is preferably 2,3-dihydro-1,4-dioxane

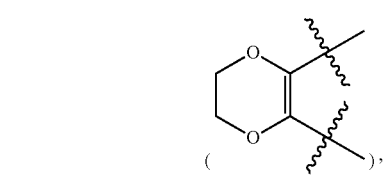 [SMILES: *C1=C(*)OCCO1]

oxazole ring

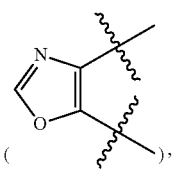

isoxazole ring

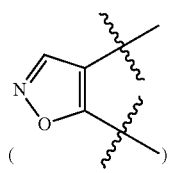 [SMILES: *c1cnoc1*]

or pyrazole ring

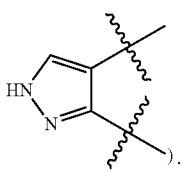

Without departing from the common knowledge in the art, the optimized examples can be obtained by optionally combining the preferred conditions above.

The reagents and raw materials are commercially available.

The positive effects achieved by the present disclosure lie in that: the aromatic vinyl or aromatic ethyl derivative of the present disclosure has a significant inhibitory effect on PD-1/PD-L1, is a kind of small molecular inhibitors with great effect on PD-1/PD-L1 and can alleviate or treat cancers and other related diseases.

DETAILED DESCRIPTION OF THE PREFERRED EMBODIMENT

The following examples further illustrate the present disclosure, but the present disclosure is not limited thereto. The experimental method without particular conditions being specified in the following examples is chosen according to conventional methods and conditions, or product instructions.

In following examples, room temperature referred to 10° C. to 30° C.; overnight referred to 8 to 24 hours, preferably 12 to 18 hours.

The structure of the compounds were confirmed by NMR or MS. NMR was determined by Bruker Avance-500 apparatus using $d_6$-DMSO, $CDCl_3$ and $CD_3OD$ etc. as a solvent, and TMS as an interior label. MS was determined by LC-MS Agilent Technologies 6110 using ESI as an ion source.

Microwave reaction was conducted in Explorer full automatic microwave irradiation equipment supplied by CEM, US Corporation. The magnetron frequency was 2450 MHz, and the continuous microwave output power was 300 W.

The instrument used for preparative high performance liquid chromatography was Gilson 281, and the preparative column was Shimadazu Shim-Pack, PRC-ODS, 20×250 mm, 15 μm.

Example 1

(E)-2-(3-(3-(2,3-dihydrobenzo[b][1,4]dioxin-6-yl)-2-methylstyryl)-4-(trifluoromethyl)benzylamino)-3-hydroxypropanoic acid (Compound 1)

Synthesis Route:

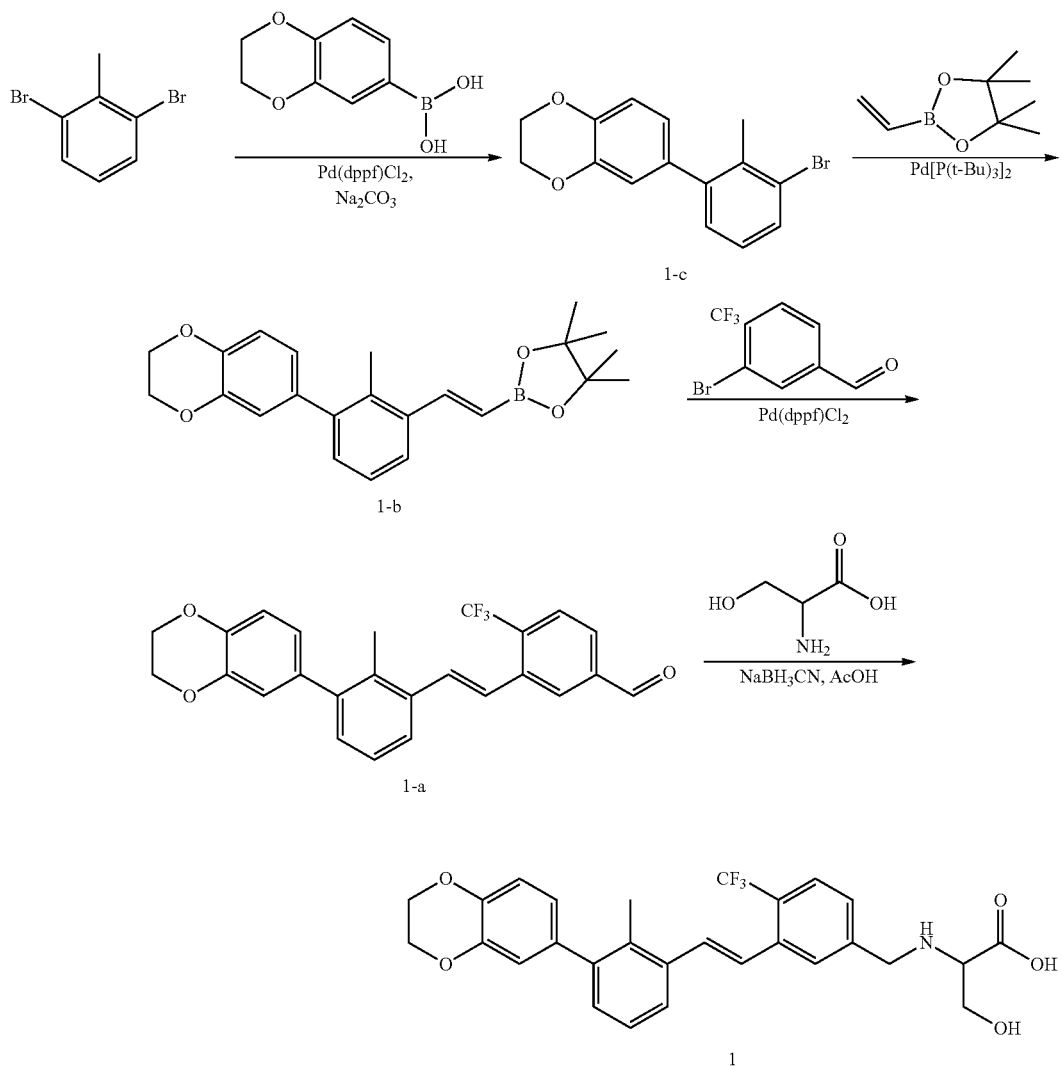

Synthesis of Compound 1-c 1,4-Benzodioxane-6-boronic acid (3.60 g, 20 mmol) and 2,6-dibromotoluene (7.50 g, 30 mmol) were dissolved in a mixed solution of 1,4-dioxane (100 mL) and water (15 mL), and [1,1'-bis(diphenylphosphino)ferrocene]palladium dichloride dichloromethane complex (817 mg, 1 mmol) and sodium carbonate (6.38 g, 60 mmol) were added. After the reaction system was replaced with nitrogen three times, the reaction solution was heated to 80° C. and stirred for 16 hours. The reaction solution was cooled to room temperature, concentrated under reduced pressure, and the residue was purified by silica gel column chromatography (petroleum ether) to obtain compound 1-c (2.70 g, yield: 44%).

Synthesis of Compound 1-b

Compound 1-c (915 mg, 3 mmol) and pinacol vinylboronate (924 mg, 6 mmol) were dissolved in toluene solution (10 mL), and bis(tri-tert-butylphosphine)palladium (120 mg, 0.24 mmol) and triethylamine (2.0 g, 20 mmol) were added. After the reaction system was replaced with nitrogen three times, the reaction solution was heated to 80° C. and stirred for 6 hours. The reaction solution was cooled to room temperature, concentrated under reduced pressure, and the residue was purified by silica gel column chromatography (petroleum ether:ethyl acetate=10:1) to obtain compound 1-b (540 mg, yield: 48%).

Synthesis of Compound 1-a

Compound 1-b (475 mg, 1.26 mmol) and 3-bromo-4-trifluoromethylbenzaldehyde (265.7 mg, 1.05 mmol) were dissolved in a mixed solution of 1,4-dioxane (20 mL) and water (1 mL), [1,1'-bis(diphenylphosphino)ferrocene]palladium dichloride (90.8 mg, 0.105 mmol) and sodium carbonate (277.8 mg, 2.62 mmol) were added. After the reaction system was replaced with nitrogen three times, the reaction solution was heated to 80° C. and stirred for 16 hours. The reaction solution was cooled to room temperature, concentrated under reduced pressure, and the residue was dissolved with ethyl acetate (50 mL), followed by washing with water (20 mL×3) and saturated brine (20 mL) sequentially, and the organic phase was dried over anhydrous sodium sulfate, concentrated under reduced pressure, and the residue was purified by silica gel column chromatography (petroleum ether:ethyl acetate=10:1) to obtain compound 1-a (366 mg, yield: 80.4%).

$^1$H NMR (500 MHz, CDCl$_3$) δ: 10.15 (s, 1H), 8.27 (s, 1H), 7.86 (s, 2H), 7.57-7.55 (d, J=7.5 Hz, 1H), 7.52-7.49 (d, J=16.0 Hz, 1H), 7.37-7.34 (m, 1H), 7.29-7.27 (m, 1H), 7.22-7.21 (m, 1H), 6.93-6.91 (d, J=8.5 Hz, 1H), 6.84-6.83 (m, 1H), 6.79-6.77 (m, 1H), 4.31 (s, 4H), 2.35 (s, 3H) ppm.

Synthesis of Compound 1

Compound 1-a (200 mg, 0.40 mmol) and serine (99 mg, 0.94 mmol) were dissolved in a mixed solution of methanol (15 mL) and dichloromethane (15 mL), and acetic acid (0.05 mL, 0.94 mmol) was added. After the reaction solution was stirred at room temperature for 2 hours, to the reaction solution was added sodium cyanoborohydride (119 mg, 1.89 mmol) and continued to be stirred for 12 hours. The reaction solution was concentrated under reduced pressure, and the residue was dissolved with ethyl acetate (50 mL), followed by washing with water (20 mL) and saturated brine (20 mL) sequentially, and the organic phase was dried over anhydrous sodium sulfate, and concentrated under reduced pressure, and the residue was purified by high performance liquid chromatography (mobile phase: water (10 mM ammonium bicarbonate), acetonitrile; gradient: 15% to 65% (the initial mobile phase was 15% water and 85% acetonitrile, the final mobile phase was 65% water and 35% acetonitrile, wherein, % refers to volume percentage) to obtain compound 1 (12 mg, yield: 5.8%). LC-MS (ESI): m/z=514 [M+H]$^+$.

$^1$H NMR (400 MHz, DMSO) δ: 8.05 (s, 1H), 7.74-7.73 (d, J=6.4 Hz, 1H), 7.59-7.51 (m, 3H), 7.30-7.15 (m, 3H), 6.93-6.91 (d, J=6.8 Hz, 1H), 6.80-6.75 (m, 2H), 4.28 (s, 4H), 4.09-4.06 (d, J=11.2 Hz, 1H), 3.96-3.93 (d, J=11.2 Hz, 1H), 3.69-3.62 (m, 2H), 3.20-3.18 (t, J=4.0 Hz, 1H), 2.29 (s, 3H) ppm.

Example 2

(E)-2-((3-(2-(4'-methoxy-2-methylbiphenyl-3-yl) vinyl)-4-methylbenzyl)amino)-3-hydroxy-2-methyl-propanoic acid (Compound 2)

Synthesis Route:

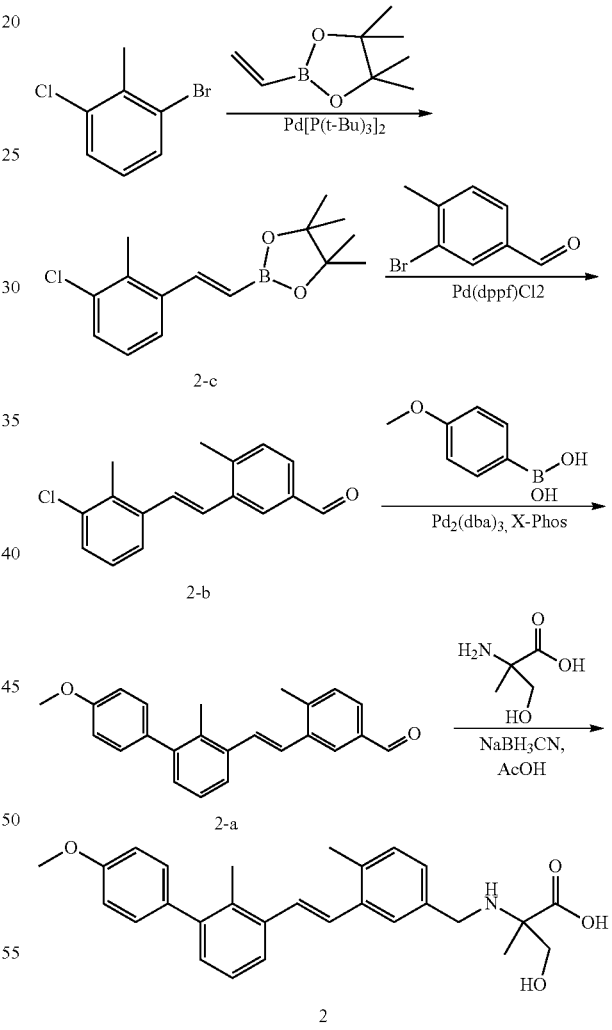

Synthesis of Compound 2-c

To a solution of 2-bromo-6-chlorotoluene (15.67 g, 76.26 mmol) and pinacol vinylboronate (14.30 g, 91.51 mmol) in toluene (300 mL) were added bis(tri-tert-butylphosphine) palladium (2.73 g, 5.34 mmol) and triethylamine (61.74 g, 610.08 mmol) at room temperature, and the reaction solution was heated to 80° C. and stirred overnight under nitrogen. After the completion of the reaction, the reaction solution was diluted with ethyl acetate (100 mL), washed with water (100 mL) and saturated brine (100 mL). The obtained organic phase was dried over anhydrous sodium sulfate, concentrated under reduced pressure, and the residue was purified by silica gel column chromatography (petroleum ether:ethyl acetate=10:1) to obtain compound 2-c (10.5 g, yield: 49.4%).

$^1$H NMR (500 MHz, CDCl$_3$) δ: 7.65-7.62 (d, J=18.5 Hz, 1H), 7.42-7.41 (d, J=7.5 Hz, 1H), 7.31-7.30 (d, J=7.5 Hz, 1H), 7.12-7.09 (t, 1H), 6.06-6.02 (d, J=18.0 Hz, 1H), 2.45 (s, 3H), 1.32 (s, 12H) ppm.

Synthesis of Compound 2-b

To a solution of 3-bromo-4-methylbenzaldehyde (5.0 g, 17.95 mmol) and 2-c (2.98 g, 14.96 mmol) in 1,4-dioxane (40 mL) and water (2 mL) were added [1,1'-bis(diphenylphosphino)ferrocene]palladium dichloride (1.294 g, 1.496 mmol) and sodium carbonate (3.963 g, 37.39 mmol) at room temperature, and the reaction solution was heated to 80° C. and stirred overnight under nitrogen. After the completion of the reaction, the reaction solution was diluted with ethyl acetate (50 mL), washed with water (50 mL) and saturated brine (50 mL) sequentially. The obtained organic phase was dried over anhydrous sodium sulfate, concentrated under reduced pressure, and the residue was purified by silica gel column chromatography (petroleum ether:ethyl acetate=40:1) to obtain compound 2-b (3.31 g, yield: 81.9%).

$^1$H NMR (500 MHz, CDCl$_3$) δ: 10.03 (s, 1H), 8.08 (s, 1H), 7.72-7.70 (d, J=8.0 Hz, 1H), 7.47-7.45 (d, J=7.5 Hz, 1H), 7.37-7.31 (m, 3H), 7.18-7.12 (m, 2H), 2.50 (s, 6H) ppm.

Synthesis of Compound 2-a

To a solution of p-methoxyphenylboronic acid (202 mg, 1.329 mmol) and 2-b (300 mg, 1.108 mmol) in toluene (20 mL) were added tris(dibenzylideneacetone)dipalladium (101.6 mg, 0.111 mmol), 2-dicyclohexylphosphino-2',4',6'-triisopropylbiphenyl (211.7 mg, 0.444 mmol) and potassium phosphate (705.6 mg, 3.324 mmol), and the reaction solution was heated to 90° C. and stirred overnight under nitrogen. After the completion of the reaction, the reaction solution was diluted with ethyl acetate (50 mL), and washed with water (50 mL) and saturated brine (50 mL) sequentially. The obtained organic phase was dried over anhydrous sodium sulfate, concentrated under reduced pressure, and the residue was purified by silica gel column chromatography (petroleum ether:ethyl acetate=40:1) to obtain compound 2-a (334 mg, yield: 87.9%).

$^1$H NMR (500 MHz, CDCl$_3$) δ: 10.03 (s, 1H), 8.10 (s, 1H), 7.71-7.69 (d, J=7.5 Hz, 1H), 7.58-7.56 (d, J=7.5 Hz, 1H), 7.42-7.36 (m, 4H), 7.21-7.17 (m, 2H), 6.98-6.96 (d, J=8.5 Hz, 2H), 3.87 (s, 3H), 2.51 (s, 3H), 2.33 (s, 3H) ppm.

Synthesis of Compound 2

To a mixed solution of 2-a (330 mg, 0.964 mmol) and 2-methylserine (229.9 mg, 1.93 mmol) in methanol (10 mL) and dichloromethane (10 mL) was added acetic acid (115.9 mg, 1.93 mmol) at room temperature, and the reaction solution was stirred at room temperature for 1 hour. Then, to the reaction solution was added sodium cyanoborohydride (302.9 mg, 4.82 mmol) and was stirred for 16 hours. After the completion of the reaction, the organic solvent was concentrated by rotary evaporation to dryness, and the residue was dissolved in ethyl acetate (50 mL), followed by washing with water (50 mL) and saturated brine (50 mL) sequentially. The obtained organic phase was dried over anhydrous sodium sulfate, concentrated under reduced pressure, and the residue was purified by silica gel thin-layer chromatography preparative plate (dichloromethane:methanol=10:1) to obtain compound 2 (85 mg, yield: 19.8%). LC-MS (ESI): m/z=444.0 [M−H]$^+$.

$^1$H NMR (500 MHz, DMSO-d$_6$) δ: 7.79 (s, 1H), 7.67-7.65 (d, J=7.5 Hz, 1H), 7.40-7.37 (d, J=16.5 Hz, 1H), 7.30-7.23 (m, 6H), 7.14-7.13 (d, J=7.5 Hz, 1H), 7.03-7.01 (d, J=9.0 Hz, 2H), 4.01-3.94 (m, 2H), 3.81 (s, 3H), 3.68-3.66 (d, J=11.5 Hz, 1H), 3.60-3.58 (d, J=11.0 Hz, 1H), 2.41 (s, 3H), 2.29 (s, 3H), 1.31 (s, 3H) ppm.

Example 3

(E)-2-(3-(2-(3'-fluoro-2-methylbiphenyl-3-yl)vinyl)-4-(trifluoromethyl)benzylamino)-3-hydroxy-2-methylpropanoic acid (Compound 3)

Synthesis Route:

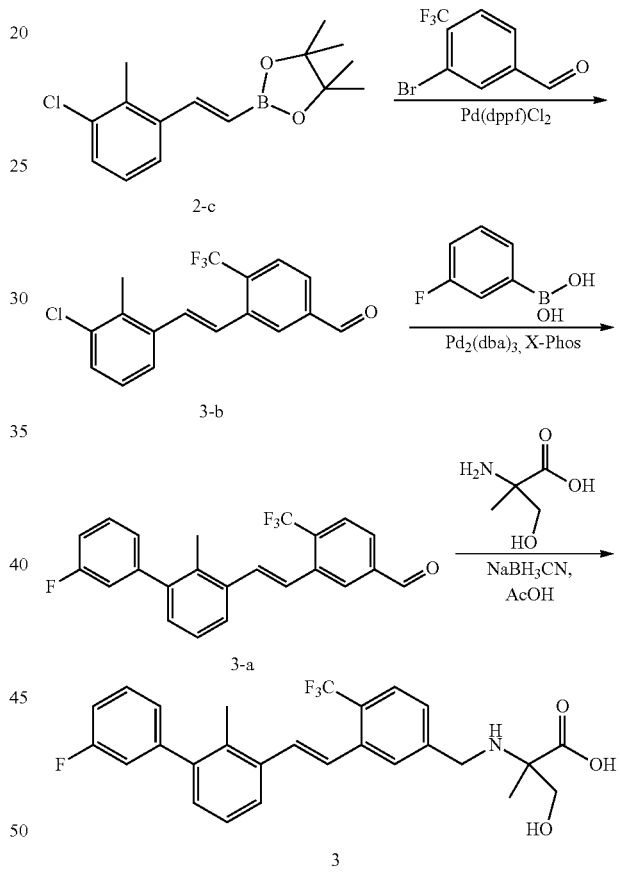

Synthesis of Compound 3-b

To a mixed solution of 3-bromo-4-trifluoromethylbenzaldehyde (4.16 g, 16.45 mmol) and compound 2-c (5.5 g, 19.74 mmol) in 1,4-dioxane (40 mL) and water (2 mL) were added [1,1'-bis(diphenylphosphino)ferrocene]palladium dichloride (1.423 g, 1.645 mmol) and sodium carbonate (4.36 g, 41.13 mmol) at room temperature, and the reaction solution was heated to 80° C. and stirred for 16 hours under nitrogen. After the completion of the reaction, the reaction solution was diluted with ethyl acetate (50 mL), and washed with water (50 mL) and saturated brine (50 mL) sequentially. The obtained organic phase was dried over anhydrous sodium sulfate, concentrated under reduced pressure, and the residue was purified by silica gel column chromatography (petroleum ether:ethyl acetate=40:1) to obtain compound 3-b (4.16 g, yield: 78%).

$^1$H NMR (500 MHz, CDCl$_3$) δ: 10.15 (s, 1H), 8.25 (s, 1H), 7.87 (s, 2H), 7.47-7.40 (m, 2H), 7.37-7.36 (d, J=7.0 Hz, 1H), 7.32-7.29 (m, 1H), 7.20-7.17 (m, 1H), 2.50 (s, 3H) ppm.

Synthesis of Compound 3-a

To a solution of compound 3-b (300 mg, 0.93 mmol) in toluene (20 mL) were added 3-fluorophenylboronic acid (156 mg, 1.11 mmol), potassium phosphate (590 mg, 2.78 mmol), 2-dicyclohexylphosphino-2',4',6'-triisopropylbiphenyl (66 mg, 0.132 mmol) and tris(dibenzylideneacetone)dipalladium (30 mg, 0.03 mmol). The reaction system was replaced with nitrogen three times, and the reaction solution was heated to 90° C. and stirred for 12 hours. The reaction solution was cooled to room temperature, concentrated under reduced pressure, and the residue was purified by silica gel column chromatography (petroleum ether:ethyl acetate=100:1) to obtain 3-a (240 mg, yield: 68%) as a yellow solid. LC-MS (ESI): m/z=385 [M+H]$^+$.

Synthesis of Compound 3

Compound 3-a (240 mg, 0.625 mmol) and 2-methylserine (150 mg, 1.25 mmol) were dissolved in a mixed solution of methanol (15 mL) and dichloromethane (15 mL), and acetic acid (0.07 mL, 1.25 mmol) was added. After the reaction solution was stirred at room temperature for 2 hours, to the reaction solution was added sodium cyanoborohydride (157 mg, 2.5 mmol) and continued to be stirred for 12 hours. The reaction solution was concentrated under reduced pressure, and the residue was dissolved with ethyl acetate (50 mL), followed by washing with water (20 mL) and saturated brine (20 mL) sequentially, and the organic phase was dried over anhydrous sodium sulfate and concentrated under reduced pressure, and the residue was purified by high performance liquid chromatography (mobile phase: water (10 mM ammonium bicarbonate), acetonitrile; gradient: 15% to 65% (the initial mobile phase was 15% water and 85% acetonitrile, and the final mobile phase was 65% water and 35% acetonitrile, wherein % refers to volume percentage)) to obtain compound 3 (75 mg, yield: 24.5%). LC-MS (ESI): m/z=488 [M+H]$^+$.

$^1$H NMR (400 MHz, DMSO-d$_6$) δ: 8.06 (s, 1H), 7.76-7.74 (d, J=6.4 Hz, 1H), 7.61-7.56 (m, 3H), 7.53-7.48 (m, 1H), 7.36-7.32 (t, J=12.4 Hz, 1H), 7.07-7.17 (m, 5H), 3.99 (s, 2H), 3.64-3.61 (d, J=8.8 Hz, 1H), 3.57-3.55 (d, J=8.8 Hz, 1H), 2.29 (s, 3H), 1.27 (s, 3H) ppm.

Example 4

(E)-2-(3-(2-(4'-methylthio-2-methylbiphenyl-3-yl)vinyl)-4-methylbenzylamino)-3-hydroxy-2-methyl-propanoic acid (Compound 4)

Synthesis Route:

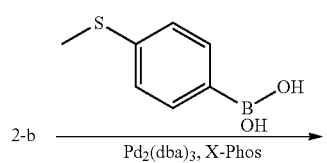

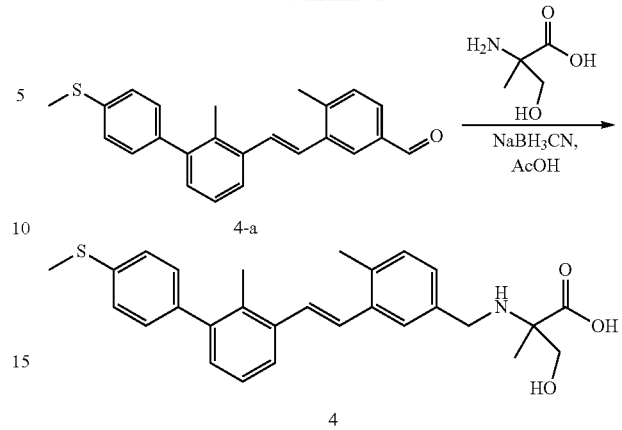

Synthesis of Compound 4-a

To a solution of p-methylthiophenylboronic acid (223.3 mg, 1.329 mmol) and 2-b (300 mg, 1.108 mmol) in toluene (20 mL) were added tris(dibenzylideneacetone)dipalladium (101.6 mg, 0.111 mmol), 2-dicyclohexylphosphino-2',4',6'-triisopropylbiphenyl (211.7 mg, 0.444 mmol) and potassium phosphate (705.6 mg, 3.324 mmol) at room temperature, and the reaction solution was heated to 90° C. and stirred overnight under nitrogen. After the completion of the reaction, the reaction solution was diluted with ethyl acetate (50 mL), and washed with water (50 mL) and saturated brine (50 mL) sequentially. The obtained organic phase was dried over anhydrous sodium sulfate, concentrated under reduced pressure, and the residue was purified by silica gel column chromatography (petroleum ether:ethyl acetate=40:1) to obtain compound 4-a (323 mg, yield: 81.2%).

$^1$H NMR (500 MHz, CDCl$_3$) δ: 10.03 (s, 1H), 8.10 (s, 1H), 7.71-7.69 (d, J=7.0 Hz, 1H), 7.63-7.62 (m, 1H), 7.59-7.58 (d, J=7.5 Hz, 2H), 7.43-7.36 (m, 4H), 7.33-7.32 (m, 2H), 7.21-7.18 (m, 2H), 2.54 (s 3H), 2.51 (s, 3H), 2.33 (s, 3H) ppm.

Synthesis of Compound 4

To a mixed solution of 4-a (323 mg, 0.901 mmol) and 2-methylserine (214.7 mg, 1.802 mmol) in methanol (10 mL) and dichloromethane (10 mL) was added acetic acid (108.2 mg, 1.802 mmol) at room temperature, and the reaction solution was stirred at room temperature for 1 hour. Then, to the reaction solution was added sodium cyanoborohydride (254.5 mg, 4.505 mmol) and was stirred for 16 hours. After the completion of the reaction, the organic solvent was concentrated by rotary evaporation to dryness. And the residue was dissolved in ethyl acetate (20 mL), followed by washing with water (20 mL) and saturated brine (20 mL) sequentially. The obtained organic phase was dried over anhydrous sodium sulfate, concentrated under reduced pressure, and the residue was purified by silica gel thin layer chromatography preparative plate (dichloromethane:methanol=10:1) to obtain compound 4 (112 mg, yield: 26.9%). LC-MS (ESI): m/z=460.0 [M−H]$^+$.

$^1$H NMR (500 MHz, CD$_3$OD) δ: 7.78 (s, 1H), 7.69-7.68 (d, J=7.5 Hz, 1H), 7.39-7.33 (m, 3H), 7.31-7.26 (m, 5H), 7.24-7.22 (d, J=8.0 Hz, 1H), 7.15-7.13 (d, J=7.0 Hz, 1H), 4.00-3.92 (m, 2H), 3.67-3.65 (d, J=11.5 Hz, 1H), 3.59-3.57 (d, J=10.5 Hz, 1H), 2.52 (s, 3H), 2.41 (s, 3H), 2.29 (s, 3H), 1.30 (s, 3H) ppm

Example 5

(E)-2-(3-(2-(2-methylbiphenyl-3-yl)vinyl)-4-(trifluoromethyl)benzylamino)-3-hydroxy-2-methylpropanoic acid (Compound 5)

Synthesis Route:

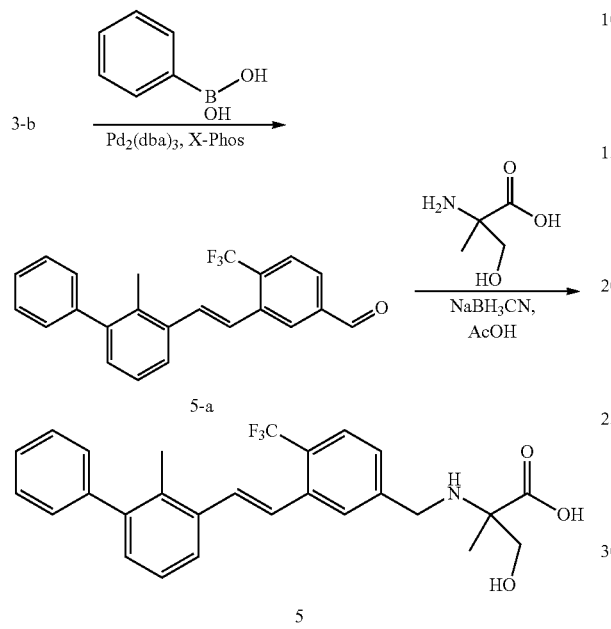

Synthesis of Compound 5-a

To a solution of phenylboronic acid (135.3 mg, 1.11 mmol) and compound 3-b (300 mg, 0.924 mmol) in toluene (20 mL) were added tris(dibenzylideneacetone)dipalladium (84.2 mg, 0.092 mmol), 2-dicyclohexylphosphino-2',4',6'-triisopropylbiphenyl (175.4 mg, 0.368 mmol) and potassium phosphate (588.4 mg, 2.772 mmol) at room temperature, and the reaction solution was heated to 90° C. and stirred overnight under nitrogen. After the completion of the reaction, the reaction solution was diluted with ethyl acetate (50 mL), and washed with water (50 mL) and saturated brine (50 mL) sequentially. The obtained organic phase was dried over anhydrous sodium sulfate and concentrated under reduced pressure, and the residue was purified by silica gel column chromatography (petroleum ether:ethyl acetate=40:1) to obtain compound 5-a (254 mg, yield: 74.9%).

$^1$H NMR (500 MHz, CDCl$_3$) δ: 10.15 (s, 1H), 8.28 (s, 1H), 7.87 (s, 2H), 7.60-7.59 (d, J=7.5 Hz, 1H), 7.53-7.50 (d, J=16.0 Hz, 1H), 7.45-7.42 (m, 2H), 7.39-7.35 (m, 2H), 7.33-7.29 (m, 3H), 7.25-7.23 (m, 1H), 2.33 (s, 3H) ppm.

Synthesis of Compound 5

To a mixed solution of 5-a (254 mg, 0.693 mmol) and 2-methylserine (165.1 mg, 1.386 mmol) in methanol (10 mL) and dichloromethane (10 mL) was added acetic acid (83.2 mg, 1.386 mmol) at room temperature, and the reaction solution was stirred at room temperature for 1 hour. Then, to the reaction solution was added sodium cyanoborohydride (254.5 mg, 4.505 mmol) and was stirred for 16 hours. After the completion of the reaction, the organic solvent was concentrated by rotary evaporation to dryness, and the residue was dissolved in ethyl acetate (20 mL), followed by washing with water (20 mL) and saturated brine (20 mL) sequentially. The obtained organic phase was dried over anhydrous sodium sulfate and concentrated under reduced pressure, and the residue was purified by silica gel thin layer chromatography preparative plate (dichloromethane:methanol=10:1) to obtain compound 5 (95 mg, yield: 29.2%). LC-MS (ESI): m/z=468.0 [M–H]$^+$.

$^1$H NMR (500 MHz, CD$_3$OD) δ: 8.17 (s, 1H), 7.80-7.79 (d, J=8.0 Hz, 1H), 7.68-7.62 (m, 2H), 7.57-7.56 (d, J=7.5 Hz, 1H), 7.46-7.43 (m, 2H), 7.39-7.29 (m, 5H), 7.21-7.19 (d, J=7.5 Hz, 1H), 4.35-4.27 (m, 2H), 4.02-4.00 (d, J=12.0 Hz, 1H), 3.86-3.83 (d, J=12.0 Hz, 1H), 2.34 (s, 3H), 1.56 (s, 3H) ppm.

Example 6

(E)-2-(3-(2-(4'-fluoro-2-methylbiphenyl-3-yl)vinyl)-4-(trifluoromethyl)benzylamino)-3-hydroxy-2-methylpropanoic acid (Compound 6)

Synthesis Route:

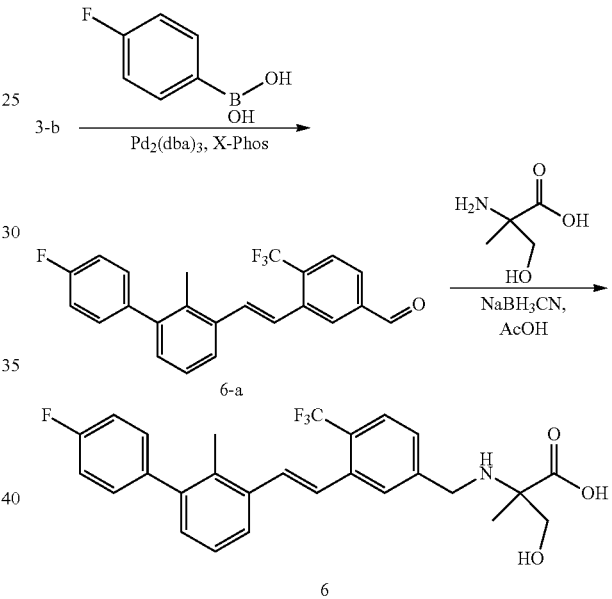

Synthesis of Compound 6-a

To a solution of compound 3-b (300 mg, 0.93 mmol) in toluene (20 mL) were added 3-fluorophenylboronic acid (156 mg, 1.11 mmol), potassium phosphate (590 mg, 2.78 mmol), 2-dicyclohexylphosphino-2',4',6'-triisopropylbiphenyl (60 mg, 0.132 mmol) and tris(dibenzylideneacetone)dipalladium (30 mg, 0.03 mmol). The reaction system was replaced with nitrogen three times, and the reaction solution was heated to 90° C. and stirred for 12 hours. The reaction solution was cooled to room temperature, concentrated under reduced pressure, and the residue was purified by silica gel column chromatography (petroleum ether:ethyl acetate=100:1) to obtain 6-a (240 mg, yield: 68%) as a yellow solid. LC-MS (ESI): m/z=385 [M+H]$^+$.

Synthesis of Compound 6

Compound 6-a (240 mg, 0.625 mmol) and 2-methylserine (150 mg, 1.25 mmol) were dissolved in a mixed solution of methanol (15 mL) and dichloromethane (15 mL), and acetic acid (0.07 mL, 1.25 mmol) was added. After the reaction solution was stirred at room temperature for 2 hours, to the reaction solution was added sodium cyanoborohydride (157 mg, 2.5 mmol) and continued to be stirred for 12 hours. The reaction solution was concentrated under reduced pressure, and the residue was dissolved with ethyl acetate (50 mL), followed by washing with water (20 mL) and saturated brine (20 mL) sequentially. The organic phase was dried over anhydrous sodium sulfate, and concentrated under reduced pressure. The residue was purified by high performance liquid chromatography (mobile phase: water (10 mM ammonium bicarbonate), acetonitrile; gradient: 15% to 65% (the initial mobile phase was 15% water and 85% acetonitrile, and the final mobile phase was 65% water and 35% acetonitrile, wherein % refers to volume percentage)) to obtain compound 6 (65 mg, yield: 21.3%). LC-MS (ESI): m/z=488 [M+H]$^+$.

$^1$H NMR (400 MHz, DMSO-d$_6$) δ: 8.06 (s, 1H), 7.76-7.74 (d, J=6.8 Hz, 1H), 7.59-7.56 (m, 3H), 7.39-7.23 (m, 6H), 7.20-7.19 (m, 1H), 3.99 (s, 2H), 3.63-3.61 (d, J=8.8 Hz, 1H), 3.56-3.54 (d, J=8.8 Hz, 1H), 2.28 (s, 3H), 1.27 (s, 3H) ppm.

Example 7

(E)-2-(3-(2-(4'-fluoro-2-methylbiphenyl-3-yl)vinyl)-4-methylbenzylamino)-3-hydroxy-2-methylpropanoic acid (Compound 7)

Synthesis Route:

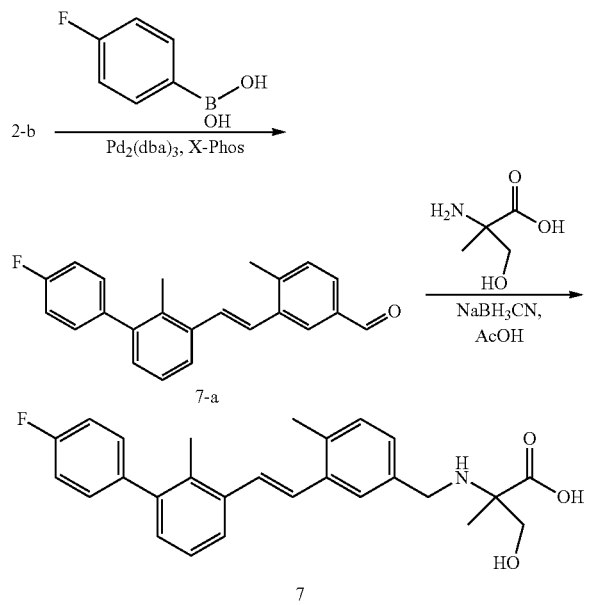

Synthesis of Compound 7-a

To a solution of compound 2-b (300 mg, 1.11 mmol) in toluene (20 mL) were added p-fluorophenylboronic acid (187 mg, 1.33 mmol), potassium phosphate (708 mg, 3.33 mmol), 2-dicyclohexylphosphino-2',4',6'-triisopropylbiphenyl (60 mg, 0.132 mmol) and tris(dibenzylideneacetone)dipalladium (30 mg, 0.03 mmol). The reaction system was replaced with nitrogen three times, and the reaction solution was heated to 90° C. and stirred for 12 hours. The reaction solution was cooled to room temperature, concentrated under reduced pressure, and the residue was purified by silica gel column chromatography (petroleum ether:ethyl acetate=100:1) to obtain 7-a (340 mg, yield: 92%) as a yellow solid. LC-MS (ESI): m/z=331 [M+H]$^+$.

Synthesis of Compound 7

Compound 7-a (340 mg, 1.15 mmol) and 2-methylserine (274 mg, 2.3 mmol) were dissolved in a mixed solution of methanol (15 mL) and dichloromethane (15 mL), and acetic acid (0.07 mL, 1.25 mmol) was added. After the reaction solution was stirred at room temperature for 2 hours, to the reaction solution was added sodium cyanoborohydride (290 mg, 4.6 mmol) and continued to be stirred for 12 hours. The reaction solution was concentrated under reduced pressure, and the residue was dissolved with ethyl acetate (50 mL), followed by washing with water (20 mL) and saturated brine (20 mL) sequentially. The organic phase was dried over anhydrous sodium sulfate and concentrated under reduced pressure. The residue was purified by high performance liquid chromatography (mobile phase: water (10 mM ammonium bicarbonate), acetonitrile; gradient: 15% to 65% (the initial mobile phase was 15% water and 85% acetonitrile, and the final mobile phase was 65% water and 35% acetonitrile, wherein % refers to volume percentage)) to obtain compound 7 (35 mg, yield: 7%). LC-MS (ESI): m/z=434 [M+H]$^+$.

$^1$H NMR (400 MHz, DMSO-d$_6$) δ: 7.77 (s, 1H), 7.70-7.68 (d, J=6 Hz, 1H), 7.39-7.35 (m, 3H), 7.31-7.23 (m, 6H), 7.15-7.14 (m, 1H), 3.99-3.92 (m, 2H), 3.67-3.64 (d, J=9.2 Hz, 1H), 3.58-3.56 (d, J=9.2 Hz, 1H), 2.41 (s, 3H), 2.26 (s, 3H), 1.29 (s, 3H) ppm.

Example 8

(E)-2-(3-(2-(2-methylbiphenyl-3-yl)vinyl)-4-methylbenzylamino)-3-hydroxy-2-methylpropanoic acid (Compound 8)

Synthesis Route:

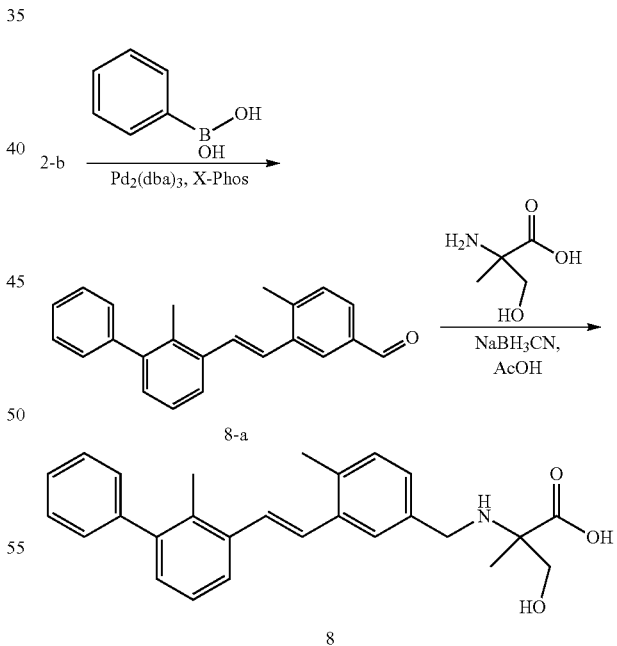

Synthesis of Compound 8-a

To a solution of compound 2-b (300 mg, 1.108 mmol) in toluene (20 mL) were added phenylboronic acid (162.2 mg, 1.33 mmol), potassium phosphate (705.6 mg, 3.324 mmol), 2-dicyclohexylphosphino-2',4',6'-triisopropylbiphenyl (211.7 mg, 0.444 mmol) and tris(dibenzylideneacetone)dipalladium (101.6 mg, 0.111 mmol). The reaction system was replaced with nitrogen three times, and the reaction solution was heated to 90° C. and stirred for 12 hours. After the completion of the reaction, the reaction solution was diluted with ethyl acetate (50 mL), and washed with water (50 mL) and saturated brine (50 mL) sequentially. The obtained organic phase was dried over anhydrous sodium sulfate, concentrated under reduced pressure, and the residue was purified by silica gel column chromatography (petroleum ether:ethyl acetate=40:1) to obtain compound 8-a (323 mg, yield: 93.1%).

$^1$H NMR (500 MHz, CDCl$_3$) δ: 10.03 (s, 1H), 8.10 (s, 1H), 7.71-7.69 (d, J=8.0 Hz, 1H), 7.60-7.59 (d, J=7.0 Hz, 1H), 7.45-7.40 (m, 3H), 7.38-7.36 (m, 2H), 7.33-7.29 (m, 3H), 7.23-7.18 (m, 2H), 2.52 (s, 3H), 2.32 (s, 3H) ppm.

Synthesis of Compound 8

To a mixed solution of 8-a (323 mg, 1.034 mmol) and 2-methylserine (246.3 mg, 2.068 mmol) in methanol (10 mL) and dichloromethane (10 mL) was added acetic acid (124.2 mg, 2.068 mmol) at room temperature, and the reaction solution was stirred at room temperature for 1 hour. Then, to the reaction solution was added sodium cyanoborohydride (324.9 mg, 5.17 mmol) and stirred for 16 hours. After the completion of the reaction, the organic solvent was concentrated by rotary evaporation to dryness, and the residue was dissolved with ethyl acetate (20 mL), followed by washing with water (20 mL) and saturated brine (20 mL) sequentially. The obtained organic phase was dried over anhydrous sodium sulfate, concentrated under reduced pressure, and the residue was purified by silica gel thin-layer chromatography preparative plate (dichloromethane:methanol=10:1) to obtain compound 8 (95 mg, yield: 22.1%). LC-MS (ESI): m/z=414.0 [M−H]$^+$.

$^1$H NMR (500 MHz, CD$_3$OD) δ: 7.87 (s, 1H), 7.64-7.63 (d, J=7.5 Hz, 1H), 7.52-7.48 (d, J=16.0 Hz, 1H), 7.46-7.43 (m, 2H), 7.39-7.36 (m, 2H), 7.32-7.26 (m, 5H), 7.16-7.15 (d, J=6.5 Hz, 1H), 4.23-4.15 (m, 2H), 4.00-3.98 (d, J=12.0 Hz, 1H), 3.84-3.81 (d, J=12.0 Hz, 1H), 3.37 (s, 3H), 2.48 (s, 3H), 2.32 (s, 3H), 1.54 (s, 3H) ppm.

Example 9

(E)-2-(3-(2-(3'-methyl-2-methylbiphenyl-3-yl)vinyl)-4-methylbenzylamino)-3-hydroxy-2-methylpropanoic acid (Compound 9)

Synthesis Route:

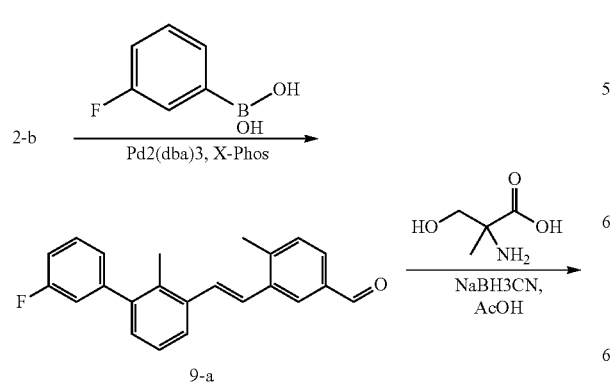

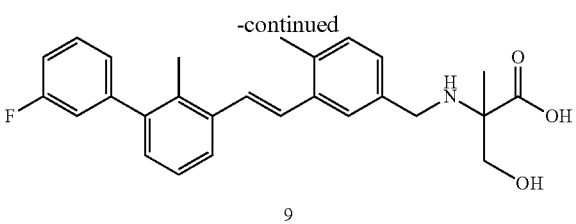

Synthesis of Compound 9-a

To a solution of compound 2-b (300 mg, 1.11 mmol) in toluene (20 mL) were added 3-fluorophenylboronic acid (187 mg, 1.33 mmol), potassium phosphate (708 mg, 3.33 mmol), 2-dicyclohexylphosphino-2',4',6'-triisopropylbiphenyl (60 mg, 0.132 mmol) and tris(dibenzylideneacetone)dipalladium (30 mg, 0.03 mmol). The reaction system was replaced with nitrogen three times, and the reaction solution was heated to 90° C. and stirred for 12 hours. The reaction solution was cooled to room temperature, concentrated under reduced pressure, and the residue was purified by silica gel column chromatography (petroleum ether:ethyl acetate=100:1) to obtain 9-a (330 mg, yield: 90%) as a yellow solid. LC-MS (ESI): m/z=331 [M+H]$^+$.

Synthesis of Compound 9

Compound 9-a (330 mg, 1.0 mmol) and 2-methylserine (238 mg, 2.0 mmol) were dissolved in a mixed solution of methanol (15 mL) and dichloromethane (15 mL), and acetic acid (0.1 mL, 2.3 mmol) was added. After the reaction solution was stirred at room temperature for 2 hours, to the reaction solution was added sodium cyanoborohydride (251 mg, 4.0 mmol) and continued to be stirred for 12 hours. The reaction solution was concentrated under reduced pressure, and the residue was dissolved with ethyl acetate (50 mL), followed by washing with water (20 mL) and saturated brine (20 mL) sequentially. The organic phase was dried over anhydrous sodium sulfate and concentrated under reduced pressure. The residue was purified by high performance liquid chromatography (mobile phase: water (10 mM ammonium bicarbonate), acetonitrile; gradient: 15% to 65% (the initial mobile phase was 15% water and 85% acetonitrile, and the final mobile phase was 65% water and 35% acetonitrile, wherein % refers to volume percentage)) to obtain compound 9 (80 mg, yield: 18.4%). LC-MS (ESI): m/z=434 [M+H]$^+$.

$^1$H NMR (400 MHz, DMSO-d$_6$) δ: 7.78 (s, 1H), 7.72-7.71 (d, J=6 Hz, 1H), 7.52-7.48 (m, 1H), 7.39-7.36 (m, 1H), 7.32-7.26 (m, 3H), 7.22-7.16 (m, 5H), 3.99-3.92 (m, 2H), 3.67-3.65 (d, J=9.2 Hz, 1H), 3.59-3.57 (d, J=9.2 Hz, 1H), 2.41 (s, 3H), 2.28 (s, 3H), 1.29 (s, 3H) ppm.

Example 10

(E)-2-(3-(2-(4'-chloro-2-methylbiphenyl-3-yl)vinyl)-4-(trifluoromethyl)benzylamino)-3-hydroxy-2-methylpropanoic acid (Compound 10)

Synthesis Route:

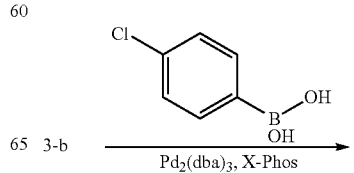

47
-continued

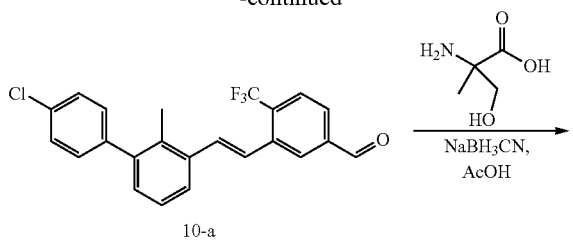

10-a

Synthesis of Compound 10-a

To a solution of p-chlorophenylboronic acid (173.6 mg, 1.11 mmol) and compound 3-b (300 mg, 0.924 mmol) in toluene (20 mL) were added tris(dibenzylideneacetone)dipalladium (84.2 mg, 0.092 mmol), 2-dicyclohexylphosphino-2',4',6'-triisopropylbiphenyl (175.4 mg, 0.368 mmol) and potassium phosphate (588.4 mg, 2.772 mmol) at room temperature, and the reaction solution was heated to 90° C. and stirred overnight under nitrogen. After the completion of the reaction, the reaction solution was diluted with ethyl acetate (50 mL), and washed with water (50 mL) and saturated brine (50 mL) sequentially. The obtained organic phase was dried over anhydrous sodium sulfate, concentrated under reduced pressure, and the residue was purified by silica gel column chromatography (petroleum ether:ethyl acetate=40:1) to obtain compound 10-a (144 mg, yield: 38.9%).

Synthesis of Compound 10

To a mixed solution of 10-a (144 mg, 0.359 mmol) and 2-methylserine (85.5 mg, 0.718 mmol) in methanol (10 mL) and dichloromethane (10 mL) was added acetic acid (43.1 mg, 0.718 mmol) at room temperature, and the reaction solution was stirred at room temperature for 1 hour. Then, to the reaction solution was added sodium cyanoborohydride (112.8 mg, 1.795 mmol) and was stirred for 16 hours. After the completion of the reaction, the organic solvent was concentrated by rotary evaporation to dryness, and the residue was dissolved with ethyl acetate (20 mL), followed by washing with water (20 mL) and saturated brine (20 mL) sequentially. The obtained organic phase was dried over anhydrous sodium sulfate, concentrated under reduced pressure, and the residue was purified by silica gel thin layer chromatography preparative plate (dichloromethane:methanol=10:1) to obtain compound 10 (27 mg, yield: 14.9%). LC-MS (ESI): m/z=502.0 [M−H]+.

$^1$H NMR (500 MHz, CD$_3$OD) δ: 8.16 (s, 1H), 7.80-7.78 (d, J=8.0 Hz, 1H), 7.66-7.56 (m, 3H), 7.46-7.44 (m, 2H), 7.36-7.30 (m, 4H), 7.20-7.18 (m, 1H), 4.31-4.26 (m, 2H), 4.01-3.99 (d, J=12.0 Hz, 1H), 3.85-3.83 (d, J=12.0 Hz, 1H), 2.33 (s, 3H), 1.56 (s, 3H) ppm.

48

Example 11

(E)-2-(3-(2-(4'-methoxy-2-methylbiphenyl-3-yl)vinyl)-4-(trifluoromethyl)benzylamino)-3-hydroxy-2-methylpropanoic acid (Compound 11)

Synthesis Route:

Synthesis of Compound 11-a

To a solution of p-methoxyphenylboronic acid (168.7 mg, 1.11 mmol) and compound 3-b (300 mg, 0.924 mmol) in toluene (20 mL) were added tris(dibenzylideneacetone)dipalladium (84.2 mg, 0.092 mmol), 2-dicyclohexylphosphino-2',4',6'-triisopropylbiphenyl (175.4 mg, 0.368 mmol) and potassium phosphate (588.4 mg, 2.772 mmol) at room temperature, and the reaction solution was heated to 90° C. and stirred overnight under nitrogen. After the reaction solution was cooled to room temperature, the reaction solution was diluted with ethyl acetate (50 mL), and washed with water (50 mL) and saturated brine (50 mL) sequentially. The obtained organic phase was dried over anhydrous sodium sulfate, concentrated under reduced pressure, and the residue was purified by silica gel column chromatography (petroleum ether:ethyl acetate=40:1) to obtain compound 11-a (325 mg, yield: 74.9%).

$^1$H NMR (500 MHz, CDCl$_3$) δ: 10.15 (s, 1H), 8.28 (s, 1H), 7.86 (s, 2H), 7.76-7.73 (d, J=15.5 Hz, 1H), 7.58-7.56 (d, J=7.5 Hz, 1H), 7.53-7.50 (d, J=16.0 Hz, 1H), 7.44-7.41 (m, 2H), 7.38-7.34 (m, 1H), 7.11-7.08 (d, J=16.0 Hz, 1H), 6.98-6.96 (d, J=7.0 Hz, 2H), 3.87 (s, 3H), 2.34 (s, 3H) ppm.

Synthesis of Compound 11

To a mixed solution of 11-a (325 mg, 0.82 mmol) and 2-methylserine (195.4 mg, 1.64 mmol) in methanol (10 mL) and dichloromethane (10 mL) was added acetic acid (98.5 mg, 1.64 mmol) at room temperature, and the reaction solution was stirred at room temperature for 1 hour. Then, to the reaction solution was added sodium cyanoborohydride (571.8 mg, 9.1 mmol) and was stirred for 16 hours. After the completion of the reaction, the organic solvent was concentrated by rotary evaporation to dryness, and the residue was dissolved with ethyl acetate (20 mL), followed by washing with water (20 mL) and saturated brine (20 mL) sequentially. The obtained organic phase was dried over anhydrous sodium sulfate, concentrated under reduced pressure, and the residue was purified by silica gel thin layer chromatography preparative plate (dichloromethane:methanol=10:1) to obtain compound 11 (76 mg, yield: 24.6%). LC-MS (ESI): m/z=498.0 [M–H]⁺.

¹H NMR (500 MHz, CD₃OD) δ: 8.16 (s, 1H), 7.80-7.78 (d, J=7.5 Hz, 1H), 7.68-7.62 (m, 2H), 7.54-7.53 (d, J=7.5 Hz, 1H), 7.34-7.32 (m, 2H), 7.29-7.18 (m, 4H), 7.02-7.00 (m, 1H), 4.33-4.25 (m, 2H), 4.01-3.99 (d, J=2.0 Hz, 1H), 3.85-3.83 (d, J=12.5 Hz, 1H), 3.86 (s, 3H), 2.35 (s, 3H), 1.55 (s, 3H) ppm.

Example 12

(E)-2-(3-(3-(2,3-dihydrobenzo[b][1,4]dioxin-6-yl)-2-methylstyryl)-4-fluorobenzylamino)-3-hydroxypropanoic acid (Compound 12)

Synthesis Route:

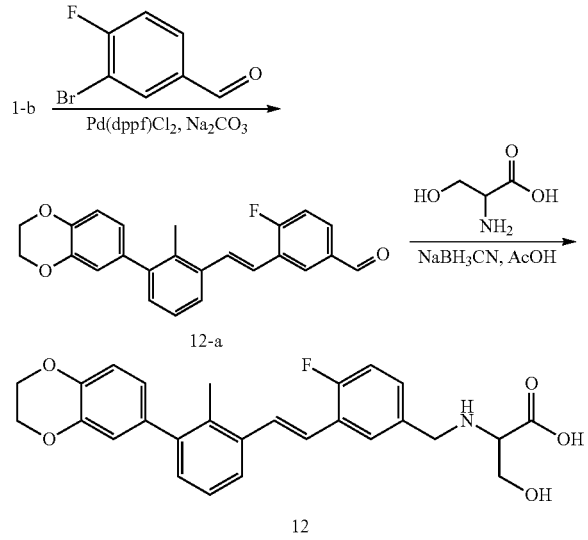

Synthesis of Compound 12-a

To a solution of 3-bromo-4-fluorobenzaldehyde (161 mg, 0.79 mmol) and 1-b (300 mg, 0.79 mmol) in 1,4-dioxane (20 mL) and water (2 mL) were added [1,1'-bis (diphenylphosphino)ferrocene]palladium dichloride (57.8 mg, 0.079 mmol) and sodium carbonate (216.2 g, 2.4 mmol) at room temperature, and the reaction solution was heated to 80° C. and stirred under nitrogen for 16 hours. The reaction solution was cooled to room temperature and concentrated under reduced pressure, and the residue was purified by silica gel column chromatography (petroleum ether:ethyl acetate=15:1) to obtain compound 12-a (140 mg, yield: 47%).

Synthesis of Compound 12

To a mixed solution of 12-a (140 mg, 0.37 mmol) and serine (77.7 mg, 0.74 mmol) in methanol (5 mL) and dichloromethane (5 mL) was added acetic acid (0.04 mL, 0.65 mmol) at room temperature, and the reaction solution was stirred at room temperature for 6 hours. Then, to the reaction solution was added sodium cyanoborohydride (70 mg, 1.1 mmol) and was stirred for 18 hours. The reaction solution was concentrated under reduced pressure, and the residue was purified by high performance liquid chromatography (mobile phase: water (10 mM ammonium bicarbonate), acetonitrile; gradient: 30% to 60% (the initial mobile phase was 30% water and 70% acetonitrile, and the final mobile phase was 60% water and 40% acetonitrile, wherein % refers to volume percentage)) to obtain compound 12 (18 mg, yield: 11%). LC-MS (ESI): m/z=464 [M–H]⁺.

¹H NMR (400 MHz, DMSO-d₆) δ: 7.89 (d, J=4.8 Hz, 1H), 7.64 (d, J=6.0 Hz, 1H), 7.57 (d, J=12.8 Hz, 1H), 7.40-7.37 (m, 1H), 7.28-7.22 (m, 2H), 7.16-7.12 (m, 2H), 6.92 (d, J=6.4 Hz, 1H), 6.80 (d, J=2.0 Hz, 1H), 6.77-6.75 (dd, J₁=2.0 Hz, J₂=6.4 Hz, 1H), 4.28 (s, 4H), 4.04-3.93 (q, 2H), 3.69-3.65 (m, 2H), 3.19-3.17 (m, 1H), 2.29 (s, 3H) ppm.

Example 13

(E)-2-(3-(2-(2'-fluoro-2-methylbiphenyl-3-yl)vinyl)-4-(trifluoromethyl)benzylamino)-3-hydroxypropanoic acid (Compound 13)

Synthesis Route:

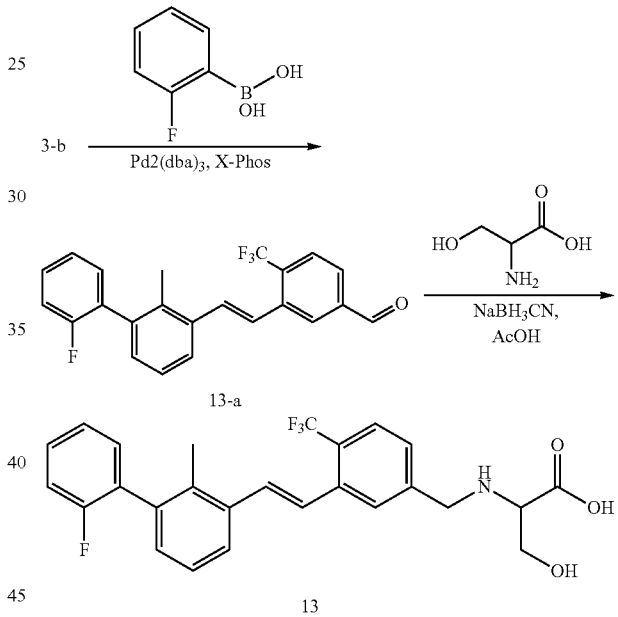

Synthesis of Compound 13-a

To a solution of 2-fluorophenylboronic acid (259 mg, 1.85 mmol) and compound 3-b (500 mg, 1.54 mmol) in toluene (20 mL) were added tris(dibenzylideneacetone)dipalladium (50 mg, 0.05 mmol), 2-dicyclohexylphosphino-2',4',6'-triisopropylbiphenyl (100 mg, 0.21 mmol) and potassium phosphate (983 mg, 4.63 mmol) at room temperature, and the reaction solution was heated to 90° C. and stirred overnight under nitrogen. After the completion of the reaction, the reaction solution was diluted with ethyl acetate (50 mL), and washed with water (50 mL) and saturated brine (50 mL) sequentially. The obtained organic phase was dried over anhydrous sodium sulfate, concentrated under reduced pressure, and the residue was purified by silica gel column chromatography (petroleum ether:ethyl acetate=100:1) to obtain 13-a (250 mg, yield: 42%) as a yellow solid. LC-MS (ESI): m/z=385 [M–H]⁺.

Synthesis of Compound 13

To a mixed solution of 13-a (125 mg, 0.33 mmol) and serine (68 mg, 0.65 mmol) in methanol (10 mL) and dichloromethane (10 mL) was added acetic acid (0.04 mL, 0.65 mmol) at room temperature, and the reaction solution was stirred at room temperature for 2 hours. Then, to the reaction solution was added sodium cyanoborohydride (82 mg, 1.3 mmol) and was stirred for 16 hours. The reaction solution was concentrated under reduced pressure, and the residue was purified by high performance liquid chromatography (mobile phase: water (10 mM ammonium bicarbonate), acetonitrile; gradient: 40% to 70% (the initial mobile phase was 40% water and 60% acetonitrile, and the final mobile phase was 70% water and 30% acetonitrile, wherein % refers to volume percentage)) to obtain compound 13 (13 mg, yield: 8.3%). LC-MS (ESI): m/z=474 [M−H]+.

$^1$H NMR (400 MHz, DMSO-$d_6$) δ: 8.07 (s, 1H), 7.75-7.74 (m, 1H), 7.64-7.52 (m, 4H), 7.36-7.20 (m, 6H), 4.06-3.96 (m, 2H), 3.68-3.64 (m, 2H), 3.22-3.18 (m, 1H), 2.21 (s, 3H) ppm.

Example 14

(S,E)-2-(3-(3-(5-fluoro-2,3-dihydrobenzo[b][1,4]dioxin-6-yl)-2-methylstyryl)-4-methylbenzylamino)-3-hydroxypropanoic acid (Compound 14)

Synthesis Route:

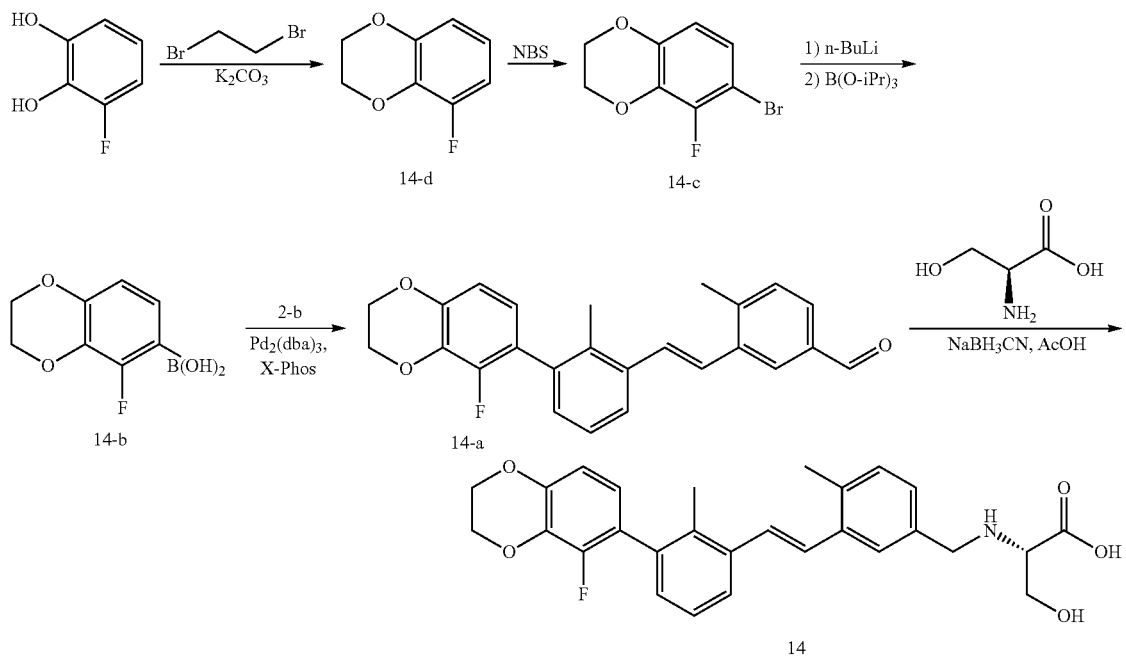

Synthesis of Compound 14-d

3-Fluorocatechol (2 g, 15.63 mmol) was dissolved in N,N-dimethylformamide (10 mL), and anhydrous potassium carbonate (6.5 g, 46.89 mmol) and 1,2-dibromoethane (14.7 g, 78.15 mmol) were added. The reaction mixture was heated to 80° C. and stirred for 24 hours. After the reaction mixture was cooled to room temperature, the reaction mixture was poured into ice water (100 mL), and extracted with petroleum ether (100 mL×2). The organic phase was dried over anhydrous sodium sulfate, filtered, and the filtrate was concentrated under reduced pressure to obtain 14-d as a light brown oil (2.3 g, yield: 95.8%). No further purification was required to this product.

Synthesis of Compound 14-c

Compound 14-d (2.3 g, 14.93 mmol) was dissolved in N,N-dimethylformamide (20 mL). After the mixture was cooled to 0° C., to the mixture was added N-bromosuccinimide (2.64 g, 14.93 mmol) in 10 portions. After the reaction mixture was stirred at room temperature for 16 hours, the reaction mixture was poured into ice water (200 mL), extracted with ethyl acetate (200 mL×2). The organic phase was separated, dried over anhydrous sodium sulfate, filtered, the filtrate was concentrated under reduced pressure, and the residue was purified by silica gel column chromatography (petroleum ether:ethyl acetate=50:1) to obtain 14-c (2.5 g, yield: 73%) as a light yellow solid.

$^1$H NMR (500 MHz, CDCl$_3$) δ: 6.96 (dd, 1H), 6.59 (dd, 1H), 4.27-4.32 (m, 4H) ppm.

Synthesis of Compound 14-b

Compound 14-c (2.3 g, 10 mmol) was dissolved in anhydrous tetrahydrofuran (30 mL), and cooled to −70° C., and a 2.5 M solution of n-butyl lithium in n-hexane (6 mL, 15 mmol) was added dropwise. After the reaction solution was stirred for 1 hour, to the reaction solution was added triisopropyl borate (2.7 g, 15 mmol) and continued to be stirred for 1 hour. The reaction solution was warmed to room temperature, followed by addition of 2N hydrochloric acid (20 mL), and stirred for 30 minutes. The reaction solution was extracted with ethyl acetate (100 mL), dried over anhydrous sodium sulfate, filtered, and the filtrate was concentrated under reduced pressure. To the residue was added petroleum ether (20 mL) and vigorously stirred to obtain 14-b (1.2 g, yield: 61%) as a white solid.

$^1$H NMR (500 MHz, DMSO-$d_6$) δ: 7.97 (s, 2H), 6.99 (m, 1H), 6.65 (m, 1H), 4.27 (m, 4H) ppm.

Synthesis of Compound 14-a

Compound 14-b (74 mg, 0.37 mmol) was dissolved in toluene (5 mL), and 2-b (100 mg, 0.31 mmol), tris(dibenzylideneindeneacetone)dipalladium (27 mg, 0.04 mmol), 2-dicyclohexylphosphino-2,4,6-triisopropylbiphenyl (59 mg, 0.13 mmol) and anhydrous potassium phosphate (197 mg, 0.93 mmol) were added. The reaction mixture was heated to 105° C. and stirred for 16 hours under nitrogen. After the reaction mixture was cooled to room temperature, the reaction mixture was concentrated under reduced pressure, and the residue was purified by silica gel column chromatography (petroleum ether:ethyl acetate=10:1) to obtain 14-a (60 mg, yield: 45%) as a yellow solid.

$^1$H NMR (500 MHz, CDCl$_3$) δ: 10.12 (s, 1H), 8.09 (d, J=1 Hz, 1H), 7.69 (dd, J=8 Hz, J=2 Hz, 1H), 7.37 (m, 2H), 7.28 (m, 1H), 7.17 (m, 2H), 6.78 (m, 1H), 6.70 (m, 2H), 4.34 (m, 4H), 2.51 (s, 3H), 2.28 (s, 3H) ppm.

Synthesis of Compound 14

Compound 14-a (60 mg, 0.14 mmol) and L-serine (29 mg, 0.27 mmol) was dissolved in a mixed solution of tetrahydrofuran (3 mL), ethanol (3 mL) and water (3 mL), and sodium hydroxide (22 mg, 0.54 mmol) was added, and the reaction solution was stirred at 25° C. for 18 hours. Then, to the reaction solution was added sodium borohydride (20 mg, 0.53 mmol) and was stirred for half an hour. The reaction solution was concentrated under reduced pressure, and the pH of the residue was adjusted to 5 with 0.5 M hydrochloric acid, and then the mixture was extracted with ethyl acetate (50 mL×2). The organic phase was dried over anhydrous sodium sulfate, concentrated under reduced pressure, and the residue was purified by silica gel column chromatography (dichloromethane:methanol=10:1) to obtain compound 14 (10 mg, yield: 14%). LC-MS (ESI): m/z=478 [M−H]$^+$.

$^1$H NMR (500 MHz, CDCl$_3$) δ: 7.39 (s, 2H), 6.89-7.11 (m, 6H), 6.57-6.65 (m, 2H), 4.24 (s, 4H), 3.64-3.81 (br, 4H), 3.17 (br, 2H), 2.17 (s, 3H), 2.11 (s, 3H) ppm.

Example 15

(E)-2-(3-(2-(2',3'-difluoro-2-methylbiphenyl-3-yl)vinyl)-4-(trifluoromethyl)benzylamino)-3-hydroxypropanoic acid (Compound 15)

Synthesis Route:

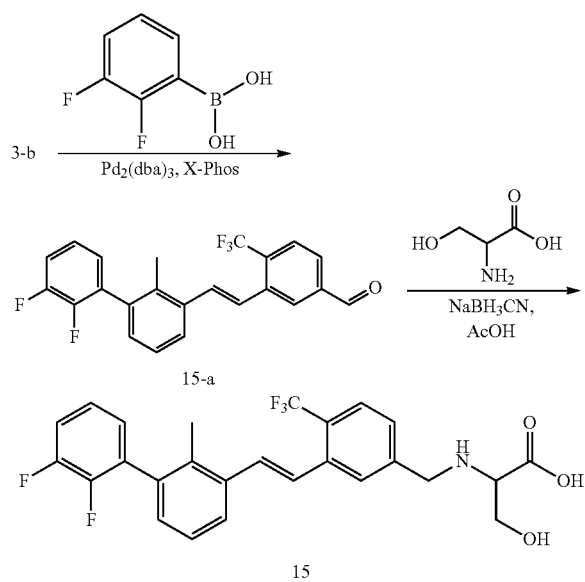

Synthesis of Compound 15-a

To a solution of 2,3-difluorophenylboronic acid (632 mg, 4.0 mmol) and compound 3-b (648 mg, 2.0 mmol) in toluene (30 mL) were added tris(dibenzylideneacetone)dipalladium (183 mg, 0.2 mmol), 2-dicyclohexylphosphino-2',4',6'-triisopropylbiphenyl (200 mg, 0.42 mmol) and potassium phosphate (2120 mg, 10.0 mmol) at room temperature, and the reaction solution was heated to 100° C. and stirred overnight under nitrogen. After the completion of the reaction, the reaction solution was diluted with ethyl acetate (100 mL), and washed with water (100 mL) and saturated brine (100 mL) sequentially. The obtained organic phase was dried over anhydrous sodium sulfate, concentrated under reduced pressure, and the residue was purified by silica gel column chromatography (petroleum ether:ethyl acetate=100:1) to obtain 15-a (300 mg, yield: 37%) as a canary solid.

$^1$H NMR (400 MHz, CD$_3$OD) δ: 10.14 (s, 1H), 8.27 (s, 1H), 7.87 (s, 2H), 7.65 (d, J=6.0 Hz, 1H), 7.50 (d, J=12.4 Hz, 1H), 7.39-7.36 (m, 1H), 7.33 (t, J=6.0 Hz, 1H), 7.22-7.14 (m, 3H), 7.03-7.01 (m, 1H), 2.28 (s, 3H) ppm.

Synthesis of Compound 15

To a mixed solution of 15-a (120 mg, 0.3 mmol) and serine (63 mg, 0.6 mmol) in methanol (10 mL) and dichloromethane (10 mL) was added acetic acid (0.04 mL, 0.65 mmol) at room temperature, and the reaction solution was stirred at room temperature for 2 hours. Then, to the reaction solution was added sodium cyanoborohydride (56.7 mg, 0.9 mmol) and was stirred for 12 hours. The reaction solution was concentrated under reduced pressure, and the residue was purified by high performance liquid chromatography (mobile phase: water (10 mM ammonium bicarbonate), acetonitrile; gradient: 40% to 70% (the initial mobile phase was 40% water and 60% acetonitrile, and the final mobile phase was 70% water and 30% acetonitrile, wherein % refers to volume percentage)) to obtain compound 15 (26 mg, yield: 18%). LC-MS (ESI): m/z=492 [M−H]$^+$.

$^1$H NMR (400 MHz, DMSO-d$_6$) δ: 8.04 (s, 1H), 7.71 (d, J=6.8 Hz, 1H), 7.66 (d, J=6.0 Hz, 1H), 7.59 (d, J=12.8 Hz, 1H), 7.52-7.47 (m, 2H), 7.37 (t, J=6.0 Hz, 1H), 7.34-7.23 (m, 3H), 7.19-7.16 (m, 1H), 4.00 (d, J=12.0 Hz, 1H), 3.88 (d, J=12.0 Hz, 1H), 3.55-3.49 (m, 2H), 2.94 (d, J=4.8 Hz, 1H), 2.22 (s, 3H) ppm.

Example 16

(S,E)-2-(3-(3-(5-fluoro-2,3-dihydrobenzo[b][1,4]dioxin-6-yl)-2-methylstyryl)-4-(trifluoromethyl)benzyl)-3-hydroxypropanoic acid (Compound 16)

Synthesis Route:

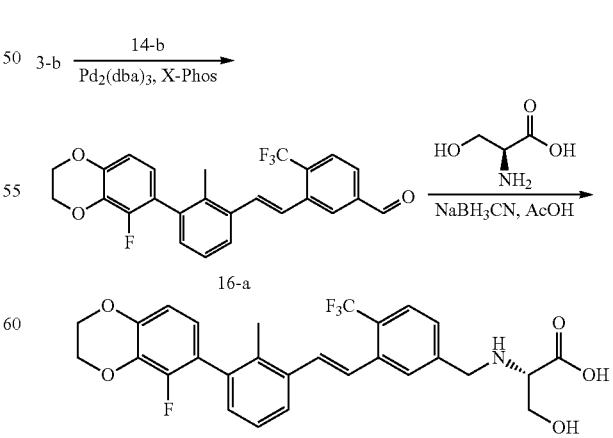

Synthesis of Compound 16-a

Compound 14-b (300 mg, 1.48 mmol) was dissolved in toluene (5 mL), and compound 3-b (400 mg, 1.24 mmol), tris(dibenzylideneindeneacetone)dipalladium (100 mg, 0.11 mmol), 2-dicyclohexylphosphino-2,4,6-triisopropylbiphenyl (100 mg, 0.21 mmol) and anhydrous potassium phosphate (790 mg, 3.72 mmol) were added. The reaction mixture was heated to 105° C. and stirred for 24 hours under nitrogen. After the reaction mixture was cooled to room temperature, the reaction mixture was concentrated under reduced pressure, and the residue was purified by silica gel column chromatography (petroleum ether:ethyl acetate=10:1) to obtain 16-a (360 mg, yield: 66%) as a yellow solid.

Synthesis of Compound 16

Compound 16-a (72 mg, 0.16 mmol) and L-serine (26 mg, 0.26 mmol) were dissolved in a mixed solution of tetrahydrofuran (2 mL), ethanol (2 mL) and water (2 mL), and sodium hydroxide (22 mg, 0.54 mmol) was added, and the reaction solution was stirred at 25° C. for 18 hours. Then, to the reaction solution was added sodium borohydride (20 mg, 0.53 mmol) and was stirred for half an hour. The reaction solution was concentrated under reduced pressure, and the pH of the residue was adjusted to 5 with 0.5 M hydrochloric acid, and the mixture was extracted with ethyl acetate (50 mL×2). The organic phase was dried over anhydrous sodium sulfate and concentrated under reduced pressure. The residue was purified by silica gel thin-layer chromatography preparative plate (dichloromethane:methanol=10:1) to obtain compound 16 (8 mg, yield: 10%). LC-MS (ESI): m/z=532 [M−H]+.

$^1$H NMR (500 MHz, CD$_3$OD) δ: 8.12 (s, 1H), 7.76 (d, J=9 Hz, 1H), 7.57-7.65 (m, 3H), 7.28-7.36 (m, 2H), 7.16 (d, J=8 Hz, 1H), 6.76 (dd, J=9 Hz, J=1 Hz, 1H), 6.69 (m, 1H), 4.35 (s, 4H), 4.31 (d, J=13 Hz, 1H), 4.23 (d, J=13 Hz, 1H), 3.98 (m, 1H), 3.87 (m, 1H), 3.52 (m, 1H), 2.28 (s, 3H) ppm.

Example 17

(E)-2-(3-(2-(2'-fluoro-2-methylbiphenyl-3-yl)vinyl)-4-(trifluoromethyl)benzylamino)-3-hydroxy-2-methylpropanoic acid (Compound 17)

Synthesis Route:

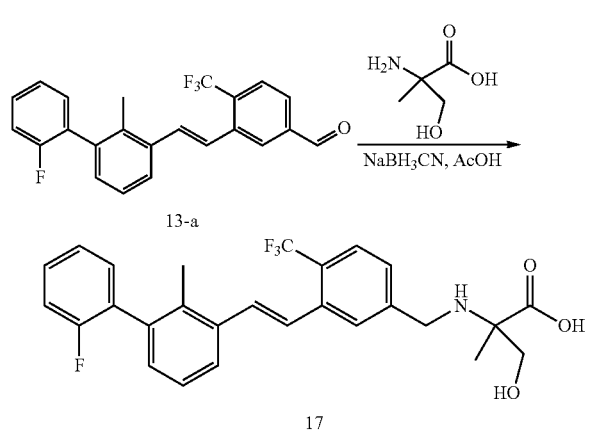

Synthesis of Compound 17

To a mixed solution of 13-a (100 mg, 0.26 mmol) and 2-methylserine (62 mg, 0.52 mmol) in methanol (10 mL) and dichloromethane (10 mL) was added acetic acid (0.03 mL, 0.52 mmol) at room temperature, and the reaction solution was stirred at room temperature for 2 hours. Then, to the reaction solution was added sodium cyanoborohydride (65 mg, 1.04 mmol) and was stirred for 16 hours. The reaction solution was concentrated under reduced pressure, and the residue was purified by high performance liquid chromatography (mobile phase: water (10 mM ammonium bicarbonate), acetonitrile; gradient: 42% to 72% (the initial mobile phase was 42% water and 58% acetonitrile, and the final mobile phase was 72% water and 28% acetonitrile, wherein, % refers to volume percentage) to obtain compound 17 (24 mg, yield: 19%). LC-MS (ESI): m/z=486 [M−H]+.

$^1$H NMR (400 MHz, DMSO-d$_6$) δ: 8.07 (s, 1H), 7.77-7.51 (d, J=7.2 Hz, 1H), 7.64-7.57 (m, 3H), 7.49-7.45 (m, 1H), 7.39-7.26 (m, 6H), 3.99 (s, 2H), 3.60-3.54 (m, 2H), 2.22 (s, 3H), 1.27 (s, 3H) ppm.

Example 18

2-(3-(2-(2-Methylbiphenyl-3-yl)ethyl)-4-(trifluoromethyl)benzylamino)-3-hydroxypropanoic acid (Compound 18)

Synthesis Route:

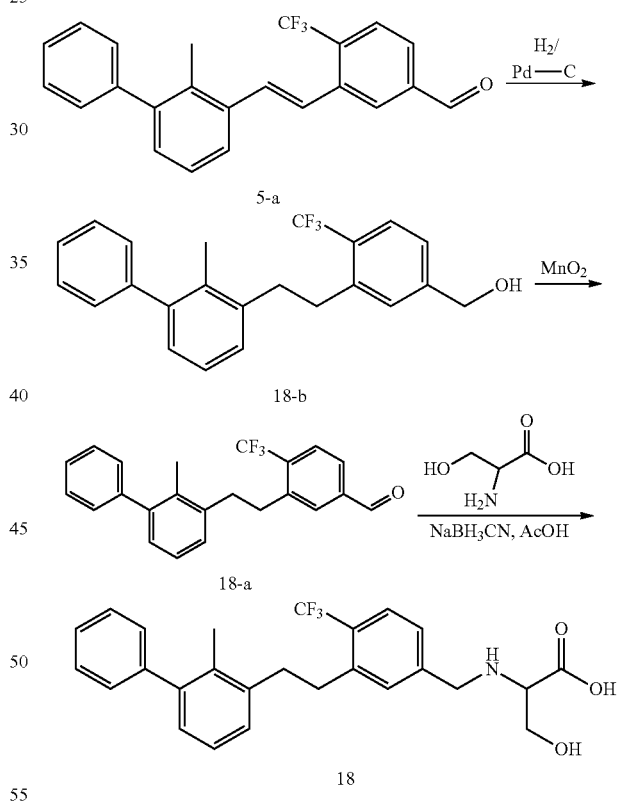

Synthesis of Compound 18-b

Compound 5-a (500 mg, 1.37 mmol) was dissolved in a mixed solution of isopropanol (10 mL) and tetrahydrofuran (20 mL), and to the solution was added 10% palladium-carbon (150 mg) at room temperature, and the reaction was stirred for 12 hours under the atmosphere of hydrogen (1 atm). The reaction solution was filtered, and the filtrate was concentrated under reduced pressure to obtain 18-b (600 mg) as a white solid. The product was directly used in the next step without further purification. LC-MS (ESI): m/z=371 [M+1]+.

Synthesis of Compound 18-a

Compound 18-b (600 mg, 1.62 mmol) was dissolved in dioxane (20 mL), and active manganese dioxide (2.1 g, 24.3 mmol) was added at room temperature. The reaction mixture was stirred at 50° C. for 6 hours. The reaction mixture was filtrated, the filtrate was concentrated under reduced pressure, and the residue was purified by silica gel column chromatography (petroleum ether:ethyl acetate=40:1) to obtain 18-a (300 mg, yield: 50%) as a yellow solid. LC-MS (ESI): m/z=369 [M+H]$^+$.

Synthesis of Compound 18

To a mixed solution of 18-a (100 mg, 0.27 mmol) and serine (57 mg, 0.54 mmol) in methanol (10 mL) and dichloromethane (10 mL) was added acetic acid (0.03 mL, 0.54 mmol) at room temperature, and the reaction solution was stirred at room temperature for 2 hours. Then, to the reaction solution was added sodium cyanoborohydride (68 mg, 1.08 mmol) and was stirred for 16 hours. The reaction solution was concentrated under reduced pressure, and the residue was purified by high performance liquid chromatography (mobile phase: water (10 mM ammonium bicarbonate), acetonitrile; gradient: 40% to 70% (the initial mobile phase was 40% water and 60% acetonitrile, and the final mobile phase is 70% water and 30% acetonitrile, wherein, % refers to volume percentage) to obtain compound 18 (17 mg, yield: 13.8%). LC-MS (ESI): m/z=456 [M-H]$^+$.

$^1$H NMR (400 MHz, DMSO-d$_6$) δ: 7.68-7.67 (m, 1H), 7.58 (s, 1H), 7.46-7.43 (m, 3H), 7.38-7.35 (m, 1H), 7.31-7.29 (m, 2H), 7.22-7.19 (m, 2H), 7.07-7.05 (m, 1H), 4.00-3.98 (d, J=11.2 Hz, 1H), 3.87-3.84 (d, J=11.2 Hz, 1H), 3.62-3.67 (m, 2H), 3.13-3.11 (m, 1H), 2.99-2.92 (m, 4H), 2.17 (s, 3H) ppm.

Example 19

(E)-2-(3-(2-(2-methylbiphenyl-3-yl)vinyl)-4-(trifluoromethyl)benzylamino)-3-hydroxy-2-hydroxymethylpropanoic acid (Compound 19)

Synthesis Route:

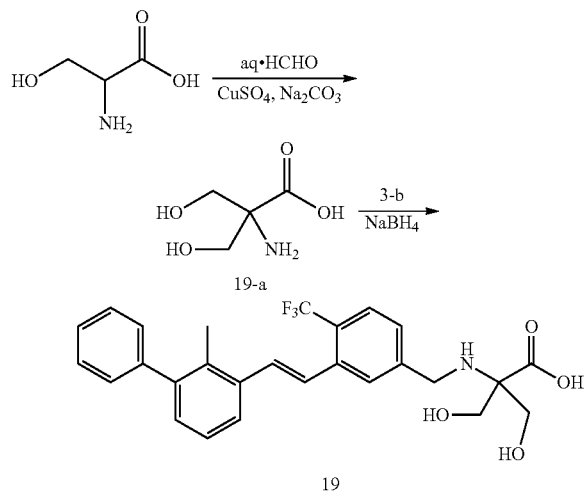

Synthesis of Compound 19-a

To a 500 mL reaction flask were added serine (2.95 g, 28 mmol), anhydrous copper sulfate (0.96 g, 6 mmol), sodium carbonate (11.9 g, 112 mmol), 37% aqueous formaldehyde (20 mL) and 400 mL of water. The mixture was heated to reflux for 2 hours, cooled to room temperature and filtered, and the filtrate was concentrated under reduced pressure. The residue was dissolved with an appropriate amount of water. After the pH of the aqueous solution was adjusted to 3 with 4 M hydrochloric acid, the aqueous solution was purified on a Dowex-50X ion exchange column (6.0 cm×40 cm, 200~400 mesh, hydrogen type). The ion exchange column was first rinsed with water, and rinsed with 250 mL of water after the pH value of the effluent was changed from acidic to neutral, and then the product was eluted with 2M ammonia and detected with ninhydrin chromogenic agent. The effluent which was colored on ninhydrin was collected and concentrated under reduced pressure. To the residue was added anhydrous ethanol (10 mL) and stirred vigorously, filtered, and the filter cake was dried in vacuum to obtain α-(hydroxymethyl) serine (2.2 g, yield: 58%).

$^1$H NMR (500 MHz, CD$_3$OD) δ: 3.90 (d, J=14.0 Hz, 2H), 3.76 (d, J=14.0 Hz, 2H) ppm.

Synthesis of Compound 19

α-(Hydroxymethyl) serine (135 mg, 1 mmol) was dissolved in water (3 mL) and 1 M aqueous sodium hydroxide (2 mL), followed by addition of a mixed solution of compound 3-b (110 mg, 0.3 mmol) in tetrahydrofuran (3 mL) and ethanol (5 mL), and the reaction solution was stirred at room temperature for 16 hours. The reaction solution was cooled to 0° C., followed by addition of sodium borohydride (38 mg, 1 mmol), and further stirred for 1 hour. The reaction solution was concentrated under reduced pressure, and the residue was diluted with water (20 mL), and the pH of which was adjusted to 5 with citric acid. A solid precipitated out and was filtered, and the filter cake was dried to obtain a crude product, which was then recrystallized with ethyl acetate (10 mL) to obtain 19 (20 mg, yield: 14%) as a white solid. LC-MS (ESI): m/z=486 [M-H]$^+$.

$^1$H NMR (500 MHz, CD$_3$OD) δ: 8.18 (s, 1H), 7.79 (d, J=8.0 Hz, 1H), 7.63-7.69 (m, 2H), 7.57 (d, J=8.0 Hz, 1H), 7.44-7.47 (m, 2H), 7.29-7.33 (m, 5H), 7.20 (d, J=8.0 Hz, 1H), 4.38 (s, 2H), 4.01 (d, J=12.0 Hz, 2H), 3.97 (d, J=12.0 Hz, 2H), 2.34 (s, 3H) ppm.

Example 20

(E)-2-(3-(3-(5-fluoro-2,3-dihydrobenzo[b][1,4]dioxin-6-yl)-2-methylstyryl)-4-(trifluoromethyl)benzylamino)-3-hydroxy-2-methylpropanoic acid (Compound 20)

Synthesis Route:

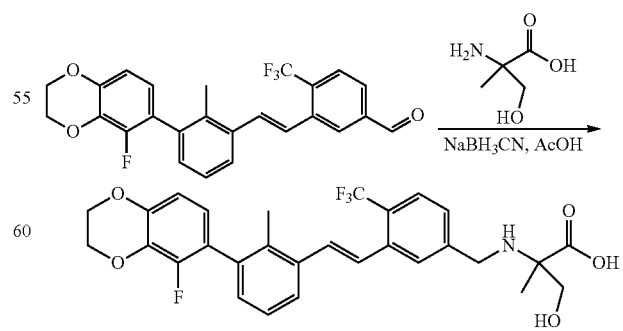

Synthesis of Compound 20

Compound 16-a (80 mg, 0.18 mmol) and 2-methylserine (33 mg, 0.27 mmol) were dissolved in a mixed solution of tetrahydrofuran (2 mL), ethanol (2 mL) and water (2 mL), and sodium hydroxide (22 mg, 0.54 mmol) was added, and the reaction solution was stirred at 25° C. for 18 hours. Then, to the reaction solution was added sodium borohydride (20 mg, 0.53 mmol) and was stirred for half an hour. The reaction solution was concentrated under reduced pressure, and the pH of the residue was adjusted to 5 with 0.5 M hydrochloric acid, and then the mixture was extracted with ethyl acetate (50 mL×2). The organic phase was dried over anhydrous sodium sulfate, concentrated under reduced pressure, and the residue was purified by silica gel thin-layer chromatography preparative plate (dichloromethane:methanol=10:1) to obtain compound 20 (12 mg, yield: 10%). LC-MS (ESI): m/z=546 [M−H]+.

$^1$HNMR (500 MHz, CD$_3$OD) δ: 8.17 (s, 1H), 7.76 (d, J=9 Hz, 1H), 7.58-7.66 (m, 3H), 7.35-7.38 (m, 1H), 7.29-7.33 (m, 1H), 7.17 (d, J=8 Hz, 1H), 6.77 (dd, J$_1$=9 Hz, J$_2$=1 Hz, 1H), 6.69 (m, 1H), 4.38 (m, 2H), 4.35 (s, 4H), 4.10 (d, J=12 Hz, 1H), 3.90 (d, J=12 Hz, 1H), 2.28 (s, 3H), 1.65 (s, 3H) ppm.

Example 21

2-(3-(2-(2-Methylbiphenyl-3-yl)ethyl)-4-(trifluoromethyl)benzylamino)-3-hydroxy-2-methylpropanoic acid (Compound 21)

Synthesis Route:

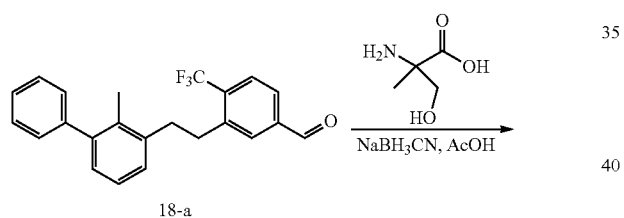

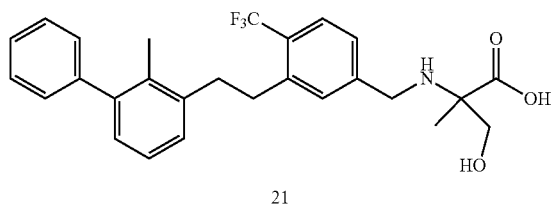

21

Synthesis of Compound 21

To a mixed solution of 18-a (100 mg, 0.27 mmol) and 2-methylserine (65 mg, 0.54 mmol) in methanol (10 mL) and dichloromethane (10 mL) mL, 0.54 mmol) was added acetic acid (0.03 mL, 0.54 mmol) at room temperature, and the reaction solution was stirred at room temperature for 2 hours. Then, to the reaction solution was added sodium cyanoborohydride (68 mg, 1.08 mmol) and was stirred for 16 hours. The reaction solution was concentrated under reduced pressure, and the residue was purified by high performance liquid chromatography (mobile phase: water (10 mM ammonium bicarbonate), acetonitrile; gradient: 40% to 70% (the initial mobile phase was 40% water and 60% acetonitrile, and the final mobile phase was 70% water and 30% acetonitrile, wherein, % refers to volume percentage) to obtain compound 21 (27 mg, yield: 21.3%). LC-MS (ESI): m/z=470 [M−H]+.

$^1$H NMR (400 MHz, DMSO-d$_6$) δ: 7.69-7.68 (d, J=6.4 Hz, 1H), 7.62 (s, 1H), 7.49-7.43 (m, 3H), 7.38-7.35 (m, 1H), 7.31-7.29 (m, 2H), 7.25-7.20 (m, 2H), 7.07-7.05 (m, 1H), 3.94-3.90 (m, 2H), 3.61-3.52 (m, 2H), 2.99-2.92 (m, 4H), 2.17 (s, 3H), 1.24 (s, 3H) ppm.

Example 22

2-(3-(2-(2-Methylbiphenyl-3-yl)ethyl)-4-(trifluoromethyl)benzylamino) propanoic acid (Compound 22)

Synthesis Route:

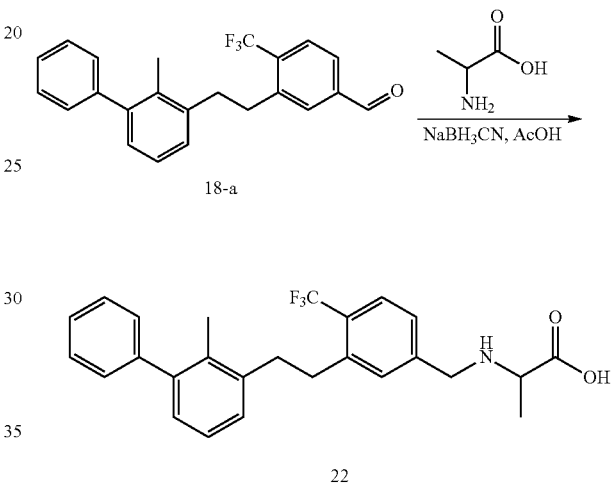

Synthesis of Compound 22

To a mixed solution of 18-a (100 mg, 0.27 mmol) and alanine (44 mg, 0.54 mmol) in methanol (10 mL) and dichloromethane (10 mL) was added acetic acid (0.03 mL, 0.54 mmol) at room temperature, and the reaction solution was stirred at room temperature for 2 hours. Then, to the reaction solution was added sodium cyanoborohydride (68 mg, 1.08 mmol) and was stirred for 16 hours. The reaction solution was concentrated under reduced pressure, and the residue was purified by high performance liquid chromatography (mobile phase: water (10 mM ammonium bicarbonate), acetonitrile; gradient: 40% to 70% (the initial mobile phase was 40% water and 60% acetonitrile, and the final mobile phase was 70% water and 30% acetonitrile, wherein, % refers to volume percentage) to obtain compound 21 (25 mg, yield: 21%). LC-MS (ESI): m/z=440 [M−H]+.

$^1$H NMR (400 MHz, DMSO-d$_6$) δ: 7.68-7.67 (d, J=6.4 Hz, 1H), 7.59 (s, 1H), 7.46-7.43 (m, 3H), 7.38-7.35 (m, 1H), 7.30-7.29 (m, 2H), 7.22-7.19 (m, 2H), 7.07-7.15 (m, 1H), 3.98-3.95 (d, J=11.2 Hz, 1H), 3.85-3.83 (d, J=11.2 Hz, 1H), 3.17-3.15 (m, 1H), 2.99-2.92 (m, 4H), 2.17 (s, 3H), 1.25-1.24 (d, J=5.6 Hz, 3H) ppm.

Example 23

(E)-2-(3-(2-(2',3'-difluoro-2-methylbiphenyl-3-yl)vinyl)-4-(trifluoromethyl)benzylamino)-3-hydroxy-2-methylpropanoic acid (Compound 23)

Synthesis Route:

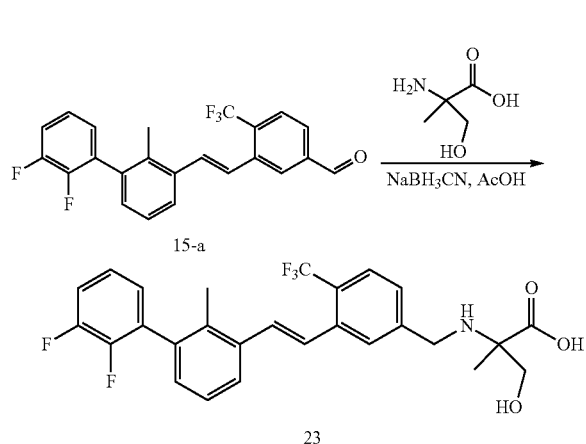

Synthesis of Compound 23

To a mixture of 15-a (120 mg, 0.3 mmol) and 2-methylserine (71.4 mg, 0.6 mmol) in methanol (5 mL) and dichloromethane (5 mL) was added acetic acid (0.04 mL, 0.65 mmol) at room temperature, and the reaction solution was stirred at room temperature for 2 hours. Then, to the reaction solution was added sodium cyanoborohydride (56.7 mg, 0.9 mmol) and was stirred for 12 hours. The reaction solution was concentrated under reduced pressure, and the residue was purified by high performance liquid chromatography (mobile phase: water (10 mM ammonium bicarbonate), acetonitrile; gradient: 42% to 72% (the initial mobile phase was 42% water and 68% acetonitrile, and the final mobile phase was 72% water and 28% acetonitrile, wherein, % refers to volume percentage) to obtain compound 23 (26 mg, yield: 17%). LC-MS (ESI): m/z=506 [M–H]+.

$^1$H NMR (400 MHz, DMSO-d$_6$) δ: 8.19 (s, 1H), 7.81 (d, J=6.4 Hz, 1H), 7.68-7.64 (m, 3H), 7.39-7.21 (m, 5H), 7.12-7.09 (m, 1H), 4.36 (d, J=10.0 Hz, 1H), 4.30 (d, J=10.0 Hz, 1H), 4.02 (d, J=9.2 Hz, 1H), 3.85 (d, J=10.0 Hz, 1H), 2.29 (s, 3H), 1.57 (s, 3H) ppm.

Example 24

(E)-2-((7-(3-(2,3-dihydrobenzo[b][1,4]dioxin-6-yl)-2-methylstyryl)-2,3-dihydrobenzofuran-5-yl)methylamino)-3-hydroxy-2-methylpropanoic acid (Compound 24)

Synthesis Route:

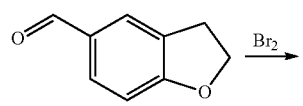

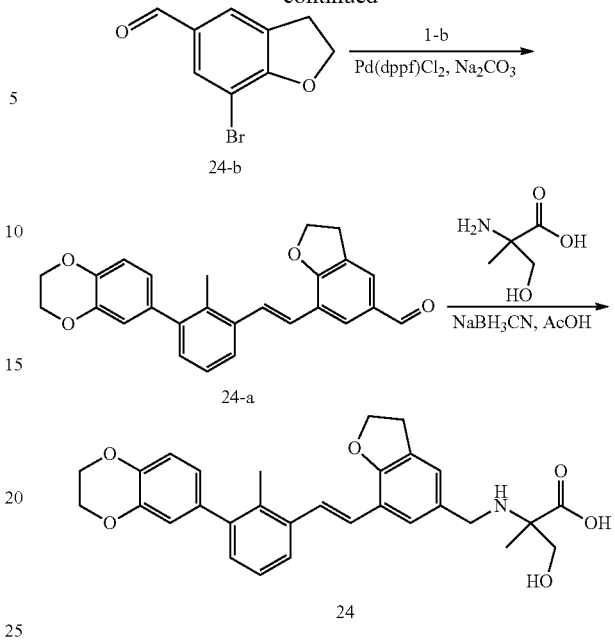

Synthesis of Compound 24-b

Benzodihydrofuran-5-carbaldehyde (2.96 g, 20 mmol) was dissolved in acetic acid (40 mL), and anhydrous sodium acetate (2.1 g, 24 mmol) was added. The reaction mixture was cooled to 10° C., followed by addition of bromine (6.39 g, 40 mmol) dropwise, and then warmed to room temperature and stirred for 16 hours. To the mixture was added ice water (100 mL), and the pH of which was adjusted to 9 to 10 with potassium carbonate. The mixture was extracted with ethyl acetate (100 mL×2), the organic phase was dried over anhydrous sodium sulfate, filtered and concentrated under reduced pressure, and the residue was purified by silica gel column chromatography (petroleum ether:ethyl acetate=10:1) to obtain 24-b (3.8 g, yield: 85%) as a yellow solid.

$^1$H NMR (500 MHz, CDCl$_3$) δ: 9.78 (s, 1H), 7.82 (d, J=1 Hz, 1H), 7.66 (d, J=1 Hz, 1H), 4.79 (t, J=9 Hz, 2H), 3.38 (d, J=9 Hz, 2H) ppm.

Synthesis of Compound 24-a

Compound 24-b (158 mg, 0.69 mmol) was dissolved in dioxane (5 mL) and water (0.5 mL), and compound 1-b (370 mg, 0.97 mmol), 1,1'-bis(diphenylphosphino)ferrocene palladium dichloride (59 mg, 0.07 mmol) and sodium carbonate (219 mg, 2.07 mmol) were added. The reaction mixture was heated to 80° C. and stirred for 16 hours under nitrogen. After the reaction mixture was cooled to room temperature, to the reaction mixture were added dichloromethane (50 mL) and water (50 mL), the organic phase was dried over anhydrous sodium sulfate and concentrated under reduced pressure, and the residue was purified by silica gel column chromatography (petroleum ether:ethyl acetate=3:1) to obtain 16-a (180 mg, yield: 65%) as a yellow solid.

$^1$H NMR (500 MHz, CDCl$_3$) δ: 9.89 (s, 1H), 7.84 (s, 1H), 7.70 (s, 1H), 7.66 (d, J=10 Hz, 1H), 7.57 (d, J=8 Hz, 1H), 7.24 (m, 1H), 7.15 (d, J=7 Hz, 1H), 7.04 (d, J=11 Hz, 1H), 6.91 (d, J=8 Hz, 1H), 6.83 (d, J=2 Hz, 1H), 6.77 (m, 1H), 4.80 (t, J=9 Hz, 2H), 4.31 (s, 4H), 3.31 (d, J=9 Hz, 2H), 2.32 (s, 3H) ppm

Synthesis of Compound 24

Compound 24-a (180 mg, 0.46 mmol) and 2-methylserine (54 mg, 0.92 mmol) were dissolved in a mixed solution of tetrahydrofuran (4 mL), ethanol (4 mL) and water (4 mL), and sodium hydroxide (75 mg, 1.84 mmol) was added and the reaction solution was stirred at 25° C. for 18 hours. Then, to the reaction solution was added sodium borohydride (70 mg, 1.84 mmol) and was stirred for half an hour. The reaction solution was concentrated under reduced pressure, and the pH of the residue was adjusted to 5 with 0.5 M hydrochloric acid, and then the mixture was extracted with ethyl acetate (50 mL×2). The organic phase was dried over anhydrous sodium sulfate, concentrated under reduced pressure, and the residue was purified by silica gel thin-layer chromatography preparative plate (dichloromethane:methanol=10:1) to obtain compound 24 (12 mg, yield: 6%). LC-MS (ESI): m/z=502 [M−H]+.

¹H NMR (500 MHz, CD₃OD) δ: 7.74 (d, J=16 Hz, 1H), 7.56 (m, 1H), 7.48 (m, 1H), 7.29 (m, 1H), 7.21 (m, 1H), 7.08 (m, 1H), 7.03 (m, J=11 Hz, 1H), 6.88 (m, 1H), 6.76 (m, 1H), 4.78 (t, J=9 Hz, 2H), 4.29 (s, 4H), 4.12 (m, 1H), 3.77 (m, 1H), 3.62 (m, 1H), 3.32 (t, J=9 Hz, 2H), 2.29 (s, 3H), 1.49 (s, 3H) ppm.

Example 25

(E)-2-(3-(3-(2,3-dihydrobenzo[b][1,4]dioxin-6-yl)-2-methylstyryl)-4-fluorobenzylamino)-3-hydroxy-2-methylpropanoic acid (Compound 25)

Synthesis Route:

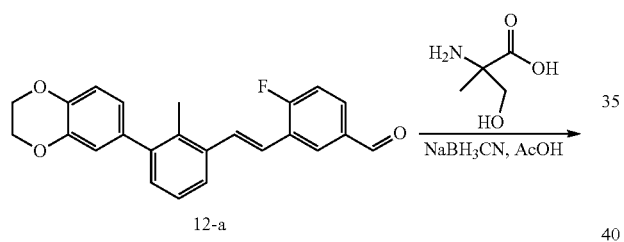

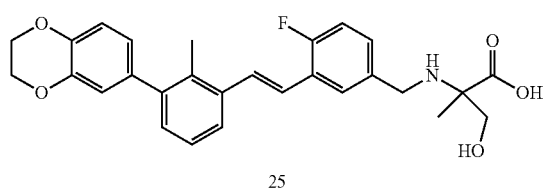

Synthesis of Compound 25

To a mixed solution of 12-a (186 mg, 0.5 mmol) and 2-methylserine (119 mg, 1.0 mmol) in methanol (10 mL) and dichloromethane (10 mL) was added acetic acid (0.04 mL, 0.65 mmol) at room temperature, and the reaction solution was stirred at room temperature for 6 hours. Then, to the reaction solution was added sodium cyanoborohydride (94.5 mg, 1.5 mmol) and was stirred for 18 hours. The reaction solution was concentrated under reduced pressure, and the residue was purified by high performance liquid chromatography (mobile phase: water (10 mM ammonium bicarbonate), acetonitrile; gradient: 35% to 65% (the initial mobile phase was 35% water and 65% acetonitrile, and the final mobile phase was 65% water and 35% acetonitrile, wherein, % refers to volume percentage) to obtain compound 25 (29 mg, yield: 12.1%). LC-MS (ESI): m/z=478 [M−H]+.

¹H NMR (400 MHz, CD₃OD) δ: 7.98 (d, J=4.0 Hz, 1H), 7.68 (d, J=12.8 Hz, 1H), 7.59 (d, J=6.4 Hz, 1H), 7.50-7.47 (m, 1H), 7.26-7.13 (m, 4H), 6.89 (d, J=6.4 Hz, 1H), 6.77-6.73 (m, 2H), 4.29 (s, 4H), 4.26-4.18 (q, 2H), 3.99 (d, J=10 Hz, 1H), 3.83 (d, J=10 Hz, 1H), 2.32 (s, 3H), 1.55 (s, 3H) ppm.

Example 26

(S,E)-2-(3-(3-(5-fluoro-2,3-dihydrobenzo[b][1,4]dioxin-6-yl)-2-methylstyryl)-4-methylbenzylamino)-3-hydroxy-2-methylpropanoic acid (Compound 26)

Synthesis Route:

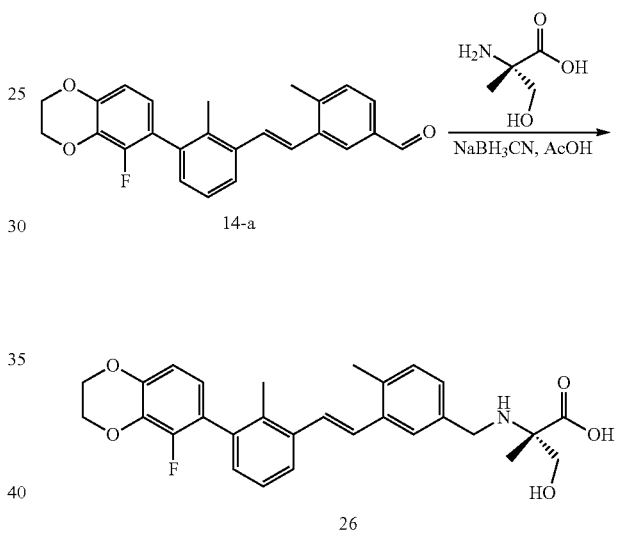

Synthesis of Compound 26

To a mixed solution of 14-a (100 mg, 0.26 mmol) and (S)-2-methylserine (68 mg, 0.52 mmol) in methanol (10 mL) and dichloromethane (10 mL) was added acetic acid (0.03 mL, 0.52 mmol) at room temperature, and the reaction solution was stirred at room temperature for 2 hours. Then, to the reaction solution was added sodium cyanoborohydride (65 mg, 1.03 mmol) and was stirred for 16 hours. The reaction solution was concentrated under reduced pressure, and the residue was purified by high performance liquid chromatography (mobile phase: water (10 mM ammonium bicarbonate), acetonitrile; gradient: 40% to 70% (the initial mobile phase was 40% water and 60% acetonitrile, and the final mobile phase was 70% water and 30% acetonitrile, wherein, % refers to volume percentage) to obtain compound 26 (20 mg, yield: 15.6%). LC-MS (ESI): m/z=490 [M−H]+.

¹H NMR (400 MHz, DMSO-d₆) δ: 7.78 (s, 1H), 7.72-7.03 (d, J=6.0 Hz, 1H), 7.38-7.35 (m, 1H), 7.31-7.25 (m, 3H), 7.23-7.22 (m, 1H), 7.12-7.11 (m, 1H), 6.81-6.79 (m, 1H), 6.73-6.70 (m, 1H), 4.34 (s, 4H), 4.01-3.93 (m, 2H), 3.67-3.65 (m, 1H), 3.59-3.57 (m, 1H), 2.41 (s, 3H), 2.19 (s, 3H), 1.29 (s, 3H) ppm.

Example 27

(R,E)-2-(3-(2-(2-methylbiphenyl-3-yl)vinyl)-4-(trifluoromethyl)benzylamino)-3-hydroxy-2-methylpropanoic acid (Compound 27)

Synthesis Route:

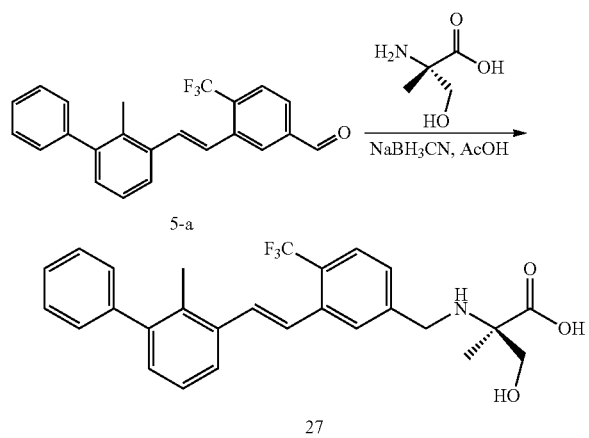

Synthesis of Compound 27

To a mixed solution of 5-a (100 mg, 0.27 mmol) and (R)-2-methylserine (65 mg, 0.54 mmol) in methanol (10 mL) and dichloromethane (10 mL) was added acetic acid (32.8 mg, 0.54 mmol) at room temperature, and the reaction solution was stirred at room temperature for 1 hour. Then, to the reaction solution was added sodium cyanoborohydride (85.8 mg, 1.36 mmol) and was stirred for 16 hours. The reaction solution was concentrated under reduced pressure, and the residue was dissolved in ethyl acetate (50 mL), washed with water (20 mL) and saturated brine (20 mL). The organic phase was dried over anhydrous sodium sulfate, and concentrated under reduced pressure, and the residue was purified by silica gel thin-layer chromatography preparative plate (dichloromethane:methanol=10:1) to obtain compound 27 (24 mg, yield: 18.7%). LC-MS (ESI): m/z=468 [H–H]$^+$.

$^1$H NMR (500 MHz, CD$_3$OD) δ: 8.17 (s, 1H), 7.81-7.79 (d, J=8.5 Hz, 1H), 7.68-7.62 (m, 2H), 7.57-7.55 (d, J=8.0 Hz, 1H), 7.46-7.43 (m, 2H), 7.39-7.28 (m, 5H), 7.20-7.19 (d, J=7.0 Hz, 1H), 4.36-4.28 (q, 2H), 4.03-4.00 (d, J=12.5 Hz, 1H), 3.86-3.84 (d, J=12.5 Hz, 1H), 2.33 (s, 3H), 1.57 (s, 3H) ppm.

Example 28

(S,E)-2-(3-(2-(2-methylbiphenyl-3-yl)vinyl)-4-methylbenzylamino)-3-hydroxy-2-methylpropanoic acid (Compound 28)

Synthesis Route:

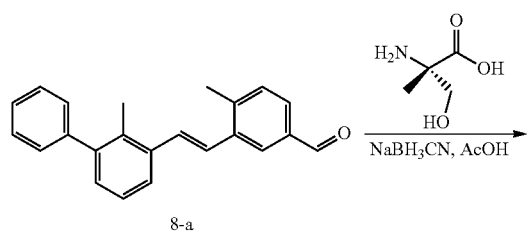

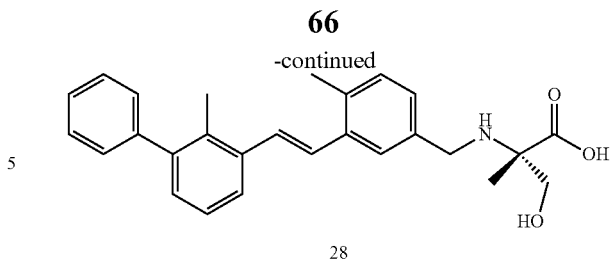

Synthesis of Compound 28

To a mixed solution of 8-a (120 mg, 0.38 mmol) and (S)-2-methylserine (92 mg, 0.77 mmol) in methanol (10 mL) and dichloromethane (10 mL) was added acetic acid (0.034 mL, 0.77 mmol) at room temperature, and the reaction solution was stirred at room temperature for 2 hours. Then, to the reaction solution was added sodium cyanoborohydride (97 mg, 1.53 mmol) and was stirred for 12 hours. The reaction solution was concentrated under reduced pressure, and the residue was purified by high performance liquid chromatography (mobile phase: water (10 mM ammonium bicarbonate), acetonitrile; gradient: 40% to 70% (the initial mobile phase was 40% water and 60% acetonitrile, and the final mobile phase was 70% water and 30% acetonitrile, wherein, % refers to volume percentage) to obtain compound 28 (50 mg, yield: 31.7%). LC-MS (ESI): m/z=414 [M–H]$^+$.

$^1$H NMR (400 MHz, DMSO-d$_6$) δ: 7.78 (s, 1H), 7.69-7.68 (d, J=6.0 Hz, 1H), 7.47-7.44 (m, 2H), 7.39-7.36 (m, 2H), 7.33-7.22 (m, 6H), 7.15-7.14 (m, 1H), 4.01-3.93 (m, 2H), 3.67-3.65 (m, 1H), 3.59-3.58 (m, 1H), 2.41 (s, 3H), 2.27 (s, 3H), 1.29 (s, 3H) ppm.

Example 29

(S,E)-2-(3-(2-(2-methylbiphenyl-3-yl)vinyl)-4-(trifluoromethyl)benzylamino)-3-hydroxy-2-methylpropanoic acid (Compound 29)

Synthesis Route:

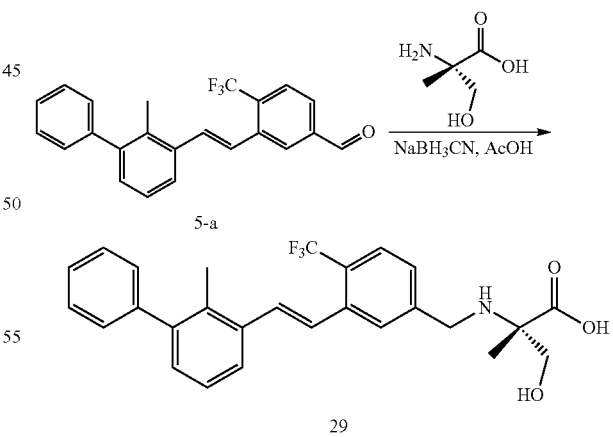

Synthesis of Compound 29

To a mixed solution of 5-a (100 mg, 0.27 mmol) and (S)-2-methylserine (65 mg, 0.54 mmol) in methanol (10 mL) and dichloromethane (10 mL) was added acetic acid (32.8 mg, 0.54 mmol) at room temperature, and the reaction solution was stirred at room temperature for 1 hour. Then, to the reaction solution was added sodium cyanoborohydride (85.8 mg, 1.36 mmol) and was stirred for 16 hours. The reaction solution was concentrated under reduced pressure, and the residue was dissolved in ethyl acetate (50 mL), washed with water (20 mL) and saturated brine (20 mL), and the organic phase was dried over anhydrous sodium sulfate and concentrated under reduced pressure. The residue was purified by silica gel thin-layer chromatography preparative plate (dichloromethane:methanol=10:1) to obtain compound 29 (42 mg, yield: 32.8%). LC-MS (ESI): m/z=468 [H−H]+.

$^1$H NMR (500 MHz, CD$_3$OD) δ: 8.05 (s, 1H), 7.68-7.67 (d, J=8.0 Hz, 1H), 7.56-7.50 (m, 2H), 7.45-7.44 (d, J=7.5 Hz, 1H), 7.34-7.31 (m, 2H), 7.27-7.16 (m, 5H), 7.08-7.07 (d, J=7.0 Hz, 1H), 4.24-4.15 (q, 2H), 3.90-3.88 (d, J=12.0 Hz, 1H), 3.74-3.71 (d, J=12.0 Hz, 1H), 2.21 (s, 3H), 1.45 (s, 3H) ppm.

Example 30

(S,E)-2-(3-(3-(5-fluoro-2,3-dihydrobenzo[b][1,4]dioxin-6-yl)-2-methylstyryl)-4-methylbenzylamino)-3-hydroxy-2-methylpropanoic acid (Compound 30)

Synthesis Route:

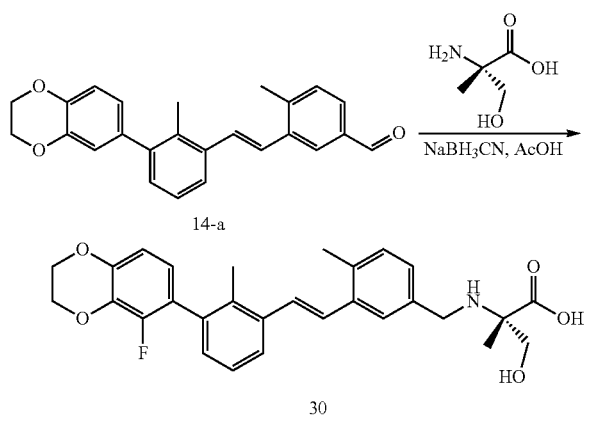

Synthesis of Compound 30

To a mixed solution of 14-a (100 mg, 0.26 mmol) and (S)-2-methylserine (69 mg, 0.52 mmol) in methanol (10 mL) and dichloromethane (10 mL) was added acetic acid (0.03 mL, 0.52 mmol) at room temperature, and the reaction solution was stirred at room temperature for 2 hours. Then, to the reaction solution was added sodium cyanoborohydride (65 mg, 1.03 mmol) and was stirred for 12 hours. The reaction solution was concentrated under reduced pressure, and the residue was purified by high performance liquid chromatography (mobile phase: water (10 mM ammonium bicarbonate), acetonitrile; gradient: 40% to 70% (the initial mobile phase was 40% water and 60% acetonitrile, and the final mobile phase was 70% water and 30% acetonitrile, wherein, % refers to volume percentage) to obtain compound 30 (40 mg, yield: 31.3%). LC-MS (ESI): m/z=490 [M−H]+.

$^1$H NMR (400 MHz, DMSO-d$_6$) δ: 7.79 (s, 1H), 7.72-7.71 (d, J=6.0 Hz, 1H), 7.39-7.35 (m, 1H), 7.31-7.26 (m, 3H), 7.23-7.21 (m, 1H), 7.13-7.11 (m, 1H), 6.81-6.79 (m, 1H), 6.74-6.70 (m, 1H), 4.34 (s, 4H), 4.00-3.93 (m, 2H), 3.67-3.57 (m, 2H), 2.41 (s, 3H), 2.19 (s, 3H), 1.29 (s, 3H) ppm

Example 31

(S,E)-2-(3-(2-(2-methylbiphenyl-3-yl)vinyl)-4-methylbenzylamino)-3-hydroxy-2-methylpropanoic acid (Compound 31)

Synthesis Route:

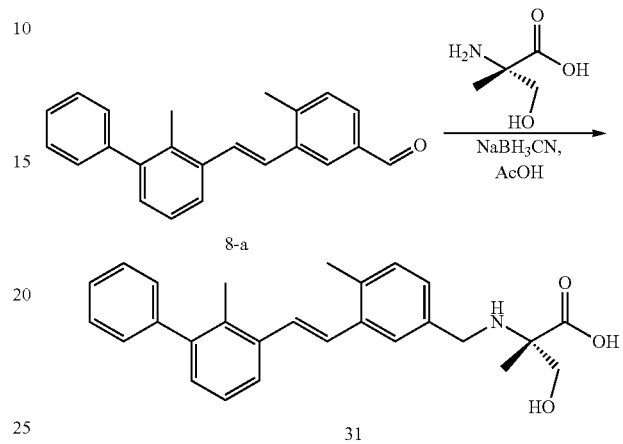

Synthesis of Compound 31

To a mixed solution of 8-a (120 mg, 0.38 mmol) and (S)-2-methylserine (92 mg, 0.77 mmol) in methanol (10 mL) and dichloromethane (10 mL) was added acetic acid (0.04 mL, 0.77 mmol) at room temperature, and the reaction solution was stirred at room temperature for 2 hours. Then, to the reaction solution was added sodium cyanoborohydride (97 mg, 1.53 mmol) and was stirred for 12 hours. The reaction solution was concentrated under reduced pressure, and the residue was purified by high performance liquid chromatography (mobile phase: water (10 mM ammonium bicarbonate), acetonitrile; gradient: 40% to 70% (the initial mobile phase was 40% water and 60% acetonitrile, and the final mobile phase was 70% water and 30% acetonitrile, wherein, % refers to volume percentage) to obtain compound 31 (50 mg, yield: 31.7%). LC-MS (ESI): m/z=414 [M−H]+.

$^1$H NMR (400 MHz, DMSO-d$_6$) δ: 7.78 (s, 1H), 7.69-7.68 (d, J=6.0 Hz, 1H), 7.47-7.44 (m, 2H), 7.39-7.36 (m, 2H), 7.33-7.22 (m, 6H), 7.15-7.14 (m, 1H), 4.01-3.93 (m, 2H), 3.67-3.65 (m, 1H), 3.59-3.58 (m, 1H), 2.41 (s, 3H), 2.27 (s, 3H), 1.29 (s, 3H) ppm.

Example 32

(E)-2-(1-(3-(2-(2-methylbiphenyl-3-yl)vinyl)-4-(trifluoromethyl)phenyl)ethylamino)acetic acid (Compound 32)

Synthesis Route:

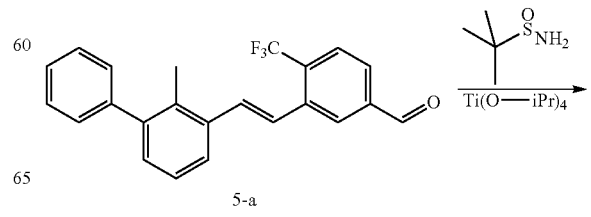

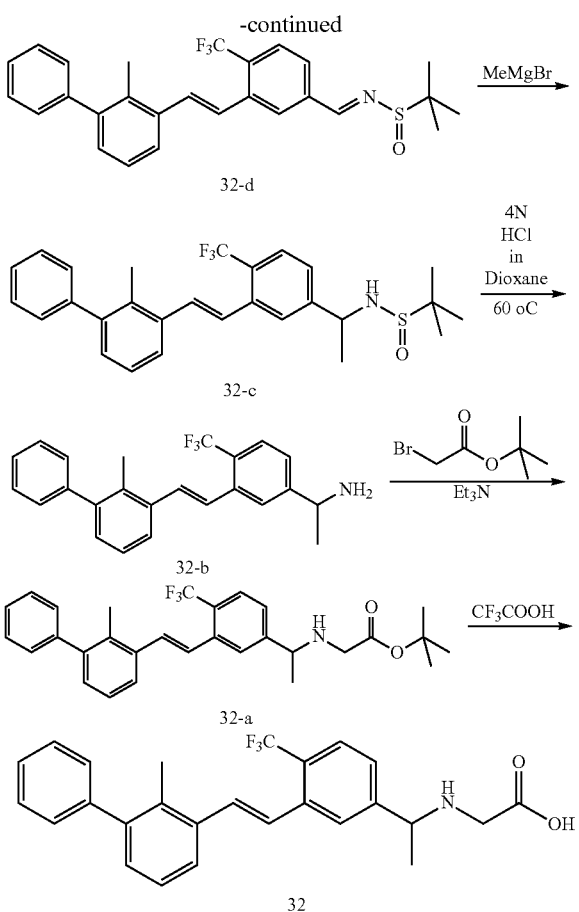

Synthesis of Compound 32-d

Compound 5-a (500 mg, 1.37 mmol) and t-butylsulfinamide (248 mg, 2.05 mmol) were dissolved in tetrahydrofuran (10 mL), and titanium tetraisopropyl (773 mg, 2.74 mmol) was added. After the reaction solution was heated to 60° C. and stirred for 1 hour, the reaction solution was cooled to room temperature. To the reaction solution was added saturated sodium chloride solution (20 mL) and extracted with ethyl acetate (50 mL×3), and the organic phase was dried over anhydrous sodium sulfate, filtered and concentrated under reduced pressure, and the residue was purified by silica gel column chromatography (petroleum ether:ethyl acetate=5:1) to obtain 32-d (610 mg, yield: 95%) as a canary solid.

Synthesis of Compound 32-c

Compound 32-d (610 mg, 1.3 mmol) was dissolved in anhydrous tetrahydrofuran (10 mL), and the mixture was cooled to 0° C., followed by addition of a solution of methylmagnesium bromide in ether (3 M, 0.9 mL, 2.7 mmol). After the completion of the addition, the reaction solution was stirred for 30 minutes. The reaction was quenched with saturated ammonium chloride solution (20 mL) and extracted with ethyl acetate (50 mL), and the organic phase was dried over anhydrous sodium sulfate, filtered and concentrated under reduced pressure, and the residue was washed with tert-butyl methyl ether (50 mL) to obtain 32-c (410 mg, yield: 65%) as a white solid. No further purification was required to the product. LC-MS (ESI): m/z=485 [M+H]$^+$.

Synthesis of Compound 32-b

Compound 32-c (410 mg, 0.85 mmol) was dissolved in methanol (5 mL), and a 4 N solution of hydrogen chloride in dioxane (5 mL) was added, and the reaction solution was heated to 60° C. and stirred for 2 hours. After the reaction solution was cooled to room temperature, the reaction solution was concentrated under reduced pressure, and the residue was washed with petroleum ether (50 mL) to obtain 32-b (320 mg, yield: 91%) as a white solid. No further purification was required to the product. LC-MS (ESI): m/z=382 [M+H]$^+$.

Synthesis of Compound 32-a

Compound 32-b (180 mg, 0.43 mmol) was dissolved in acetonitrile (5 mL), and triethylamine (1 mL) and tert-butyl bromoacetate (92 mg, 0.48 mmol) were added, and the reaction solution was heated to 80° C. and stirred for 3 hours. After the reaction solution was cooled to room temperature, the reaction solution was concentrated under reduced pressure, and the residue was purified by silica gel column chromatography (petroleum ether:ethyl acetate=3:1) to obtain 32-a (60 mg, yield: 28%) as a yellow solid.

Synthesis of Compound 32

Compound 32-a (60 mg, 0.12 mmol) was dissolved in dichloromethane (3 mL), and trifluoroacetic acid (3 mL) was added. After the reaction solution was stirred at room temperature for 3 hours, the reaction solution was concentrated under reduced pressure, and the pH of the residue was adjusted to 5 to 6 with saturated aqueous sodium hydrogen carbonate solution. The mixture was extracted with ethyl acetate (50 mL), and the organic phase was dried over anhydrous sodium sulfate, filtered and concentrated under reduced pressure, and the residue was purified by silica gel thin layer chromatography preparative plate (dichloromethane:methanol=10:1) to obtain 32 (25 mg, yield: 47%) as a white solid. LC-MS (ESI): m/z=440 [M+H]$^+$.

$^1$H NMR (500 MHz, CD$_3$OD) δ: 8.08 (s, 1H), 7.83 (d, J=8 Hz, 1H), 7.64 (d, J=15 Hz, 1H), 7.57 (m, 2H), 7.45 (m, 2H), 7.29-7.38 (m, 5H), 7.21 (d, J=8 Hz, 1H), 4.60 (m, 1H), 3.46 (d, J=16 Hz, 1H), 3.36 (d, J=16 Hz, 1H), 2.34 (s, 3H), 1.73 (d, J=7 Hz, 1H) ppm.

Example 33

(S,E)-2-(3-(2-(2-fluorobiphenyl-3-yl)vinyl)-4-(trifluoromethyl)benzylamino)-3-hydroxy-2-methylpropanoic acid (Compound 33)

Synthesis Route:

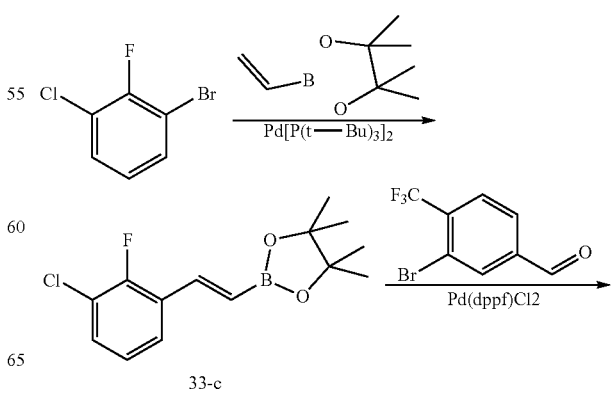

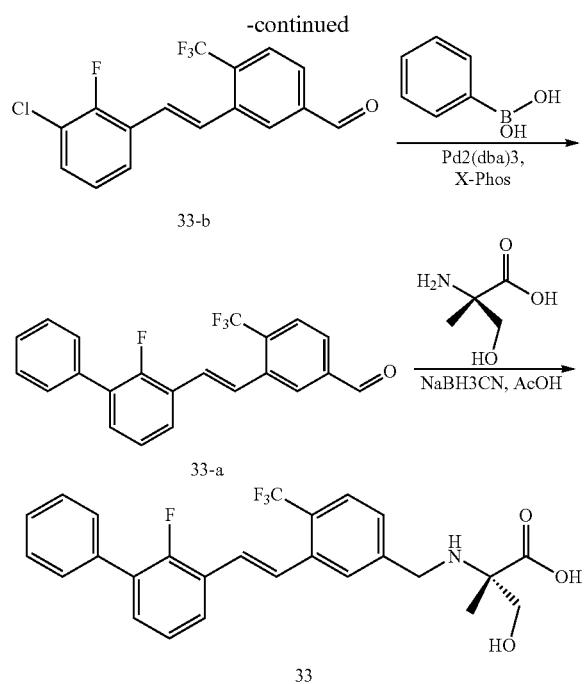

Synthesis of Compound 33-c

To a solution of 1-bromo-3-chloro-2-fluorobenzene (5.0 g, 23.87 mmol) and pinacol vinylboronate (4.47 g, 28.65 mmol) in toluene (100 mL) were added bis(tri-tert-butylphosphine)palladium (853.9 mg, 1.67 mmol) and triethylamine (19.32 g, 190.9 mmol) at room temperature, and the reaction solution was heated to 80° C. and stirred overnight under nitrogen. After the completion of the reaction, the reaction solution was diluted with ethyl acetate (50 mL), washed with water (50 mL) and saturated brine (50 mL). The obtained organic phase was dried over anhydrous sodium sulfate and concentrated under reduced pressure. The residue was purified by silica gel column chromatography (petroleum ether:ethyl acetate=10:1) to obtain compound 33-c (3.45 g, yield: 51.1%).

$^1$H NMR (500 MHz, CDCl$_3$) δ: 7.56-7.52 (d, J=18.5 Hz, 1H), 7.47-7.44 (m, 1H), 7.34-7.30 (m, 1H), 7.07-7.04 (t, 1H), 6.27-6.23 (d, J=18.5 Hz, 1H), 1.32 (s, 12H) ppm.

Synthesis of Compound 33-b

To a solution of 3-bromo-4-trifluoromethylbenzaldehyde (2.57 g, 10.18 mmol) and 33-c (3.45 g, 12.21 mmol) in 1,4-dioxane (40 mL) and water (2 mL) were added [1,1'-bis(diphenylphosphino)ferrocene]palladium dichloride (880 mg, 1.64 mmol) and sodium carbonate (2.69 g, 25.44 mmol) at room temperature, and the reaction solution was heated to 80° C. and stirred overnight under nitrogen. After the completion of the reaction, the reaction solution was diluted with ethyl acetate (50 mL), washed with water (50 mL) and saturated brine (50 mL) sequentially. The obtained organic phase was dried over anhydrous sodium sulfate, concentrated under reduced pressure, and the residue was purified by silica gel column chromatography (petroleum ether:ethyl acetate=40:1) to obtain compound 33-b (1.62 g, yield: 48.5%).

$^1$H NMR (500 MHz, CDCl$_3$) δ: 10.15 (s, 1H), 8.28 (s, 1H), 7.91-7.86 (m, 2H), 7.58-7.55 (m, 1H), 7.53-7.50 (m, 1H), 7.39-7.35 (m, 1H), 7.34-7.31 (d, J=16.5 Hz, 1H), 7.15-7.12 (m, 1H) ppm.

Synthesis of Compound 33-a

To a solution of phenylboronic acid (721.8 mg, 5.92 mmol) and 33-b (300 mg, 1.108 mmol) in toluene (50 mL) were added tris(dibenzylideneacetone) dipalladium (226.2 mg, 0.24 mmol), 2-dicyclohexylphosphino-2',4',6'-triisopropylbiphenyl (470 mg, 0.98 mmol) and potassium phosphate (3.14 g, 14.79 mmol) at room temperature, and the reaction solution was heated to 90° C. and stirred overnight under nitrogen. After the completion of the reaction, the reaction solution was diluted with ethyl acetate (50 mL), and washed with water (50 mL) and saturated brine (50 mL) sequentially. The obtained organic phase was dried over anhydrous sodium sulfate, concentrated under reduced pressure, and the residue was purified by silica gel column chromatography (petroleum ether:ethyl acetate=40:1) to obtain compound 33-a (1.56 g, yield: 85.2%).

$^1$H NMR (500 MHz, CDCl$_3$) δ: 10.14 (s, 1H), 8.31 (s, 1H), 7.89-7.85 (m, 2H), 7.64-7.56 (m, 4H), 7.49-7.39 (m, 5H), 7.28-7.24 (m, 1H) ppm.

Synthesis of Compound 33

To a mixed solution of 33-a (100 mg, 0.27 mmol) and (S)-2-methylserine (64.3 mg, 0.54 mmol) in methanol (10 mL) and dichloromethane (10 mL) was added acetic acid (32.4 mg, 0.54 mmol) at room temperature, and the reaction solution was stirred at room temperature for 1 hour. Then, to the reaction solution was added sodium cyanoborohydride (84.8 mg, 1.35 mmol) and was stirred for 16 hours. After the completion of the reaction, the organic solvent was concentrated by rotary evaporation to dryness, and the residue was dissolved with ethyl acetate (50 mL), followed by washing with water (50 mL) and saturated brine (50 mL) sequentially. The obtained organic phase was dried over anhydrous sodium sulfate and concentrated under reduced pressure, and the residue was purified by silica gel thin layer chromatography preparative plate (dichloromethane:methanol=10:1) to obtain compound 33 (30 mg, yield: 23.6%). LC-MS (ESI): m/z=472 [M−H]$^+$.

$^1$H NMR (400 MHz, CD$_3$OD) δ: 8.17 (s, 1H), 7.79-7.77 (d, J=8.0 Hz, 1H), 7.67-7.59 (m, 3H), 7.56-7.50 (m, 3H), 7.48-7.37 (m, 4H), 7.32-7.28 (m, 1H), 4.35-4.24 (m, 2H), 4.01-3.98 (d, J=12.4 Hz, 1H), 3.84-3.81 (d, J=12.0 Hz, 1H), 1.55 (s, 3H) ppm.

Example 34

(R,E)-2-(3-(2-(2-fluorobiphenyl-3-yl)vinyl)-4-(trifluoromethyl)benzylamino)-3-hydroxy-2-methylpropanoic acid (Compound 34)

Synthesis Route:

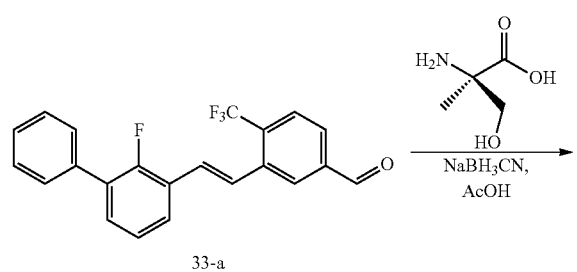

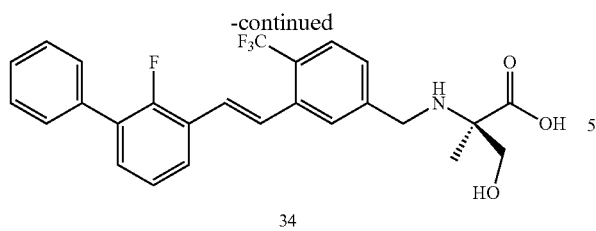

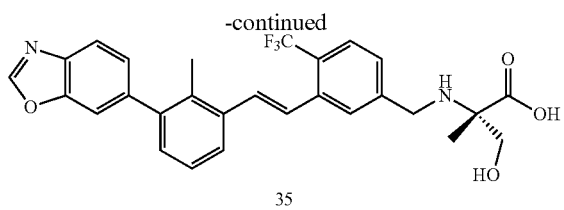

Synthesis of Compound 34

To a mixed solution of 33-a (100 mg, 0.27 mmol) and (R)-2-methylserine (64.3 mg, 0.54 mmol) in methanol (10 mL) and dichloromethane (10 mL) was added acetic acid (32.4 mg, 0.54 mmol) at room temperature, and the reaction solution was stirred at room temperature for 1 hour. Then, to the reaction solution was added sodium cyanoborohydride (84.8 mg, 1.35 mmol) and was stirred for 16 hours. After the completion of the reaction, the organic solvent was concentrated by rotary evaporation to dryness, and the residue was dissolved with ethyl acetate (50 mL), followed by washing with water (50 mL) and saturated brine (50 mL) sequentially. The obtained organic phase was dried over anhydrous sodium sulfate, concentrated under reduced pressure, and the residue was purified by silica gel thin layer chromatography preparative plate (dichloromethane:methanol=10:1) to obtain compound 34 (24 mg, yield: 18.9%). LC-MS (ESI): m/z=472 [M−H]+.

1H NMR (400 MHz, CD3OD) δ: 8.17 (s, 1H), 7.79-7.77 (d, J=8.0 Hz, 1H), 7.67-7.59 (m, 3H), 7.56-7.50 (m, 3H), 7.48-7.37 (m, 4H), 7.32-7.28 (m, 1H), 4.35-4.24 (m, 2H), 4.01-3.98 (d, J=12.4 Hz, 1H), 3.84-3.81 (d, J=12.0 Hz, 1H), 1.55 (s, 3H) ppm.

Example 35

(S,E)-2-(3-(3-(benzo[d]oxazol-6-yl)-2-methylstyryl)-4-(trifluoromethyl)benzylamino)-3-hydroxy-2-methylpropanoic acid (Compound 35)

Synthesis Route:

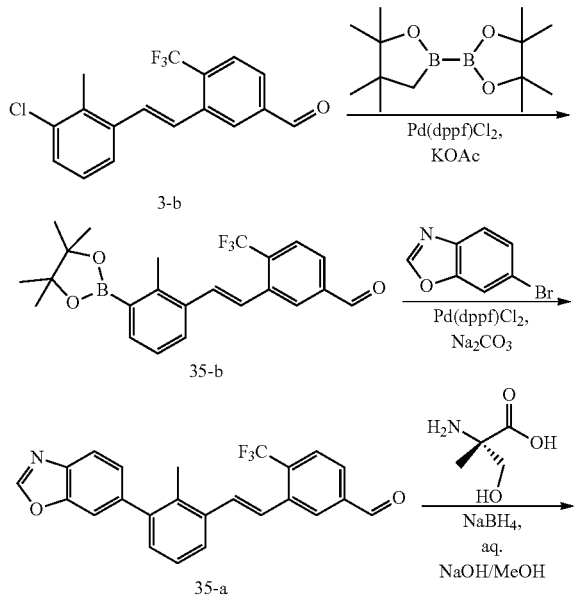

Synthesis of Compound 35-b

To a 100 mL reaction flask were added 3-b (3.24 g, 10 mmol), bis(pinacolato)diboron (3.05 g, 12 mmol), tris (dibenzylideneacetone)dipalladium (458 mg, 0.5 mmol), 2-dicyclohexylphosphino-2',4',6'-triisopropylbiphenyl (952 mg, 2.0 mmol), potassium acetate (3.00 g, 112 mmol) and 80 mL of toluene. The mixture was stirred at 90° C. for 16 hours under nitrogen. The reaction solution was cooled to room temperature, filtered, and the filtrate was concentrated to dryness on a rotary evaporator. The obtained residue was purified by silica gel column chromatography (petroleum ether:ethyl acetate=25:1) to obtain compound 35-b (3.06 g, yield: 82%). 1H NMR (500 MHz, CD3Cl) δ: 10.15 (s, 1H), 8.28 (s, 1H), 7.85 (s, 2H), 7.73-7.76 (m, 1H), 7.62 (d, J=7.5 Hz, 1H), 7.50 (d, J=18 Hz, 1H), 7.26-7.28 (m, 1H), 7.23 (d, J=7.5 Hz, 1H), 2.65 (s, 3H), 1.37 (s, 12H) ppm.

Synthesis of Compound 35-a

To a mixture of 6-bromobenzo[d]oxazole (600 mg, 3.0 mmol) and 35-b (1.00 g, 2.4 mmol) in 1,4-dioxane (20 mL) were added water (3 mL), [1,1'-bis (diphenylphosphino) ferrocene]palladium dichloride (180 mg, 0.24 mmol) and sodium carbonate (636 mg, 6.0 mmol), and the reaction solution was heated to 80° C. and stirred for 16 hours under nitrogen. The reaction solution was concentrated under reduced pressure, and the residue was purified by silica gel column chromatography (petroleum ether:ethyl acetate=25:1) to obtain compound 35-a (700 mg, yield: 72%).

Synthesis of Compound 35

To a 50 mL single-necked bottle were added 3 mL of a solution of (S)-2-methylserine (119 mg, 1 mmol) in water and 2 mL of 1 M aqueous sodium hydroxide solution. After the completion of the addition, to the solution was added 3 mL of solution of 35-a (194 mg, 0.5 mmol) in tetrahydrofuran, followed by addition of 5 mL of methanol to make the mixture homogeneous. After the reaction solution was stirred at room temperature for 16 hours, the reaction solution was cooled in an ice water bath and sodium borohydride (38 mg, 1 mmol) was added. After completion of the addition, the reaction solution continued to be stirred for 1 hour in ice water bath. The solvent was removed by rotary evaporation under reduced pressure, and the residue was diluted with water and the pH of which was adjusted to 5 to 6 with citric acid. The mixture was filtered, and the solid was collected and dried to obtain a crude product. To the crude product was added 10 mL of ethyl acetate, heated to reflux for several minutes, cooled to room temperature and filtered, and the solid was collected and dried to obtain compound 35 (44 mg, 17%) as a white solid product. LC-MS (ESI): m/z=511 (M+H)+.

1H NMR (500 MHz, CD3OD) δ: 8.54 (s, 1H), 8.19 (s, 1H), 7.83 (d, J=8.0 Hz, 1H), 7.81 (d, J=8.0 Hz, 1H), 7.69 (d, J=18.0 Hz, 1H), 7.61-7.63 (m, 3H), 7.33-7.41 (m, 3H), 7.27 (d, J=7.5 Hz, 1H), 4.36 (d, J=12.5 Hz, 1H), 4.30 (d, J=12.5 Hz, 1H), 4.02 (d, J=11.5 Hz, 1H), 3.84 (d, J=11.5 Hz, 1H), 2.36 (s, 3H), 1.57 (s, 3H) ppm.

Example 36

(S,E)-2-(3-(3-imidazo[1,2-a]pyridin-6-yl)-2-methyl-styryl)-4-(trifluoromethyl)benzylamino)-3-hydroxy-2-methylpropanoic acid (Compound 36)

Synthesis Route:

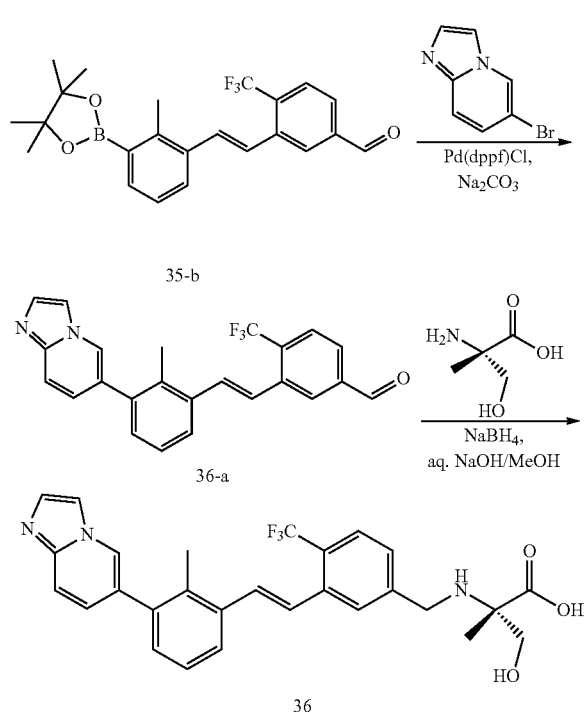

Synthesis of Compound 36-a

To a solution of 6-bromoimidazo[1,2-a]pyridine (197 mg, 1.0 mmol) and 35-b (416 mg, 1.0 mmol) in 1,4-dioxane (20 mL) were added water (3 mL), [1,1'-bis(diphenylphosphino)ferrocene]palladium dichloride (73 mg, 0.1 mmol) and sodium carbonate (318 mg, 3.0 mmol) at room temperature. The reaction solution was heated to 80° C. and stirred for 16 hours under nitrogen. The reaction solution was concentrated under reduced pressure, and the residue was purified by silica gel column chromatography (petroleum ether:ethyl acetate=3:1) to obtain compound 36-a (280 mg, yield: 69%).

Synthesis of Compound 36

To 30 mL of a suspension of (S)-2-methylserine (238 mg, 2.0 mmol) and 36-a (203 mg, 0.5 mmol) in methanol was added 6 mL of a solution of sodium hydroxide (80 mg, 2.0 mmol) in water under stirring. The mixture became a clear homogeneous system and was stirred at room temperature for 3 hours, and then cooled to 0° C. To the mixture was added sodium borohydride (38 mg, 1.0 mmol) at 0° C., and after the completion of the addition, the reaction solution was warmed to room temperature naturally and continued to be stirred for 2 hours. The methanol was removed by rotary evaporation under reduced pressure, and the residue was diluted with 10 mL of water and the pH of which was adjusted to 7 with citric acid. 10 mL of ethyl acetate was added and the mixture was stirred for 10 minutes. The mixture was filtered, and the solid was collected and dried to obtain the product 36 (68 mg, 26%). LC-MS (ESI): m/z=510 (M+H)$^+$.

$^1$H NMR (500 MHz, CD$_3$OD) δ: 8.45 (s, 1H), 8.17 (s, 1H), 7.91 (m, 1H), 7.79 (m, 1H), 7.62-7.68 (m, 5H), 7.30-7.38 (m, 4H), 4.29 (d, J=10 Hz, 1H), 4.24 (d, J=10 Hz, 1H), 3.97 (d, J=11 Hz, 1H), 3.83 (d, J=11 Hz, 1H), 2.40 (s, 3H), 1.54 (s, 3H) ppm.

Example 37

(S,E)-2-(3-(3-imidazo[1,2-a]pyrazin-6-yl)-2-methyl-styryl)-4-(trifluoromethyl)benzylamino)-3-hydroxyl-2-methylpropanoic acid (Compound 37)

Synthesis Route:

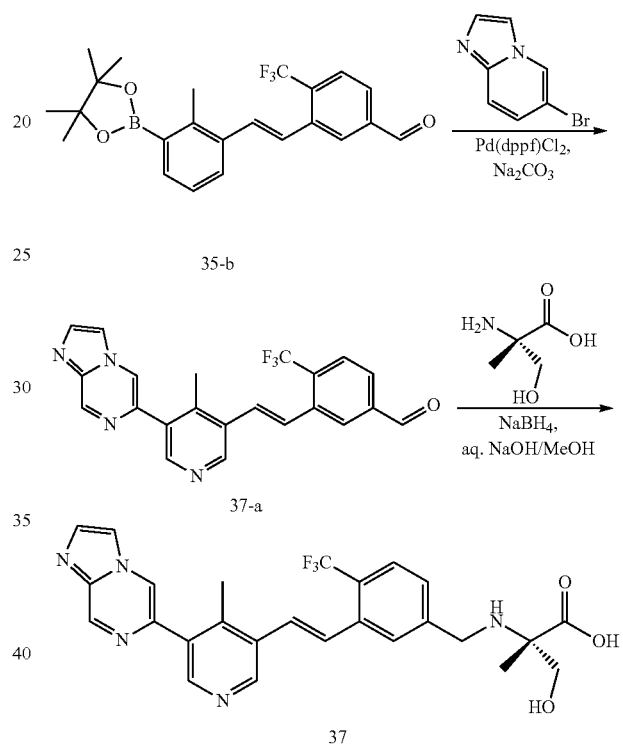

Synthesis of Compound 37-a

To a solution of 6-bromoimidazo[1,2-a]pyridine (198 mg, 1.0 mmol) and 35-b (416 mg, 1.0 mmol) in 1,4-dioxane (20 mL) were added water (3 mL), [1,1'-bis(diphenylphosphino)ferrocene]palladium dichloride (73 mg, 0.1 mmol) and sodium carbonate (270 mg, 2.5 mmol) at room temperature. The reaction mixture was heated to 80° C. and stirred for 16 hours under nitrogen. The reaction mixture was concentrated under reduced pressure, and the residue was purified by silica gel column chromatography (petroleum ether:ethyl acetate=6:1) to obtain compound 37-a (95 mg, yield: 23%). LC-MS (ESI): m/z=408 (M+H)$^+$.

Synthesis of Compound 37

To 20 mL of a suspension of (S)-2-methylserine (119 mg, 1.0 mmol) and 37-a (81 mg, 0.2 mmol) in methanol was added 5 mL of a solution of sodium hydroxide (40 mg, 1.0 mmol) in water under stirring. The mixture became a clear homogeneous system and was stirred at room temperature for 3 hours, and then cooled to 0° C. To the mixture was added sodium borohydride (19 mg, 0.5 mmol) at 0° C., and after the completion of the addition, the reaction solution was warmed to room temperature naturally and continued to be stirred for 2 hours. The methanol was removed by rotary evaporation under reduced pressure, and the residue was diluted with 10 mL of water and the pH of which was adjusted to 7 with citric acid. 10 mL of ethyl acetate was added and the mixture was stirred for 10 minutes. The mixture was filtered, and the solid was collected and dried to obtain the product 37 (33 mg, yield: 32%). LC-MS (ESI): m/z=511 (M+H)$^+$.

$^1$H NMR (500 MHz, CD$_3$OD) δ: 9.10 (s, 1H), 8.64 (s, 1H), 8.20 (s, 1H), 8.15 (s, 1H), 7.91 (s, 1H), 7.80 (d, J=8 Hz, 1H), 7.64-7.71 (m, 3H), 7.34-7.43 (m, 3H), 4.37 (d, J=12 Hz, 1H), 4.31 (d, J=12 Hz, 1H), 4.02 (d, J=12 Hz, 1H), 3.86 (d, J=12 Hz, 1H), 2.43 (s, 3H), 1.58 (s, 3H) ppm.

Example 38

(S,E)-2-(3-(3-(benzo[d]isoxazol-6-yl)-2-methyl-styryl)-4-(trifluoromethyl)benzylamino)-3-hydroxy-2-methylpropanoic acid (Compound 38)

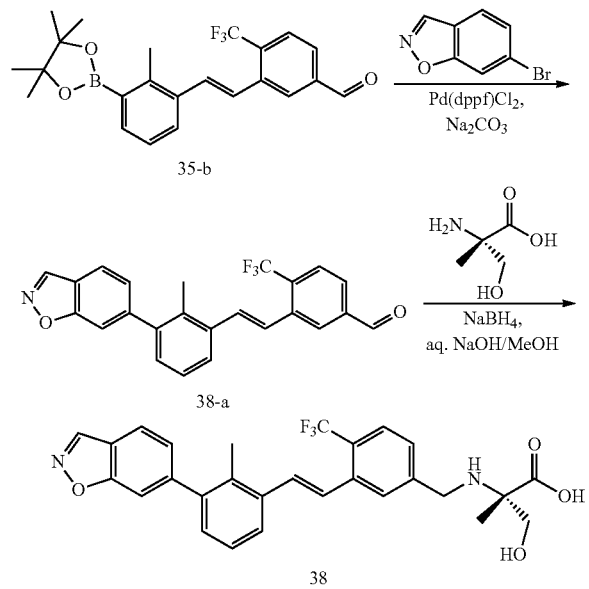

Synthesis of Compound 38-a

To a solution of 6-bromobenzo[d]isoxazole (198 mg, 1.0 mmol) and 35-b (416 mg, 1.0 mmol) in 1,4-dioxane (20 mL) were added water (3 mL), [1,1'-bis(diphenylphosphino)ferrocene]palladium dichloride (73 mg, 0.1 mmol) and sodium carbonate (270 mg, 2.5 mmol) at room temperature. The reaction mixture was heated to 80° C. and stirred for 16 hours under nitrogen. The reaction mixture was concentrated under reduced pressure, and the residue was purified by silica gel column chromatography (petroleum ether:ethyl acetate=6:1) to obtain compound 37-a (86 mg, yield: 21%). LC-MS (ESI): m/z=408 (M+H)$^+$.

Synthesis of Compound 38

To 20 mL of a suspension of (S)-2-methylserine (48 mg, 0.4 mmol) and 38-a (82 mg, 0.2 mmol) in methanol was added 4 mL of a solution of sodium hydroxide (20 mg, 0.5 mmol) in water under stirring. The mixture became a clear homogeneous system and was stirred at room temperature for 3 hours, and then cooled to 0° C. To the mixture was added sodium borohydride (23 mg, 0.6 mmol) at 0° C., and after the completion of the addition, the reaction solution was warmed to room temperature naturally and continued to be stirred for 2 hours. The methanol was removed by rotary evaporation under reduced pressure, and the residue was diluted with 10 mL of water and the pH of which was adjusted to 5 to 6 with citric acid. 10 mL of ethyl acetate was added and the mixture was stirred for 10 minutes. The mixture was filtered, and the solid was collected and dried to obtain the product 38 (12 mg, yield: 12%). LC-MS (ESI): m/z=511 (M+H)$^+$.

$^1$H NMR (500 MHz, CD$_3$OD) δ: 8.17 (s, 1H), 7.80 (d, J=8 Hz, 1H), 7.59-7.87 (m, 5H), 7.31-7.37 (m, 2H), 7.19 (d, J=7.5 Hz, 1H), 6.89-6.91 (m, 2H), 4.33 (d, J=12 Hz, 1H), 4.27 (d, J=12 Hz, 1H), 4.00 (d, J=12 Hz, 1H), 3.84 (d, J=12 Hz, 1H), 2.34 (s, 3H), 1.56 (s, 3H) ppm.

Example 39

(S,E)-3-hydroxy-2-methyl-2-(3-(2-methyl-3-(pyridin-2-yl)styryl)-4-(trifluoromethyl)benzylamino)propanoic acid (Compound 39)

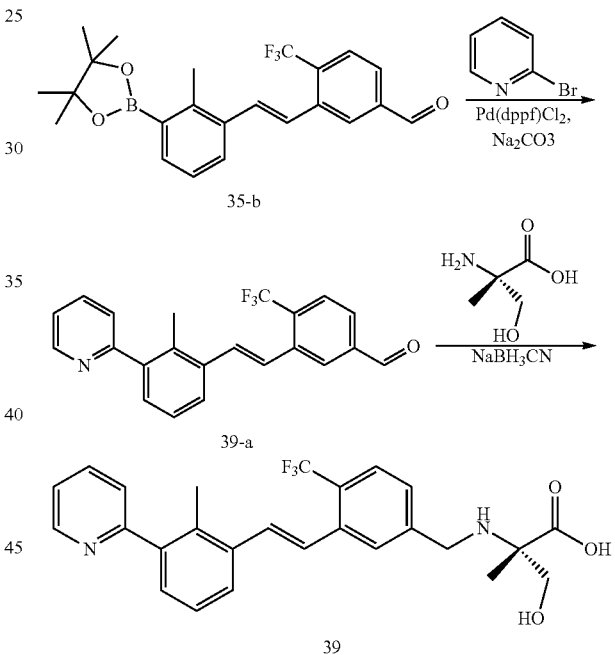

Synthesis of Compound 39-a

2-Bromopyridine (158 mg, 1.00 mmol) and 35-b (500.0 mg, 1.20 mmol) were dissolved in a mixture of 1,4-dioxane and water (20 mL, the volume ratio of 1,4-dioxane to water was 20:1), and [1,1'-bis(diphenylphosphino)ferrocene] palladium dichloride (86.5 mg, 0.10 mmol) and sodium carbonate (814.6 mg, 2.50 mmol) were added. The reaction solution was heated to 80° C. and stirred overnight under nitrogen. After the completion of the reaction, the reaction solution was diluted with ethyl acetate, washed with water three times and saturated brine once. The obtained organic phase was dried over anhydrous sodium sulfate, and concentrated by rotary evaporation to dryness to obtain a crude compound. The crude compound was purified by preparative plate (PE/EA=5:1) to obtain the target compound 39-a (90 mg, yield: 24%).

Synthesis of Compound 39

To a mixed solution of 39-a (105 mg, 0.29 mmol) and (S)-2-methylserine (68 mg, 0.57 mmol) in methanol and dichloromethane (10 mL, the volume ratio of methanol to dichloromethane was 1:1) was added acetic acid (34 mg, 0.57 mmol), and the reaction solution was stirred at room temperature for 1 hour. Then, to the reaction solution was added sodium cyanoborohydride (90 mg, 1.43 mmol) and was stirred overnight. After the completion of the reaction, the solvent was concentrated by rotary evaporation to dryness to obtain a crude compound. The crude compound was purified by preparative plate (DCM:MeOH=15:1) to obtain the target compound 39 (34 mg, yield: 25%). LC-MS (ESI): m/z=471.0 [M+H]$^+$.

$^1$H NMR (500 MHz, CD$_3$OD) δ: 8.64-8.63 (d, J=5.0 Hz, 1H), 8.19 (s, 1H), 7.99-7.96 (m, 1H), 7.82-7.80 (d, J=7.5 Hz, 1H), 7.70-7.64 (m, 3H), 7.54 (d, J=7.0 Hz, 1H), 7.48-7.46 (m, 1H), 7.40-7.32 (m, 3H), 4.37 (d, J=12 Hz, 1H), 4.29 (d, J=12 Hz, 1H), 4.02 (d, J=12 Hz, 1H), 3.85 (d, J=12 Hz, 1H), 2.36 (s, 3H), 1.57 (s, 3H) ppm.

Example 40

(S,E)-3-hydroxy-2-methyl-2-(3-(2-methyl-3-(pyridin-3-yl)styryl)-4-(trifluoromethyl)benzylamino)propanoic acid (Compound 40)

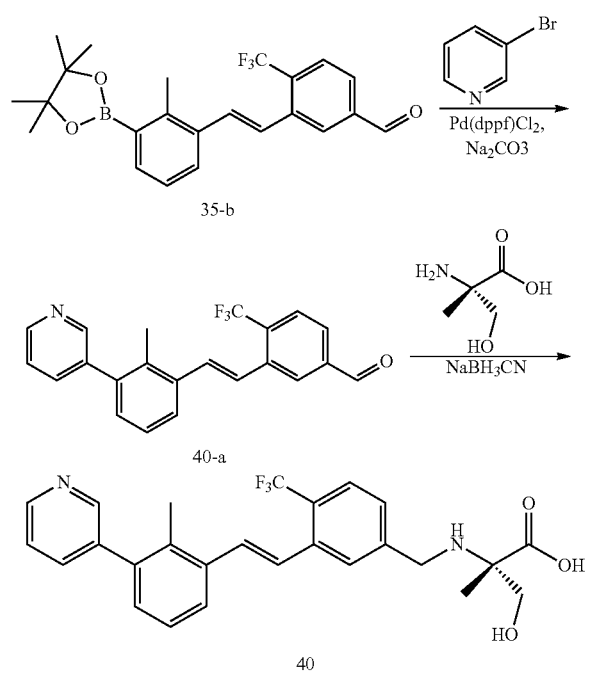

Synthesis of Compound 40-a

To a mixed solution of 3-bromopyridine (63.2 mg, 0.40 mmol) and 35-b (200.0 mg, 0.48 mmol) in 1,4-dioxane and water (20 mL, the volume ratio of 1,4-dioxane to water was 20:1) were added [1,1'-bis(diphenylphosphino)ferrocene] palladium dichloride (34.6 mg, 0.04 mmol) and sodium carbonate (106 mg, 1.0 mmol) at normal temperature. The reaction solution was heated to 80° C. and stirred overnight under nitrogen. After the completion of the reaction, the reaction solution was diluted with ethyl acetate, and washed with water three times and saturated brine once. The obtained organic phase was dried over anhydrous sodium sulfate, and concentrated by rotary evaporation to dryness to obtain a crude compound. The crude compound was purified by preparative plate (PE/EA=10:1 to 5:1) to obtain the target compound 40-a (57 mg, yield: 39%). LC-MS (ESI): m/z=368.0 [M+H]$^+$.

Synthesis of Compound 40

To a mixed solution of 40-a (57 mg, 0.155 mmol) and (S)-2-methylserine (37 mg, 0.31 mmol) in methanol and dichloromethane (10 mL, the volume ratio of methanol to dichloromethane was 1:1) was added acetic acid (19 mg, 0.31 mmol), and the reaction solution was stirred at room temperature for 1 hour. Then, to the reaction solution was added sodium cyanoborohydride (49 mg, 0.78 mmol) and was stirred overnight. After the completion of the reaction, the solvent was concentrated by rotary evaporation to dryness to obtain the crude compound. The crude compound was purified by preparative plate (DCM:MeOH=15:1) to obtain the target compound 40 (19 mg, yield: 26%). LC-MS (ESI): m/z=471.0 [M−H]$^+$.

$^1$H NMR (500 MHz, CD$_3$OD) δ: 8.58 (dd, J=2.0 Hz, J=5.5 Hz, 1H), 8.54 (s, 1H), 8.19 (s, 1H), 7.86 (d, J=8.0 Hz, 1H), 7.81 (d, J=7.5 Hz, 1H), 7.69-7.64 (m, 3H), 7.58-7.55 (m, 1H), 7.39-7.36 (m, 2H), 7.25 (d, J=12 Hz, 1H), 4.37 (d, J=12 Hz, 1H), 4.29 (d, J=12 Hz, 1H), 4.03 (d, J=12 Hz, 1H), 3.85 (d, J=12 Hz, 1H), 2.36 (s, 3H), 1.57 (s, 3H) ppm.

Example 41

(S,E)-3-hydroxy-2-methyl-2-(3-(2-methyl-3-(pyrazin-2-yl)styryl)-4-(trifluoromethyl)benzylamino)propanoic acid (Compound 41)

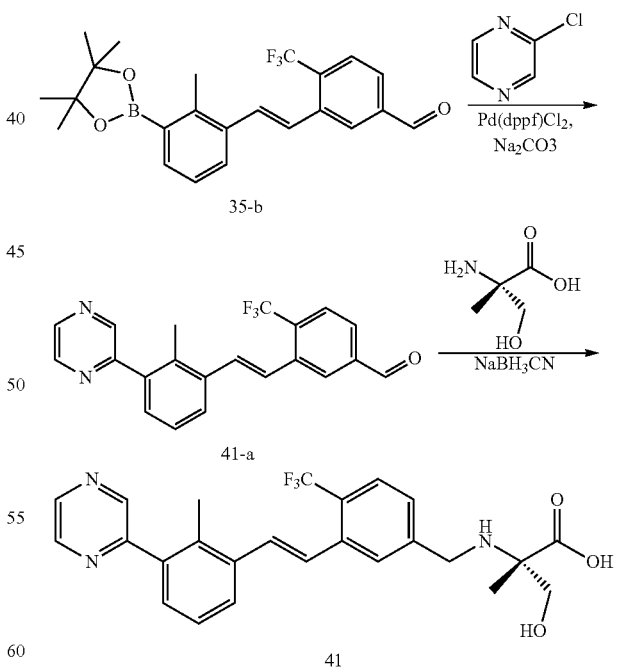

Synthesis of Compound 41-a

To a solution of 2-chloropyrazine (180 mg, 1.57 mmol) and 35-b (985 mg, 2.37 mmol) in 1,4-dioxane (5 mL) were added water (2 mL), anhydrous sodium carbonate (500 mg, 4.71 mmol) and 1,1'-bisdiphenylphosphinoferrocene palladium dichloride (87 mg, 0.11 mmol), and the reaction solution was heated to 80° C. overnight under nitrogen. The reaction solution was concentrated under reduced pressure, and the residue was purified by silica gel column chromatography (petroleum ether:ethyl acetate=3:1) to obtain 41-a (75 mg, yield: 13%) as a canary solid. LC-MS (ESI): m/z=369 [M+H]⁺.

Synthesis of Compound 41

To a mixed solution of 41-a (75 mg, 0.21 mmol) in dichloromethane (5 mL) and methanol (5 mL) were added (S)-2-methylserine (49 mg, 0.41 mmol) and acetic acid (1 drop). After the mixture was stirred at room temperature for 3 hours, sodium cyanoborohydride (20 mg, 0.32 mmol) was added. The reaction solution was stirred overnight at room temperature, concentrated to dryness, and purified by silica gel thin layer chromatography plate (dichloromethane:methanol=10:1) to obtain 41 (46 mg, yield: 40%) as an off-white solid. LC-MS (ESI): m/z=572 [M+H]⁺.

¹H-NMR (500 MHz, MeOD) δ: 8.78 (d, J=1 Hz, 1H), 8.73 (d, J=3 Hz, 1H), 8.64 (d, J=3 Hz, 1H), 8.19 (s, 1H), 7.65-7.82 (m, 4H), 7.37-7.43 (m, 3H), 4.33 (m, 2H), 4.01 (d, J=12 Hz, 1H), 3.85 (d, J=12 Hz, 1H), 2.42 (s, 3H), 1.58 (s, 3H) ppm.

Example 42

(S,E)-3-hydroxy-2-methyl-2-(3-(2-methyl-3-(2-methyl-2H-indazol-6-yl)-styryl)-4-(trifluoromethyl)benzylamino)propanoic acid (Compound 42)

Synthesis of Compound 42-a

6-Bromo-2-methyl-2H-indazole (210 mg, 1.0 mmol) and 35-b (560 mg, 1.35 mmol) were dissolved in 1,4-dioxane (5 mL), and water (2 mL), anhydrous sodium carbonate (191 mg, 3.0 mmol) and 1,1'-bisdiphenylphosphinoferrocene palladium dichloride (100 mg, 0.1 mmol) were added, and the reaction solution was heated to 80° C. and reacted overnight under nitrogen. The reaction solution was concentrated under reduced pressure, and the residue was purified by silica gel column chromatography (petroleum ether:ethyl acetate=10:1) to obtain 42-a (150 mg, yield: 36%) as a canary solid.

Synthesis of Compound 42

To a mixed solution of 42-a (150 mg, 0.36 mmol) dissolved in dichloromethane (5 mL) and methanol (5 mL) were added (S)-2-methylserine (85 mg, 0.72 mmol) and acetic acid (1 drop). After the mixture was stirred at room temperature for 3 hours, sodium cyanoborohydride (67 mg, 1.08 mmol) was added. The reaction solution was stirred overnight at room temperature, concentrated to dryness, and purified by silica gel thin layer chromatography plate (dichloromethane:methanol=10:1) to obtain 42 (56 mg, yield: 30%) as an off-white solid. LC-MS (ESI): m/z=524 [M+H]⁺.

¹H-NMR (500 MHz, MeOD) δ: 8.26 (s, 1H), 8.18 (s, 1H), 7.58-7.81 (m, 5H), 7.38 (s, 1H), 7.26-7.35 (m, 3H), 7.06 (d, J=9 Hz, 1H), 4.28 (m, 5H), 3.99 (d, J=12 Hz, 1H), 3.83 (d, J=12 Hz, 1H), 2.37 (s, 3H), 1.54 (s, 3H) ppm.

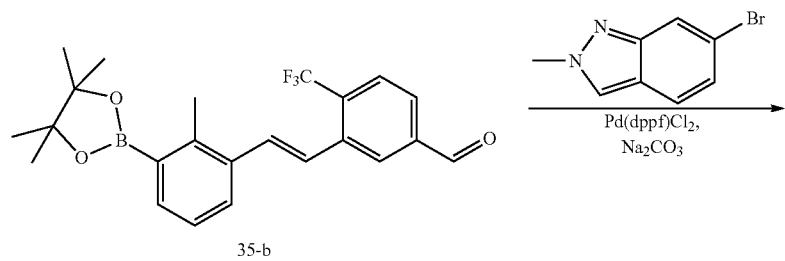

35-b

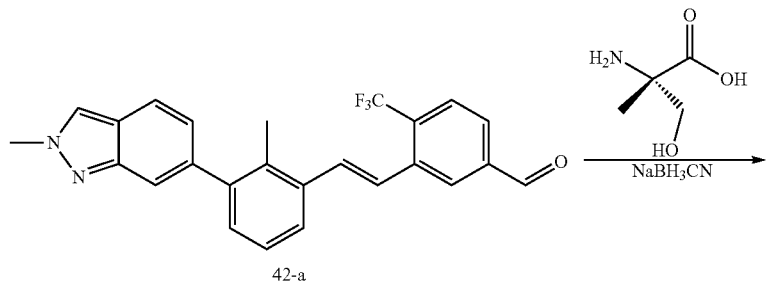

42-a

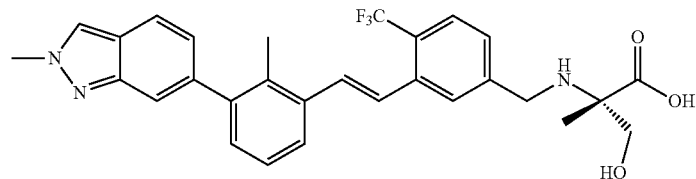

42

Example 43

(S,E)-3-hydroxy-2-methyl-2-(3-(2-methyl-3-(2-methylbenzo[d]oxazol-6-yl)-styryl)-4-(trifluoromethyl)benzylamino)-3-hydroxy-2-methylpropanoic acid (Compound 43)

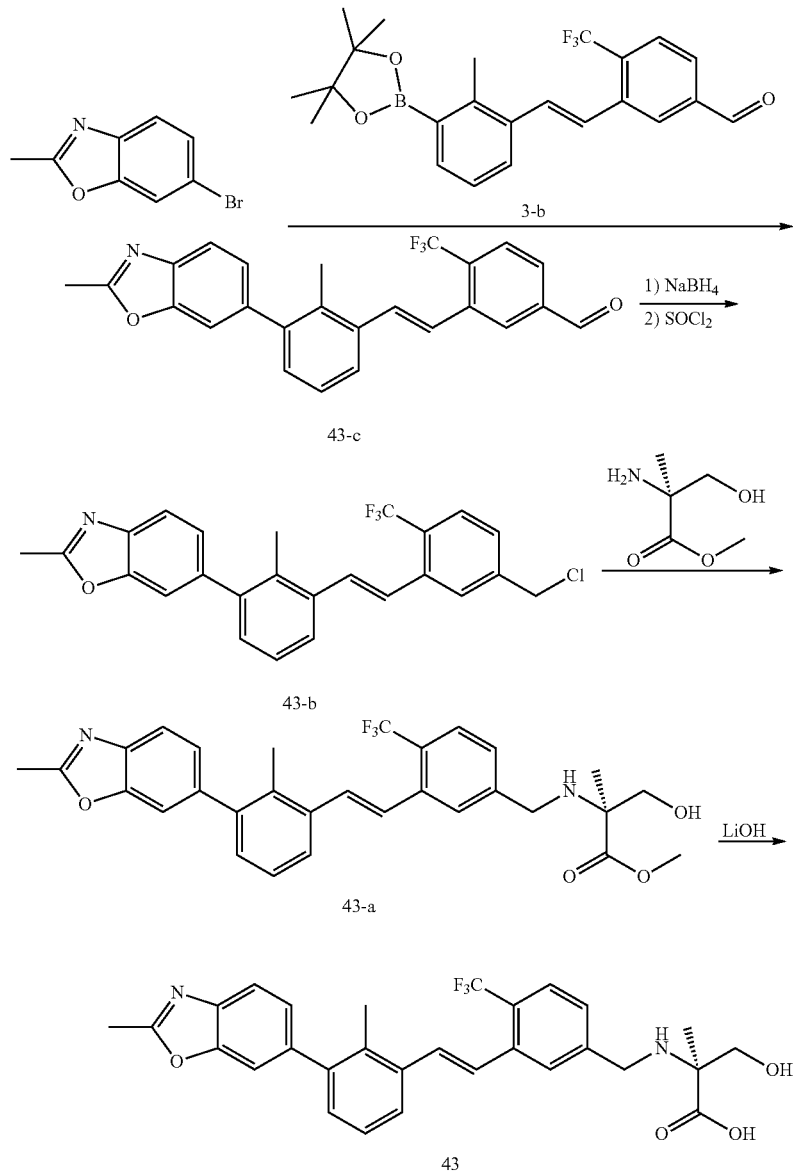

Synthesis of Compound 43-c

To a solution of 6-bromo-2-methyl-benzo[d]-oxazole (400 mg, 1.89 mmol) and 3-b (1104 mg, 2.65 mmol) dissolved in 1,4-dioxane (15 mL) were added water (3 mL), anhydrous sodium carbonate (600 mg, 5.66 mmol) and 1,1'-bisdiphenylphosphinoferrocene palladium dichloride (164 mg, 0.21 mmol), and the reaction solution was heated to 80° C. overnight under nitrogen. The reaction solution was concentrated under reduced pressure and purified by silica gel column chromatography (petroleum ether:ethyl acetate=5:1) to obtain 43-c (510 mg, yield: 64%) as a canary solid.

Synthesis of Compound 43-b 43-c (510 mg, 1.21 mmol) was dissolved in ethanol (10 mL), and sodium borohydride (92 mg, 2.42 mmol) was added. After the reaction solution was stirred at room temperature for 2 hours, the reaction solution was concentrated to dryness, and the residue was separated with ethyl acetate (50 mL) and water (50 mL). The organic phase was separated and dried, filtered, concentrated to dryness and redissolved in dichloromethane (20 mL). DMF (1 drop) and sulfoxide chloride (3 mL) were added and the mixture was stirred at room temperature for 2 hours. The residue was concentrated to dryness to obtain 43-b, which was directly used in the next reaction.

Synthesis of Compound 43-a 43-b (360 mg, 0.82 mmol) and L-2-methylserine methyl ester hydrochloride (127 mg, 0.82 mmol) were dissolved in acetonitrile (10 mL), and potassium carbonate (339 mg, 2.46 mmol) and sodium iodide (125 mg, 0.82 mmol) were added. The mixture was heated to 85° C. for 8 hours and concentrated to dryness, and the residue was separated with ethyl acetate (50 mL) and water (50 mL). The organic phase was separated, dried over anhydrous sodium sulfate, filtered, concentrated to dryness and purified by a column (petroleum ether:ethyl acetate=1:1) to obtain 43-a (150 mg, yield: 34%) as a canary oil by column chromatography. LC-MS (ESI): m/z=539 $[M+H]^+$.

Synthesis of Compound 43

To a mixed solution of 43-a (150 mg, 0.28 mmol) in methanol (2 mL) and water (2 mL) was added lithium hydroxide (18 mg, 0.42 mmol). The reaction solution was stirred overnight at room temperature and concentrated to dryness, and the residue was diluted with water. After acidification, the pH was 3 to 4. The mixture was filtered, washed with water, and dried to obtain 43 (67 mg, yield: 46%) as a canary solid. LC-MS (ESI): m/z=525 $[M+H]^+$. $^1$H-NMR (500 MHz, MeOD) δ: 8.18 (s, 1H), 7.53-7.81 (m, 6H), 7.25-7.38 (m, 4H), 4.32 (m, 2H), 4.00 (m, 1H), 3.84 (d, J=12 Hz, 1H), 2.69 (s, 3H), 2.35 (s, 3H), 1.53 (s, 3H) ppm.

Effect Example

Homogenouse Time-Resolved Fluorescence (HTRF) binding assay was used to determine the binding activity of the compound of the present disclosure to PD-1/PD-L1.

The purchased kit (CisBio, #64CUS000C-1) contained the reagents required for experiments such as PD-1, PD-L1, anti-tag1-Eu, Anti-tag2-XL665, Dilute Buffer and Detection Buffer.

Experimental Procedure

1. The compound was formulated to 10 concentrations with a three-fold concentration gradient with 100% DMSO.

2. The solution of the compound in DMSO was added to Dilute Buffer, and mixed evenly and then transferred to a 96-well plate.

3. PD-L1 was diluted with Dilute Buffer and added to the 96-well plate above.

4. PD-1 was diluted with Dilute Buffer, then added to the 96-well plate above and incubated at room temperature for 30 minutes.

5. One portion of anti-tag1-Eu and one portion of anti-tag2-XL665 were added to Detection Buffer, mixed evenly and transferred to the 96-well plate above.

6. The mixed solution in the 96-well plate were incubated at room temperature for 1 to 24 hours.

7. HTRF values were read by Envision.

Experimental Results

The biological activity of the compound of the present disclosure was determined by the above assay, and the measured results were as followed (Table 1).

TABLE 1

IC$_{50}$ values of some compounds of the present disclosure binding to PD-1/PD-L1

| Compound | IC$_{50}$ (μM) | Compound | IC$_{50}$ (μM) |
|---|---|---|---|
| 1 | 0.014 | 2 | 3.1 |
| 3 | 0.046 | 5 | 0.023 |
| 6 | 0.32 | 7 | 1.4 |
| 8 | 0.042 | 9 | 0.057 |
| 12 | 0.024 | 13 | 0.013 |
| 14 | 0.019 | 15 | 0.014 |
| 16 | 0.013 | 17 | 0.020 |
| 18 | 0.046 | 19 | 0.061 |
| 20 | 0.018 | 21 | 0.085 |
| 22 | 0.044 | 23 | 0.026 |
| 24 | 0.430 | 25 | 0.066 |
| 26 | 0.020 | 27 | 0.018 |
| 28 | 0.029 | 29 | 0.019 |
| 30 | 0.027 | 31 | 0.041 |
| 32 | 0.024 | 33 | 0.230 |
| 34 | 0.180 | 35 | 1.1 |
| 36 | >10 | 37 | 1.3 |
| 38 | >10 | 39 | 2.2 |
| 40 | 0.580 | 41 | 0.540 |
| 42 | 0.880 | 43 | 0.540 |

Pharmacokinetic Experiment in Mice

Glipizide (molecular formula was $C_{21}H_{27}N_5O_4S$, molecular weight was 445.5 g/mol, Analytical Reagent) purchased from Sigma-Aldrich (U.S.A.), was used as the internal standard for analysis. Methanol, acetonitrile and formic acid (HPLC grade) were purchased from Sigma-Aldrich (U.S.A.), and pure water was purchased from Hangzhou Wahaha Group Co., Ltd. (Hangzhou, China). Other chemical reagents were all analytical reagents.

CD1 male mice, six per group, 6-7 weeks old, 29-31 g, were purchased from LC Laboratory Animal Co. LTD. Before the experiment, the animals should be kept for at least 3 days to adapt to the environment. Throughout the experiment, the animals were required to fast overnight, and allowed to drink water freely during the period, and the surviving animals resumed feeding 4 hours after administration.

Experimental Procedure

1. The compound was formulated into a solution with a concentration of 0.4 mg/mL with 10% DMSO, 10% Solutol HS 15 and 80% Saline.

2. The above prepared solution was administered to 3 mice by tail vein injection (compound dosage was 2 mg/kg), and was administered to another 3 mice by oral gavage (compound dosage was 10 mg/kg) simultaneously.

3. Approximately 30 μL of blood was collected from each of the above 6 mice at 5 minutes, 15 minutes, 30 minutes, 1 hour, 2 hours, 4 hours, 8 hours and 24 hours after administration into the EDTA-K2 anticoagulation tube (set on wet ice), and 20 μL of blood was immediately diluted with 60 μL of water, and then put in the refrigerator at −70° C. for long-term storage until the sample was analyzed.

4.20 μL of the above solution was transferred into a 96-well deep well sample plate, and 150 μL of glipizide internal standard acetonitrile solution (the concentration was 100 ng/mL) was added, vortexed for 10 min, and centrifuged at 58 rpm for 10 min. 1 μL of the supernatant was taken for LCMSMS analysis.

5. Based on the drug concentration-time data, WinNonlin 6.4 software (USA) was used to calculate the pharmacokinetic parameters of the compound according to the non-compartment model.

EXPERIMENTAL RESULTS

The results of the pharmacokinetics of the compounds of the present disclosure in mice were as followed (Table 2).

TABLE 2

Oral bioavailability of the pharmacokinetics of some compounds of the present disclosure in mice

| Compound | Oral bioavailability |
|---|---|
| 13 | 16.1% |
| 27 | 52.3% |
| 29 | 38.2% |

What is claimed is:

1. An aromatic vinyl or aromatic ethyl derivative represented by formula (II), a pharmaceutically acceptable salt or a prodrug thereof:

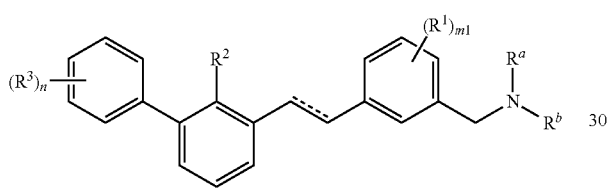

(II)

wherein,

===== is a single bond or a double bond;

each of $R^1$ is identical or different, and is independently deuterium, halogen, substituted or unsubstituted hydroxyl, substituted or unsubstituted amino, substituted or unsubstituted alkyl, or substituted or unsubstituted alkoxy;

or two adjacent $R^1$ together with the two carbon atoms to which they are attached form a 5- to 7-membered carbocyclic ring or heterocarbocyclic ring; in the heterocarbocyclic ring, the heteroatom(s) is(are) oxygen and/or nitrogen, and the number of the heteroatom(s) is 1 to 4;

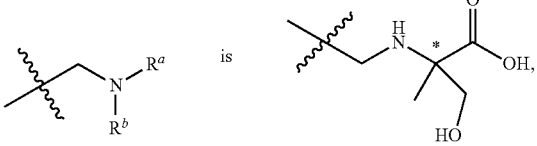 is wherein, the carbon labelled by * is an S-configuration chiral carbon, an R-configuration chiral carbon or an achiral carbon;

$R^2$ is substituted or unsubstituted alkyl or halogen;

each of $R^3$ is identical or different, and is independently deuterium, halogen, substituted or unsubstituted alkylthio, substituted or unsubstituted hydroxyl, substituted or unsubstituted amino, substituted or unsubstituted alkyl, substituted or unsubstituted alkoxy,

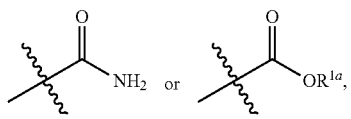

wherein $R^{1a}$ is $C_1$-$C_4$ alkyl;

the substituent(s) in the substituted alkyl in each of $R^1$, $R^2$ and each of $R^3$, the substituent(s) in the substituted alkoxy in each of $R^1$ and each of $R^3$, and the substituent(s) in the substituted alkylthio in each of $R^3$ are one or more selected from halogen, $C_{1-4}$ alkyl, hydroxyl,

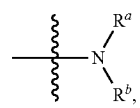

$C_{1-4}$ alkoxy, $C_{1-4}$ carboxyl, $C_{1-4}$ ester group and $C_{1-4}$ amide group; when there are more substituents than one, then the substituents are identical or different; $R^a$ and $R^b$ are independently hydrogen, or, substituted or unsubstituted alkyl; in $R^a$ or $R^b$, the substituent(s) in the substituted alkyl is(are) one or more selected from halogen, $C_1$-$C_4$ alkyl, hydroxyl,

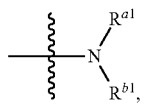

$C_1$-$C_4$ alkoxy, $C_1$-$C_4$ carboxyl, $C_1$-$C_4$ ester group and $C_1$-$C_4$ amide group; $R^{a1}$ and $R^{b1}$ are independently hydrogen or $C_1$-$C_4$ alkyl;

in each of $R^1$ or $R^3$, the substituent(s) in the substituted hydroxyl or the substituted amino is(are) one or more selected from $C_{1-4}$ alkyl, $C_{1-4}$ alkoxy, $C_{1-4}$ carboxyl, $C_{1-4}$ ester group and $C_{1-4}$ amide group;

m1 is 0, 1 or 2;

n is 0, 1, 2 or 3; when ===== is a double bond and m1 is 1, then $R^1$ is located on ortho positions of the phenyl;

when ===== is a double bond and m1 is 2, then two of $R^1$ are adjacent, and the two adjacent $R^1$ together with the two carbon atoms to which they are attached form a 5- to 7-membered heterocarbocyclic ring.

2. The aromatic vinyl or aromatic ethyl derivative represented by formula (II), the pharmaceutically acceptable salt or the prodrug thereof as defined in claim 1, wherein, when the substituent(s) in the substituted alkyl in each of $R^1$, $R^2$ and each of $R^3$, the substituent(s) in the substituted alkoxy in each of $R^1$ and each of $R^3$, and the substituent(s) in the substituted alkylthio in each of $R^3$ are halogen, then the halogen is F, Cl, Br or I;

and/or, when the substituent(s) in the substituted alkyl in each of $R^1$, $R^2$ and each of $R^3$, the substituent(s) in the substituted alkoxy, the substituted hydroxyl or the substituted amino in each of $R^1$ and each of $R^3$, and the substituent(s) in the substituted alkylthio in each of $R^3$ are $C_1$-$C_4$ alkyl, then the $C_1$-$C_4$ alkyl is methyl, ethyl, n-propyl, isopropyl, n-butyl, isobutyl or tert-butyl;

and/or, when the substituent(s) in the substituted alkyl in each of $R^1$, $R^2$ and each of $R^3$, the substituent(s) in the substituted alkoxy in each of $R^1$ and each of $R^3$, and the substituent(s) in the substituted alkylthio in each of $R^3$ are

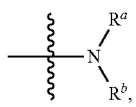

and $R^a$ or $R^b$ is substituted alkyl, and the substituent(s) in the substituted alkyl is(are) halogen, then the halogen is F, Cl, Br or I;

and/or, when the substituent(s) in the substituted alkyl in each of $R^1$, $R^2$ and each of $R^3$, the substituent(s) in the substituted alkoxy in each of $R^1$ and each of $R^3$, and the substituent(s) in the substituted alkylthio in each of $R^3$ are

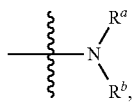

and $R^a$ or $R^b$ is substituted alkyl, and the substituent(s) in the substituted alkyl is(are) $C_1$-$C_4$ alkyl, then the $C_1$-$C_4$ alkyl is methyl, ethyl, n-propyl, isopropyl, n-butyl, isobutyl or tert-butyl;

and/or, when the substituent(s) in the substituted alkyl in each of $R^1$, $R^2$ and each of $R^3$, the substituent(s) in the substituted alkoxy in each of $R^1$ and each of $R^3$, and the substituent(s) in the substituted alkylthio in each of $R^3$ are

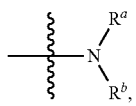

$R^a$ or $R^b$ is substituted alkyl, and the substituent(s) in the substituted alkyl is(are)

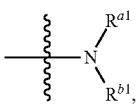

and $R^{a1}$ or $R^{b1}$ is $C_1$-$C_4$ alkyl, then the $C_1$-$C_4$ alkyl is methyl, ethyl, n-propyl, isopropyl, n-butyl, isobutyl or tert-butyl;

and/or, when the substituent(s) in the substituted alkyl in each of $R^1$, $R^2$ and each of $R^3$, the substituent(s) in the substituted alkoxy in each of $R^1$ and each of $R^3$, and the substituent(s) in the substituted alkylthio in each of $R^3$ are

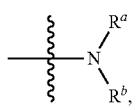

$R^a$ or $R^b$ is substituted alkyl, and the substituent(s) in the substituted alkyl is(are) $C_1$-$C_4$ alkoxy, then the $C_{1\text{-}4}$ alkoxy is methoxy, ethoxy, n-propoxy, isopropoxy, n-butoxy, isobutoxy or tert-butoxy;

and/or, when the substituent(s) in the substituted alkyl in each of $R^1$, $R^2$ and each of $R^3$, the substituent(s) in the substituted alkoxy in each of $R^1$ and each of $R^3$, and the substituent(s) in the substituted alkylthio in each of $R^3$ are

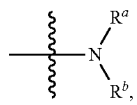

$R^a$ or $R^b$ is substituted alkyl, and the substituent(s) in the substituted alkyl is(are) $C_1$-$C_4$ carboxyl, then the $C_{1\text{-}4}$ carboxyl is

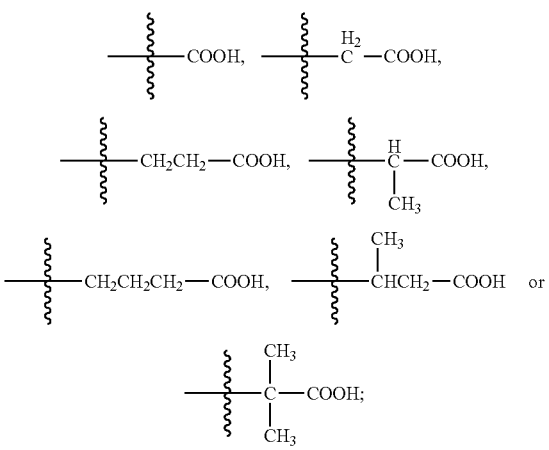

and/or, when the substituent(s) in the substituted alkyl in each of $R^1$, $R^2$ and each of $R^3$, the substituent(s) in the substituted alkoxy in each of $R^1$ and each of $R^3$, and the substituent(s) in the substituted alkylthio in each of $R^3$ are

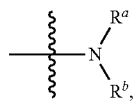

and $R^a$ or $R^b$ is substituted alkyl, and the substituent(s) in the substituted alkyl is(are) $C_1$-$C_4$ ester group, then the $C_1$-$C_4$ ester group is

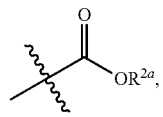

and $R^{2a}$ is methyl, ethyl, n-propyl, isopropyl, n-butyl, isobutyl or tert-butyl;

and/or, when the substituent(s) in the substituted alkyl in each of $R^1$, $R^2$ and each of $R^3$, the substituent(s) in the substituted alkoxy in each of $R^1$ and each of $R^3$, and the substituent(s) in the substituted alkylthio in each of $R^3$ are

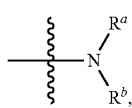

and $R^a$ or $R^b$ is substituted alkyl, and the substituent(s) in the substituted alkyl is(are) $C_1$-$C_4$ amide group, then the $C_1$-$C_4$ amide group is

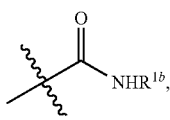

and $R^{1b}$ is hydrogen, methyl, ethyl, n-propyl, isopropyl, n-butyl, isobutyl or tert-butyl;

and/or, when the substituent(s) in the substituted alkyl in each of $R^1$, $R^2$ and each of $R^3$, the substituent(s) in the substituted alkoxy, the substituted hydroxyl or the substituted amino in each of $R^1$ and each of $R^3$, and the substituent(s) in the substituted alkylthio in each of $R^3$ are $C_1$-$C_4$ alkoxy, then the $C_{1-4}$ alkoxy is methoxy, ethoxy, n-propoxy, isopropoxy, n-butoxy, isobutoxy or tert-butoxy;

and/or, when the substituent(s) in the substituted alkyl in each of $R^1$, $R^2$ and each of $R^3$, the substituent(s) in the substituted alkoxy, the substituted hydroxyl or the substituted amino in each of $R^1$ and each of $R^3$, and the substituent(s) in the substituted alkylthio in each of $R^3$ are $C_1$-$C_4$ carboxyl, then the $C_{1-4}$ carboxyl is

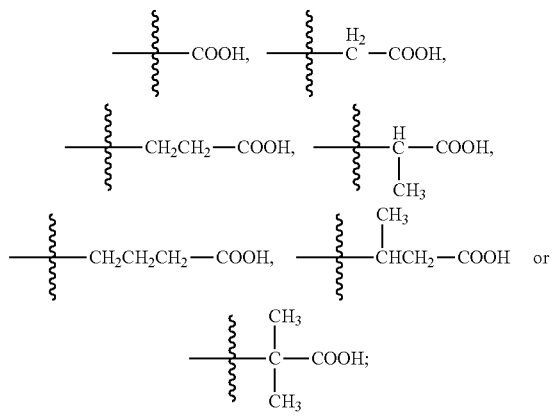

and/or, when the substituent(s) in the substituted alkyl in each of $R^1$, $R^2$ and each of $R^3$, the substituent(s) in the substituted alkoxy, the substituted hydroxyl or the substituted amino in each of $R^1$ and each of $R^3$, and the substituent(s) in the substituted alkylthio in each of $R^3$ are $C_1$-$C_4$ ester group, then the $C_1$-$C_4$ ester group is

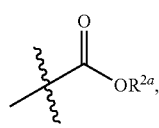

and $R^{2a}$ is methyl, ethyl, n-propyl, isopropyl, n-butyl, isobutyl or tert-butyl;

and/or, when the substituent(s) in the substituted alkyl in each of $R^1$, $R^2$ and each of $R^3$, the substituent(s) in the substituted alkoxy, the substituted hydroxyl or the substituted amino in each of $R^1$ and each of $R^3$, and the substituent(s) in the substituted alkylthio in each of $R^3$ are $C_1$-$C_4$ amide group, then the $C_1$-$C_4$ amide group is

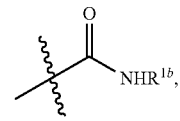

and $R^{1b}$ is hydrogen, methyl, ethyl, n-propyl, isopropyl, n-butyl, isobutyl or tert-butyl.

3. The aromatic vinyl or aromatic ethyl derivative represented by formula (II), the pharmaceutically acceptable salt or the prodrug thereof as defined in claim 1, wherein,
in each of $R^1$, $R^2$ and each of $R^3$, the halogen is F, Cl, Br or I;
and/or, in each of $R^1$, $R^2$ and each of $R^3$, the substituted or unsubstituted alkyl is substituted or unsubstituted $C_1$-$C_4$ alkyl;
and/or, in each of $R^1$ and each of $R^3$, the substituted or unsubstituted alkoxy is substituted or unsubstituted $C_1$-$C_4$ alkoxy;
and/or, in each of $R^3$, the substituted or unsubstituted alkylthio is —S—$R^s$, wherein, $R^s$ is substituted or unsubstituted $C_1$-$C_4$ alkyl;
and/or, in each of $R^3$, in

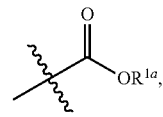

$R^{1a}$ is methyl, ethyl, n-propyl, isopropyl, n-butyl, isobutyl or tert-butyl.

4. The aromatic vinyl or aromatic ethyl derivative represented by formula (II), the pharmaceutically acceptable salt or the prodrug thereof as defined in claim 1, wherein,
each of $R^1$ is independently halogen, or, substituted or unsubstituted alkyl; or two adjacent $R^1$ together with the two carbon atoms to which they are attached form a 5- to 7-membered heterocarbocyclic ring;
and/or, $R^2$ is alkyl or halogen;
and/or, each of $R^3$ is independently halogen, alkylthio or alkoxy;
and/or, n is 0, 1, 2 or 3;
and/or, is m1 is 1 or 2.

5. The aromatic vinyl or aromatic ethyl derivative represented by formula (II), the pharmaceutically acceptable salt or the prodrug thereof as defined in claim 4, wherein,
when $R^1$ is substituted alkyl, the substituent(s) in the substituted alkyl is(are) one or more selected from halogen and

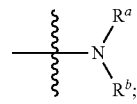

$R^a$ and $R^b$ are independently hydrogen, or, substituted or unsubstituted alkyl; in $R^a$ or $R^b$, the substituent(s) in the substituted alkyl is(are) one or more selected from hydroxyl and $C_1$-$C_4$ carboxyl;

and/or, when n is 1, then $R^3$ is halogen, alkylthio or alkoxy; and $R^3$ is located on ortho, meta or para position of the phenyl;

and/or, when n is 2, then two $R^3$ are located on ortho and meta positions of the phenyl, and the two $R^3$ are identical or different;

and/or, when m1 is 1, then $R^1$ is located on ortho positions of the phenyl; $R^1$ located on ortho position of the phenyl is alkyl or alkyl substituted by halogen and/or, when m1 is 2, then two of $R^1$ are adjacent, and the two adjacent $R^1$ together with the two carbon atoms to which they are attached form a 5- to 7-membered heterocarbocyclic ring.

6. The aromatic vinyl or aromatic ethyl derivative represented by formula (II), the pharmaceutically acceptable salt or the prodrug thereof as defined in claim 5, wherein, $R^1$ located on ortho position of the phenyl is $C_{1-4}$ alkyl or $C_{1-4}$ alkyl substituted by one or more halogen, such as trifluoromethyl;

and/or, the alkyl substituted by

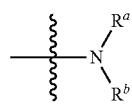

is $C_1$-$C_4$ alkyl substituted by

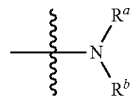

7. The aromatic vinyl or aromatic ethyl derivative represented by formula (II), the pharmaceutically acceptable salt or the prodrug thereof as defined in claim 1, wherein, each of $R^1$ is independently H, or, substituted or unsubstituted alkyl; or two adjacent $R^1$ together with the two carbon atoms to which they are attached form a 5- to 7-membered heterocarbocyclic ring; the substituent(s) in the substituted alkyl is(are) one or more selected from halogen and

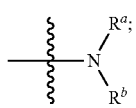

$R^a$ and $R^b$ are independently hydrogen, or, substituted or unsubstituted alkyl; in $R^a$ or $R^b$, the substituent(s) in the substituted alkyl is(are) one or more selected from hydroxyl and $C_1$-$C_4$ carboxyl;

$R^2$ is alkyl or halogen;

each of $R^3$ is independently H, halogen, alkylthio or alkoxy;

n is 0, 1, 2 or 3; when n is 1, then $R^3$ is halogen, alkylthio or alkoxy; and $R^3$ is located on ortho, meta or para position of the phenyl; when n is 2, then two $R^3$ are located on ortho and meta positions of the phenyl, wherein, the two $R^3$ are identical or different;

m1 is 1 or 2; when m1 is 1, then $R^1$ is located on ortho, $R^1$ located on ortho position of the phenyl is alkyl or alkyl substituted by halogen;

when m1 is 2, then two of $R^1$ are adjacent, and the two adjacent $R^1$ together with the two carbon atoms to which they are attached form a 5- to 7-membered heterocarbocyclic ring.

8. The aromatic vinyl or aromatic ethyl derivative represented by formula (II), the pharmaceutically acceptable salt or the prodrug thereof as defined in claim 1, wherein,

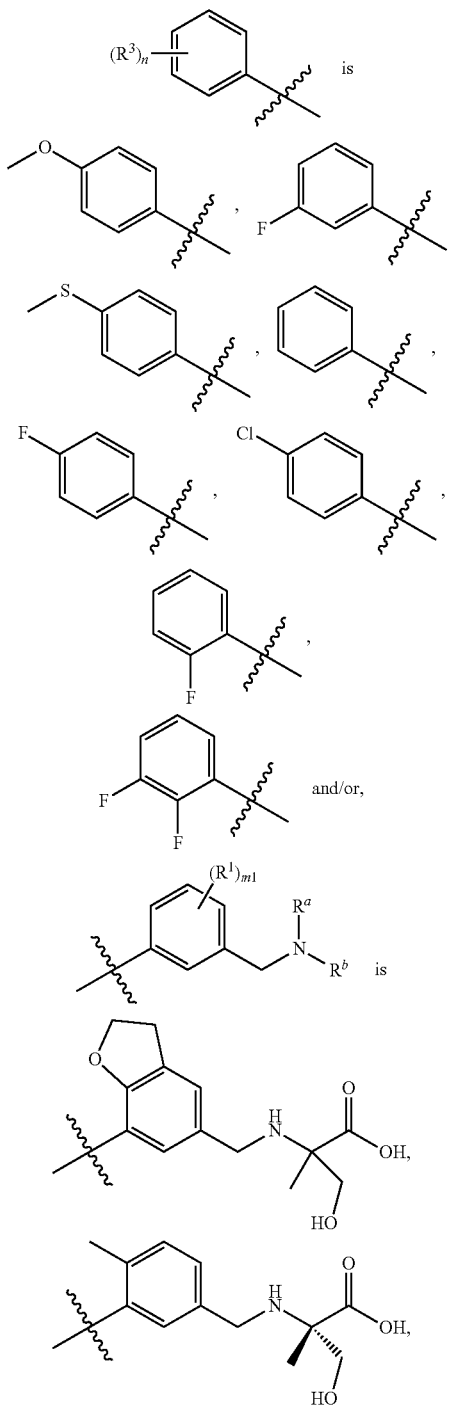

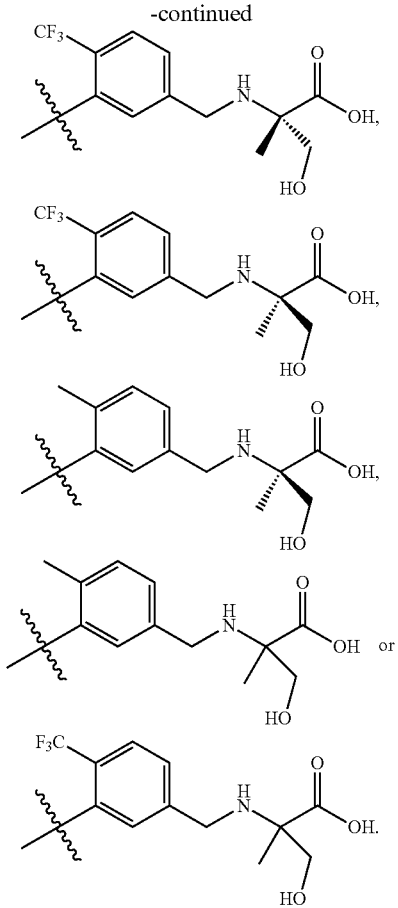
9. The aromatic vinyl or aromatic ethyl derivative represented by formula (II), the pharmaceutically acceptable salt or the prodrug thereof as defined in claim 1, wherein, the aromatic vinyl or aromatic ethyl derivative represented by formula (II) is:
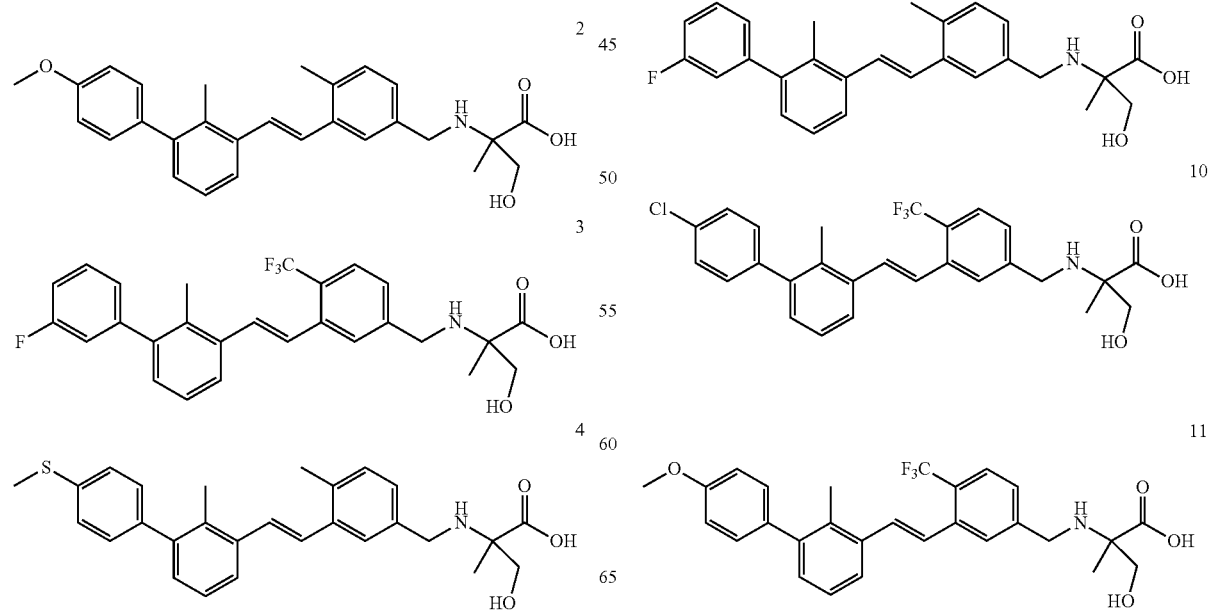
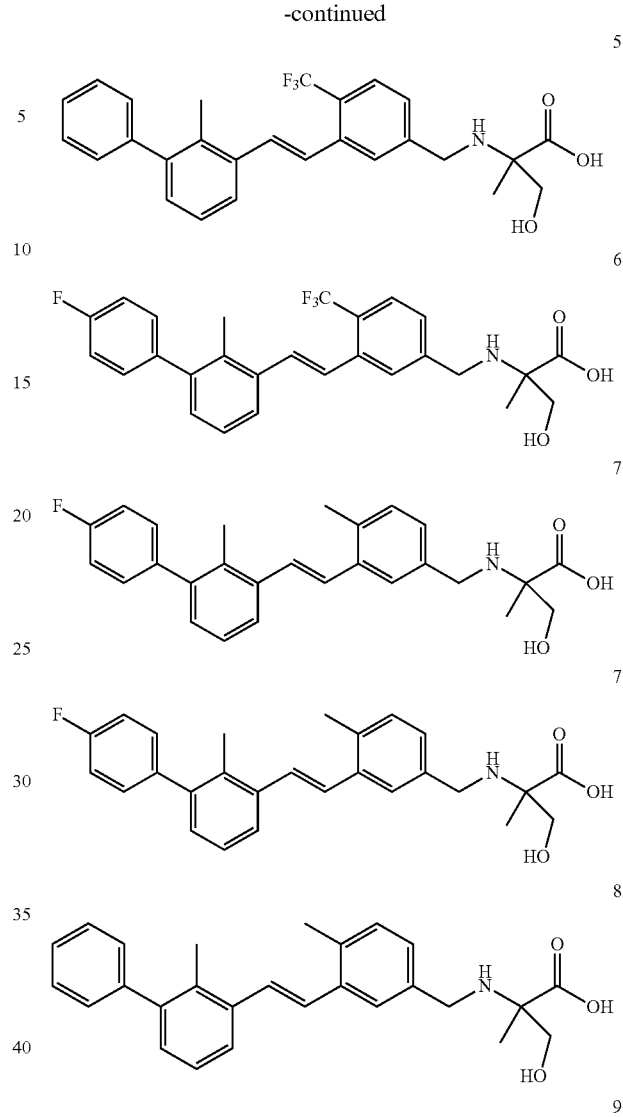

-continued

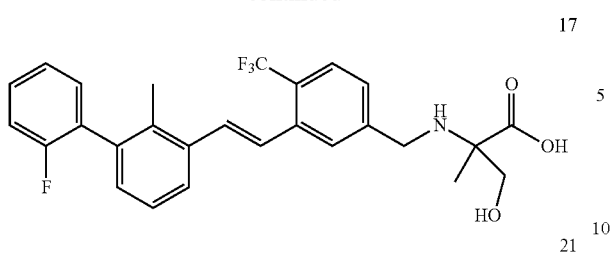

17

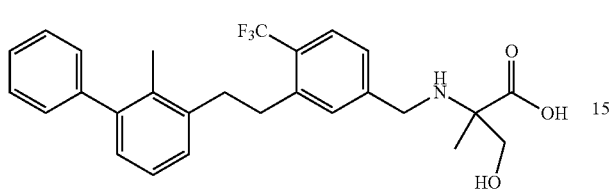

21

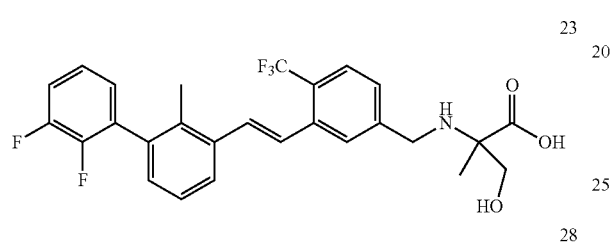

23

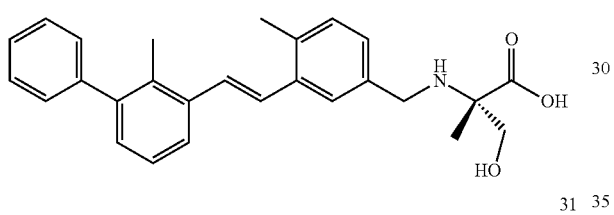

28

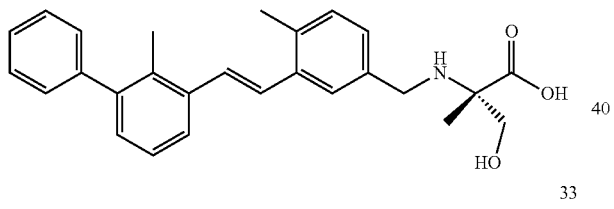

31

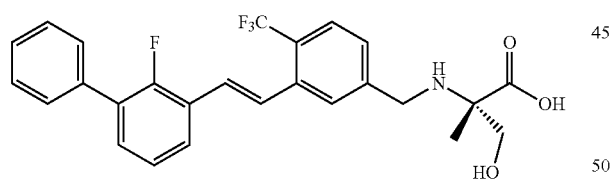

33

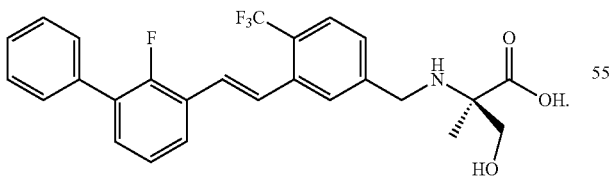

34

10. A method for preparing the aromatic vinyl or aromatic ethyl derivative represented by formula (II) as defined in claim 1, which comprises the following step: conducting a reductive amination reaction of compound (I-a) with

to obtain the compound represented by formula (II);

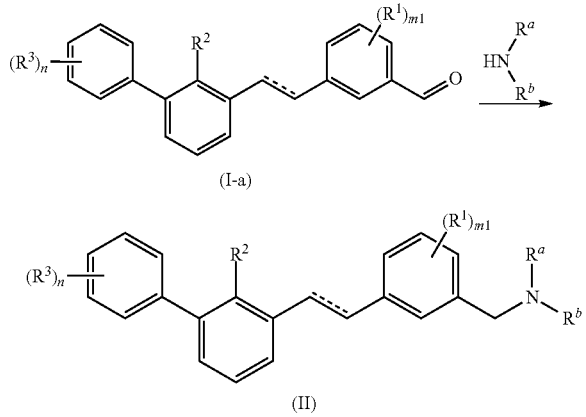

in the formula above, the definitions of $R^1$, $R^2$, $R^3$, n, m1, $R^a$ and $R^b$ are as defined in claim 1.

11. The method as defined in claim 10, wherein, the method for preparing the compound (I-a) comprises the following step: in a solvent, in the presence of a palladium catalyst, conducting a coupling reaction of compound (II-b) and

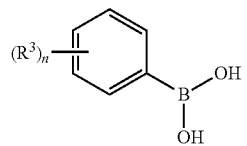

to obtain the compound (I-a);

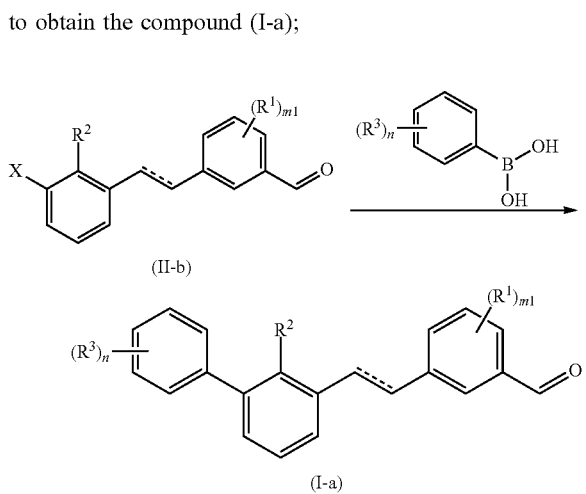

wherein, the definitions of $R^1$, $R^2$, $R^3$, n, m1, $R^a$ and $R^b$ are as defined in claim 10, and X is halogen.

12. A compound represented by formula (I-a):
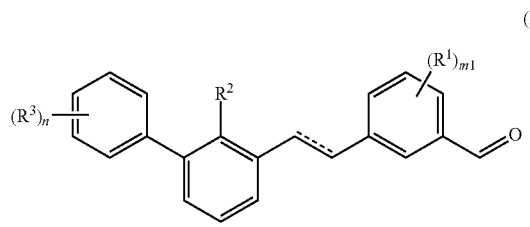
(I-a)
wherein, the definitions of $R^1$, $R^2$, $R^3$ and n are as defined in claim 1, and m1 is 0, 1 or 2; and
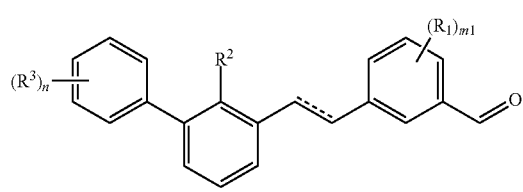
is not
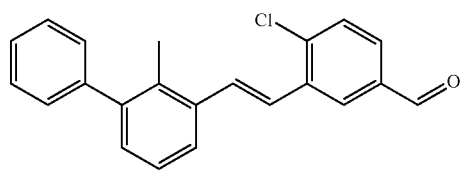
or
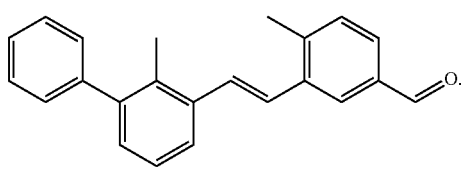
13. The compound represented by formula (I-a) as defined in claim 12, which is:
2-a
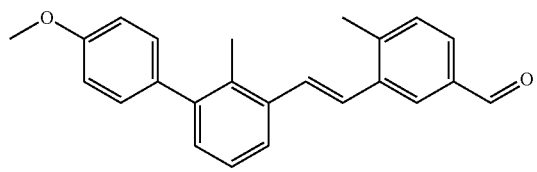
3-a
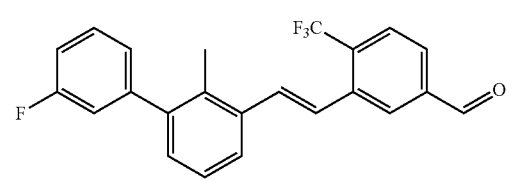
4-a
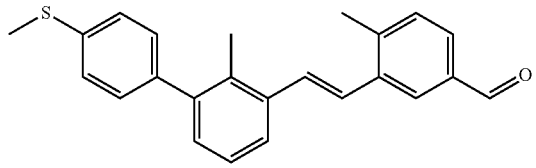
5-a
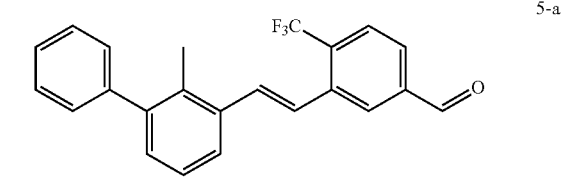
6-a
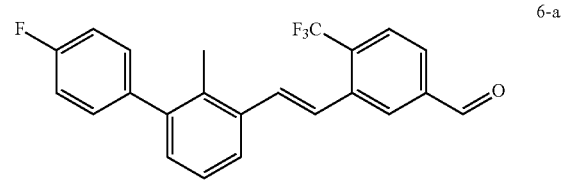
7-a
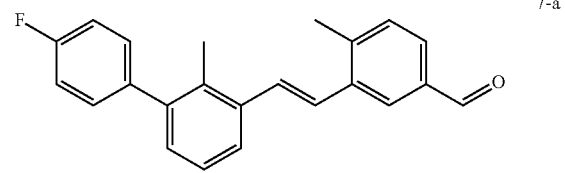
8-a
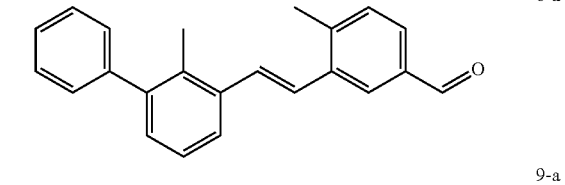
9-a
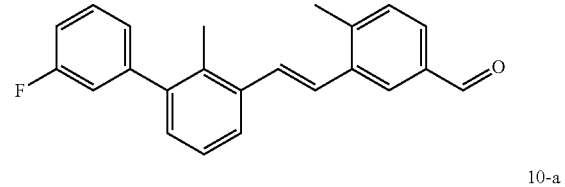
10-a
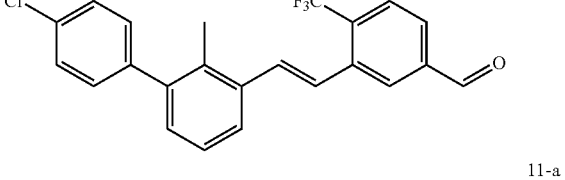
11-a
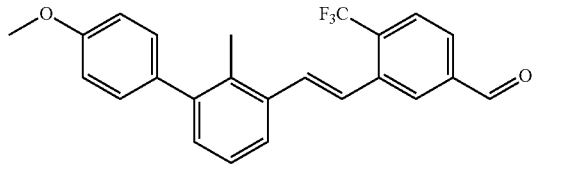
12-a
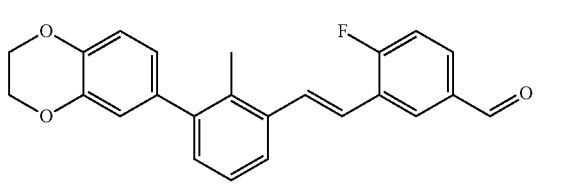

-continued

14. A pharmaceutical composition, which comprises a therapeutically effective amount of the aromatic vinyl or aromatic ethyl derivative represented by formula (II), the pharmaceutically acceptable salt or the prodrug thereof as defined in claim 1, and a pharmaceutically acceptable carrier and/or a diluent.

15. A method for inhibiting PD-1 and/or PD-L1 in a subject in need thereof, comprising administering a therapeutically effective amount of the aromatic vinyl or aromatic ethyl derivative represented by formula (II), the pharmaceutically acceptable salt or the prodrug thereof as defined in claim 1 to the subject.

16. The method for inhibiting PD-1 and/or PD-L1 in a subject in need thereof, comprising administering a therapeutically effective amount of the pharmaceutical composition as defined in claim 14 to the subject.

17. The aromatic vinyl or aromatic ethyl derivative represented by formula (II), the pharmaceutically acceptable salt or the prodrug thereof as defined in claim 1, wherein, in each of $R^1$, $R^2$ and each of $R^3$, the substituted or unsubstituted $C_1$-$C_4$ alkyl is substituted or unsubstituted methyl, substituted or unsubstituted ethyl, substituted or unsubstituted n-propyl, substituted or unsubstituted isopropyl, substituted or unsubstituted n-butyl, substituted or unsubstituted isobutyl, or, substituted or unsubstituted tert-butyl.

18. The aromatic vinyl or aromatic ethyl derivative represented by formula (II), the pharmaceutically acceptable salt or the prodrug thereof as defined in claim 1, wherein,

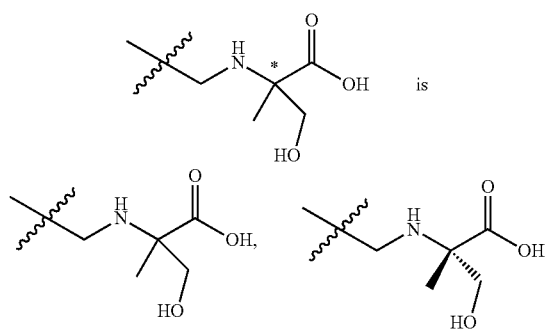

is

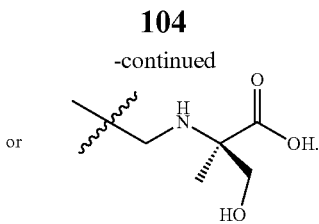

or

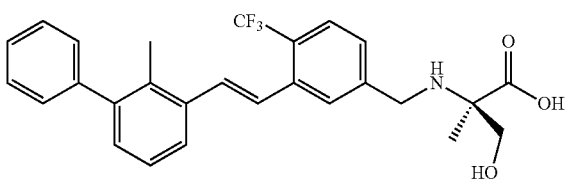

19. The aromatic vinyl or aromatic ethyl derivative represented by formula (II), the pharmaceutically acceptable salt or the prodrug thereof as defined in claim 1, wherein, the aromatic vinyl or aromatic ethyl derivative represented by formula (II) is:

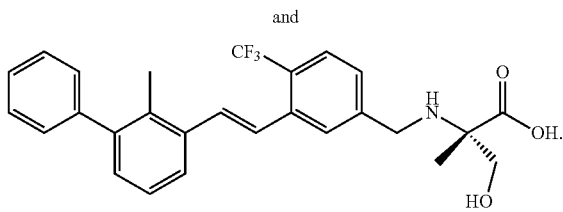

and

* * * * *